US012797259B2

(12) United States Patent
Taylor et al.

(10) Patent No.: US 12,797,259 B2
(45) Date of Patent: Nov. 17, 2026

(54) METHOD AND APPARATUS FOR BREAKING BOND REGIONS IN ABSORBENT ARTICLES WITH FRANGIBLE PATHWAYS

(71) Applicant: The Procter & Gamble Company, Cincinnati, OH (US)

(72) Inventors: Kaitlyn Nicole Taylor, Maineville, OH (US); Jeffry Rosiak, Loveland, OH (US); Michael Devin Long, Harrison Township, OH (US); Jason Edward Naylor, Cincinnati, OH (US); Jeromy Thomas Raycheck, South Lebanon, OH (US); Keith Richard Willhaus, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 90 days.

(21) Appl. No.: 18/967,797

(22) Filed: Dec. 4, 2024

(65) Prior Publication Data

US 2025/0195284 A1 Jun. 19, 2025

Related U.S. Application Data

(60) Provisional application No. 63/610,082, filed on Dec. 14, 2023.

(51) Int. Cl.
*A61F 13/15* (2006.01)

(52) U.S. Cl.
CPC .................. *A61F 13/15739* (2013.01); *A61F 13/15764* (2013.01)

(58) Field of Classification Search
CPC .......... A61F 13/15739; A61F 13/15764; A61F 13/15585; A61F 13/15699; A61F 13/15723; A61F 13/496
See application file for complete search history.

(56) References Cited

U.S. PATENT DOCUMENTS

| | | | |
|---|---|---|---|
| 4,610,680 A | 9/1986 | Lafleur | |
| 4,872,871 A | 10/1989 | Proxmire et al. | |
| 5,074,854 A | 12/1991 | Davis | |
| H1420 H | 2/1995 | Richardson | |
| 5,575,784 A | 11/1996 | Ames-ooten et al. | |

(Continued)

FOREIGN PATENT DOCUMENTS

| | | |
|---|---|---|
| DE | 19813334 A1 | 9/1999 |
| DE | 20220237 U1 | 3/2003 |

(Continued)

OTHER PUBLICATIONS

16638 PCT Search Report and Written Opinion for PCT/US2024/058312 dated Feb. 28, 2025, 11 pages.

(Continued)

*Primary Examiner* — Michael A Tolin
*Assistant Examiner* — Christopher C Caillouet
(74) *Attorney, Agent, or Firm* — Charles R. Matson

(57) ABSTRACT

The present disclosure relates to methods and apparatuses for making absorbent articles having front and/or back waist regions including one or more frangible pathways and at least one line accessibility opening. Methods and apparatuses may be configured to displace portions of substrates when making absorbent articles to break bond regions.

33 Claims, 43 Drawing Sheets

(56) References Cited

U.S. PATENT DOCUMENTS 5,624,420 A 4/1997 Bridges et al.
5,766,389 A 6/1998 Brandon et al.
5,897,546 A 4/1999 Kido et al.
6,027,484 A 2/2000 Romare
6,113,717 A 9/2000 Vogt et al.
6,287,287 B1 9/2001 Elsberg
6,497,695 B1 12/2002 Bruemmer-prestley et al.
6,508,797 B1 1/2003 Pozniak et al.
6,508,799 B1 1/2003 Freiburger et al.
6,524,294 B1 2/2003 Hilston et al.
6,575,949 B1 6/2003 Waksmundzki et al.
6,579,275 B1 6/2003 Pozniak et al.
6,585,855 B2 7/2003 Drew et al.
6,712,922 B2 3/2004 Sorenson et al.
6,743,321 B2 6/2004 Guralski
6,752,796 B2 6/2004 Karami
6,783,487 B2 8/2004 Duhm et al.
6,838,040 B2 1/2005 Mlinar et al.
6,976,978 B2 12/2005 Ruman et al.
6,991,696 B2 1/2006 Wagner et al.
7,077,834 B2 7/2006 Bishop et al.
7,150,730 B2 12/2006 Hasler et al.
7,156,833 B2 1/2007 Couture-dorschner
7,250,549 B2 7/2007 Richlen et al.
7,297,139 B2 11/2007 Price et al.
7,393,429 B2 7/2008 Tachibana
7,473,818 B2 1/2009 Datta et al.
7,497,852 B2 3/2009 Kawakami
7,527,617 B2 5/2009 Shimada et al.
7,608,068 B2 10/2009 Fujioka
7,621,901 B2 11/2009 Karami
7,637,898 B2 12/2009 Kuen et al.
7,641,641 B2 1/2010 Ramshak
7,686,795 B2 3/2010 Ichikawa et al.
7,708,857 B2 5/2010 Ukegawa
7,789,868 B2 9/2010 Tachibana
8,002,761 B2 8/2011 Utsunomiya et al.
8,007,622 B2 8/2011 Heller
8,034,039 B2 10/2011 Nakaoka et al.
8,043,274 B2 10/2011 Mlinar et al.
8,066,684 B2 11/2011 Fujioka
8,066,687 B2 11/2011 Ashton et al.
8,118,799 B2 2/2012 Datta et al.
8,162,912 B2 4/2012 Schlinz et al.
8,192,417 B2 6/2012 Kusumi et al.
8,216,200 B2 7/2012 Meetz et al.
8,277,430 B2 10/2012 Tabor et al.
8,361,048 B2 1/2013 Kuen
8,388,595 B2 3/2013 Van Gompel et al.
8,557,068 B2 10/2013 Ito et al.
8,569,571 B2 10/2013 Kline et al.
8,657,802 B2 2/2014 Roe et al.
8,663,184 B2 3/2014 Liu et al.
8,753,466 B2 6/2014 Thorson
8,771,449 B2 7/2014 Takino et al.
8,945,324 B2 2/2015 Hahn et al.
9,011,406 B2 4/2015 Torigoshi et al.
9,028,462 B2 5/2015 Poole et al.
9,050,217 B2 6/2015 Gassner et al.
9,060,905 B2 6/2015 Wang et al.
9,066,832 B2 6/2015 Gassner et al.
9,066,833 B2 6/2015 Gassner
9,072,632 B2 7/2015 Lavon
9,089,458 B2 7/2015 Faulks et al.
9,138,361 B2 9/2015 Faulks et al.
9,173,781 B2 11/2015 Otsubo et al.
9,226,861 B2 1/2016 Lavon
9,561,138 B2 2/2017 Mukai et al.
9,668,925 B2 6/2017 Mukai et al.
9,750,647 B2 9/2017 Umebayashi
9,789,010 B2 10/2017 Long et al.
9,820,536 B2 11/2017 Sakaguchi et al.
10,034,801 B2 7/2018 Seitz et al.
10,123,914 B2 11/2018 Kobayashi et al.
10,188,560 B2 1/2019 Mueller et al.
10,292,874 B2 5/2019 Wade et al.
10,687,988 B2 6/2020 Morimoto et al.
10,736,795 B2 8/2020 Bianchi et al.
10,799,398 B2 10/2020 Eimann et al.
10,905,602 B2 2/2021 Olsson
10,993,844 B2 5/2021 Olsson et al.
11,246,767 B2 2/2022 Roszkowiak et al.
11,304,859 B2 4/2022 Jeon et al.
11,426,312 B2 8/2022 Collins et al.
11,672,708 B2 6/2023 Johnson et al.
11,752,045 B2 9/2023 Johnson et al.
11,883,268 B2 1/2024 Johnson et al.
12,310,827 B2 5/2025 Johnson et al.
2002/0032427 A1 3/2002 Schmitz et al.
2002/0065503 A1 5/2002 Guidotti
2002/0148557 A1 10/2002 Heller
2003/0055389 A1 3/2003 Sanders et al.
2003/0088223 A1 5/2003 Vogt et al.
2003/0130641 A1 7/2003 Richlen et al.
2003/0220626 A1 11/2003 Karami
2004/0182502 A1 9/2004 Wagner et al.
2004/0186451 A1 9/2004 Bishop et al.
2004/0193135 A1 9/2004 Van Gompel
2005/0148974 A1 7/2005 Datta et al.
2005/0177125 A1 8/2005 Kondo
2005/0192553 A1 9/2005 Hasler et al.
2006/0129119 A1 6/2006 Kistler
2006/0135936 A1 6/2006 Markovich et al.
2006/0293639 A1 12/2006 Van Gompel et al.
2008/0015534 A1 1/2008 Kusumi et al.
2008/0103470 A1 5/2008 Samuelsson et al.
2008/0114322 A1 5/2008 Schmoker et al.
2008/0134487 A1 6/2008 Hartono
2008/0154223 A1 6/2008 Fujioka
2008/0249493 A1 10/2008 Kobayashi et al.
2009/0149827 A1 6/2009 Mlinar et al.
2009/0312734 A1 12/2009 Lavon et al.
2011/0098668 A1 4/2011 Thorson
2011/0155304 A1 6/2011 Sakaguchi
2013/0012905 A1 1/2013 Katsuragawa et al.
2013/0231625 A1 9/2013 Ellefson et al.
2013/0306226 A1 11/2013 Zink
2014/0110037 A1 4/2014 Verboomen
2014/0113792 A1 4/2014 Verboomen et al.
2014/0114272 A1 4/2014 Schoon et al.
2014/0135730 A1 5/2014 Mlinar et al.
2014/0155855 A1 6/2014 Romzek et al.
2014/0187405 A1 7/2014 Volp et al.
2017/0105883 A1 4/2017 Nishikawa et al.
2017/0266941 A1 9/2017 Eimann
2019/0099304 A1 4/2019 Berry
2019/0209392 A1 7/2019 Johnson et al.
2020/0163810 A1 5/2020 Johnson et al.
2021/0093485 A1 4/2021 Ljungberg et al.
2021/0369510 A1 12/2021 Ljungberg et al.
2022/0211552 A1* 7/2022 Dyer ................. A61F 13/15593
2023/0127980 A1 4/2023 Umebayashi
2023/0146261 A1 5/2023 Seitz et al.
2024/0000619 A1 1/2024 Schneider
2024/0000624 A1 1/2024 Raycheck
2024/0000625 A1 1/2024 Willhaus
2024/0000626 A1 1/2024 Willhaus
2024/0000627 A1 1/2024 Willhaus
2024/0000630 A1 1/2024 Willhaus
2024/0000631 A1 1/2024 Raycheck
2024/0000632 A1 1/2024 Willhaus
2024/0000633 A1 1/2024 Raycheck
2024/0000635 A1 1/2024 Rosiak
2024/0000637 A1 1/2024 Taylor
2024/0000638 A1 1/2024 Xu
2024/0173175 A1 5/2024 Johnson et al.

FOREIGN PATENT DOCUMENTS

EP 0570980 B1 7/1997
EP 0705088 B1 5/1999
EP 1027874 A2 8/2000
EP 0955976 B1 3/2002
EP 1128790 B1 5/2003

(56) References Cited

FOREIGN PATENT DOCUMENTS

| | | | |
|---|---|---|---|
| EP | 1779827 | A1 | 5/2007 |
| EP | 2486905 | B1 | 4/2017 |
| EP | 3053562 | B1 | 3/2022 |
| JP | 3209377 | B2 | 9/2001 |
| JP | 2001258938 | A | 9/2001 |
| JP | 2002017778 | A | 1/2002 |
| JP | 3429383 | B2 | 7/2003 |
| JP | 2003290286 | A | 10/2003 |
| JP | 3578802 | B2 | 7/2004 |
| JP | 2004329590 | A | 11/2004 |
| JP | 2005287982 | A | 10/2005 |
| JP | 3737709 | B2 | 11/2005 |
| JP | 2006034402 | A | 2/2006 |
| JP | 2006055343 | A | 3/2006 |
| JP | 2006068211 | A | 3/2006 |
| JP | 2006204385 | A | 8/2006 |
| JP | 4037216 | B2 | 11/2007 |
| JP | 4090913 | B2 | 3/2008 |
| JP | 4131683 | B2 | 6/2008 |
| JP | 2008142345 | A | 6/2008 |
| JP | 4163144 | B2 | 8/2008 |
| JP | 2008302138 | A | 12/2008 |
| JP | 4240464 | B2 | 1/2009 |
| JP | 4260711 | B2 | 2/2009 |
| JP | 4276556 | B2 | 3/2009 |
| JP | 4280187 | B2 | 3/2009 |
| JP | 4312084 | B2 | 5/2009 |
| JP | 4444078 | B2 | 1/2010 |
| JP | 4444079 | B2 | 1/2010 |
| JP | 4502882 | B2 | 4/2010 |
| JP | 4508892 | B2 | 5/2010 |
| JP | 4511284 | B2 | 5/2010 |
| JP | 2010136787 | A | 6/2010 |
| JP | 2010246901 | A | 11/2010 |
| JP | 4672651 | B2 | 1/2011 |
| JP | 4682085 | B2 | 2/2011 |
| JP | 4745119 | B2 | 5/2011 |
| JP | 4758821 | B2 | 6/2011 |
| JP | 4801498 | B2 | 8/2011 |
| JP | 4908255 | B2 | 1/2012 |
| JP | 4926742 | B2 | 2/2012 |
| JP | 5009040 | B2 | 6/2012 |
| JP | 5014452 | B2 | 8/2012 |
| JP | 5106253 | B2 | 10/2012 |
| JP | 5107447 | B2 | 10/2012 |
| JP | 5241457 | B2 | 4/2013 |
| JP | 5244226 | B2 | 4/2013 |
| JP | 5352408 | B2 | 8/2013 |
| JP | 5438952 | B2 | 12/2013 |
| JP | 5568369 | B2 | 6/2014 |
| JP | 5572822 | B2 | 7/2014 |
| JP | 5632346 | B2 | 10/2014 |
| JP | 5632521 | B2 | 10/2014 |
| JP | 5638305 | B2 | 10/2014 |
| JP | 5728907 | B2 | 4/2015 |
| JP | 5868105 | B2 | 1/2016 |
| JP | 6024486 | B2 | 11/2016 |
| JP | 6159109 | B2 | 6/2017 |
| JP | 6176958 | B2 | 7/2017 |
| JP | 6180025 | B2 | 7/2017 |
| JP | 6298274 | B2 | 3/2018 |
| JP | 2018139718 | A | 9/2018 |
| JP | 6429710 | B2 | 11/2018 |
| JP | 2018187217 | A | 11/2018 |
| JP | 6913131 | B2 | 7/2021 |
| JP | 6941026 | B2 | 9/2021 |
| JP | 2023042747 | A | 3/2023 |
| JP | 7315360 | B2 | 7/2023 |
| WO | 2009084643 | A1 | 7/2009 |
| WO | 2014080795 | A1 | 5/2014 |
| WO | 2014196215 | A1 | 12/2014 |
| WO | 2015046632 | A1 | 4/2015 |
| WO | 2016013662 | A1 | 1/2016 |
| WO | 2016104753 | A1 | 6/2016 |
| WO | 2016121236 | A1 | 8/2016 |
| WO | 2018207512 | A1 | 11/2018 |
| WO | 2020062132 | A1 | 4/2020 |
| WO | 2020195099 | A1 | 10/2020 |
| WO | 2021241553 | A1 | 12/2021 |
| WO | 2022004727 | A1 | 1/2022 |

OTHER PUBLICATIONS

All Office Actions; U.S. Appl. No. 18/214,548, filed on Jun. 27, 2023; See Patent Center.
All Office Actions; U.S. Appl. No. 18/214,564, filed on Jun. 27, 2023; See Patent Center.
All Office Actions; U.S. Appl. No. 18/214,569, filed on Jun. 27, 2023; See Patent Center.
All Office Actions; U.S. Appl. No. 18/214,573, filed on Jun. 27, 2023; See Patent Center.
All Office Actions; U.S. Appl. No. 18/214,586, filed on Jun. 27, 2023; See Patent Center.
All Office Actions; U.S. Appl. No. 18/214,603, filed on Jun. 27, 2023; See Patent Center.
All Office Actions; U.S. Appl. No. 18/214,680, filed on Jun. 27, 2023; See Patent Center.
All Office Actions; U.S. Appl. No. 18/214,718, filed on Jun. 27, 2023; See Patent Center.
All Office Actions; U.S. Appl. No. 18/214,750, filed on Jun. 27, 2023; See Patent Center.
All Office Actions; U.S. Appl. No. 18/342,054, filed on Jun. 27, 2023; See Patent Center.
All Office Actions; U.S. Appl. No. 18/342,058, filed on Jun. 27, 2023; See Patent Center.
All Office Actions; U.S. Appl. No. 18/967,768, filed on Dec. 4, 2024; See Patent Center.
All Office Actions; U.S. Appl. No. 18/967,824, filed on Dec. 4, 2024; See Patent Center.
All Office Actions; U.S. Appl. No. 18/968,031, filed on Dec. 4, 2024; See Patent Center.
All Office Actions; U.S. Appl. No. 18/978,059, filed on Dec. 12, 2024; See Patent Center.
All Office Actions; U.S. Appl. No. 18/214,626, filed on Jun. 27, 2023; See Patent Center.
Unpublished U.S. Appl. No. 18/967,768, filed on Dec. 4, 2024, Keith Richard Willhaus et al. See Patent Center.
Unpublished U.S. Appl. No. 18/967,824, filed on Dec. 4, 2024, Jeffry Rosiak et al. See Patent Center.
Unpublished U.S. Appl. No. 18/968,031, filed on Dec. 4, 2024, Keith Richard Willhaus et al. See Patent Center.
Unpublished U.S. Appl. No. 18/978,059, filed on Dec. 12, 2024, Jeromy Thomas Raycheck et al. See Patent Center.
All Office Actions; U.S. Appl. No. 19/737,113, filed on Jul. 10, 2026; See Patent Center.
U.S. Unpublished U.S. Appl. No. 19/737,113, filed on Jul. 10, 2026, to Kaitlyn Nicole Taylor et. al.; See Patent Center.

* cited by examiner

Figure 3A1

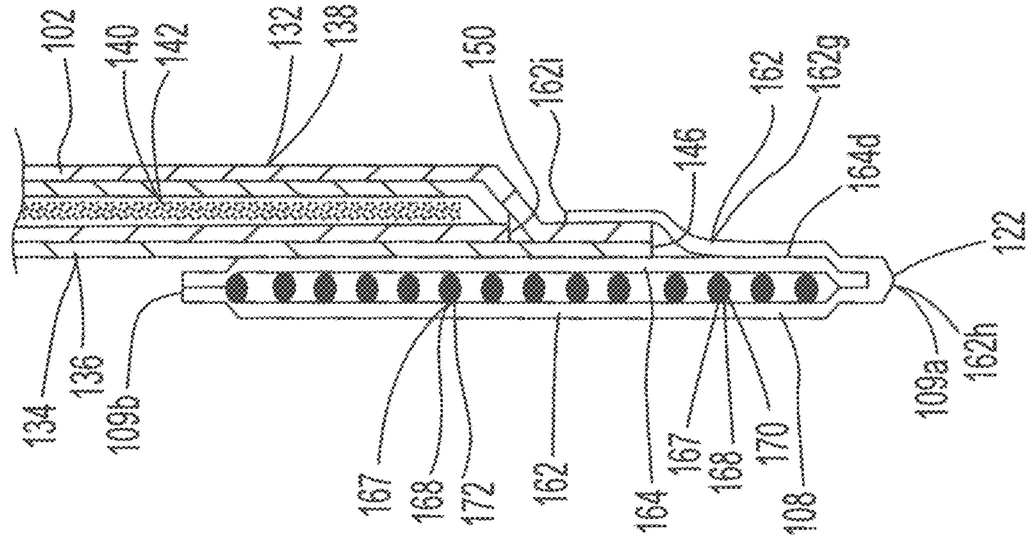
Figure 3B
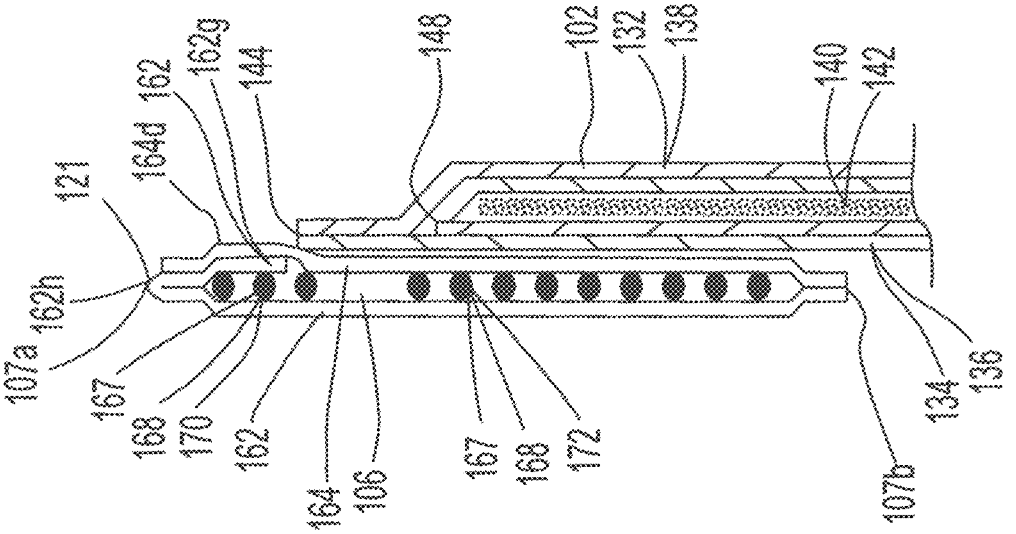
Figure 3A2

METHOD AND APPARATUS FOR BREAKING BOND REGIONS IN ABSORBENT ARTICLES WITH FRANGIBLE PATHWAYS

CROSS REFERENCE TO RELATED APPLICATION

This application claims the benefit of U.S. Provisional Application No. 63/610,082, filed Dec. 14, 2023, which is incorporated by reference herein in its entirety.

FIELD

The present disclosure relates to methods and apparatuses for making absorbent articles, and more particularly, to making absorbent articles having front and/or back waist regions including one or more frangible pathways with at least one line accessibility opening.

BACKGROUND

Some absorbent articles have components that include elastomeric laminates. Such elastomeric laminates may include an elastic material bonded to one or more nonwovens. The elastic material may include an elastic film and/or elastic strands. In some laminates, a plurality of elastic strands are joined to a nonwoven while the plurality of strands are in a stretched condition so that when the elastic strands relax, the nonwoven gathers, and in turn, forms corrugations and rugosities. The resulting elastomeric laminate is stretchable to the extent that the corrugations allow the elastic strands to elongate.

Absorbent articles in the form of diaper pants may also be configured with an absorbent chassis connected with front and back elastic belts, wherein opposing end regions of the front and back belts are connected with each other at side seams. In some instances, the elasticity of the front and back belts is removed in regions where the chassis connects with the belts. Thus, in some converting configurations adapted to assemble such diaper pants, stretched elastic strands are glued between two continuous nonwoven webs to form an elastic laminate. Regions of the elastic strands may then be intermittently deactivated along the length of the elastic laminate by cutting the elastic strands in areas to be connected with the chassis, sometimes referred to as tummy elastic cutting.

Some caregivers of older incontinent babies or toddlers may prefer a closed, pant-style disposable absorbent article to enable application to, and removal from, a child while the child is in a standing position. One disadvantage of this product form is that the removal and disposal of feces-containing products may be unhygienic and inconvenient. For example, pulling the product down could cause feces to smear down the legs of a wearer. In other examples, a caregiver may tear open the bonded sides using force. In turn, the force used can lead to a rapid release of energy from the diaper, causing the caregiver to lose control of the product and allowing feces to spill out. In contrast, removal and disposal of traditional open or taped diaper forms with fasteners may be readily accomplished while the child is laying on their back. In this case, the fasteners are opened, the diaper is removed from under the child, rolled into a roughly cylindrical shape, and then the fasteners are secured around the rolled, soiled diaper, closing the leg openings for hygienic disposal.

In order to avoid having to remove soiled diaper pants from a wearer by sliding the soiled diaper pant down the wearer's legs or tearing bonded side seams, some diaper pants may be configured with tear lines in the front belt or back belt. Such tear lines may include perforations that allow a caregiver to more easily separate the belt along the perforation lines. Once the belt is separated, the diaper pant can be more easily removed from the wearer without having to slide the diaper pant down the wearer's legs, in a similar manner as a traditional open taped diaper form.

Some perforation configurations may include openings in the belt to provide a location for user to initiate tearing of the belt. However, some cutting systems, such as knife rolls, may create openings and/or perforations that are not fully formed cut lines. Instead of creating fully formed cut lines, such knife rolls may create bonded regions. In turn, such bonded regions may increase the difficultly for a user to insert fingers into the belt in order to initiate the tearing process.

Consequently, it would be beneficial to create pant-style articles that provide the caregiver the ability to remove and dispose soiled products in a similar manner to traditional open diaper forms. In addition, it would be beneficial to provide diaper pants with frangible pathways configured with lines of weakness and accessibility openings having fully formed cut lines.

SUMMARY

In one form, a method for assembling absorbent articles comprises steps of: providing a substrate comprising a first edge separated from a second edge in a cross direction; advancing the substrate in a machine direction; forming a bond region in the substrate, the bond region comprising a leading edge and a trailing edge and comprising material of the substrate fused together extending between the leading edge region and the trailing edge region; forming a frangible pathway in the substrate extending between the bond region and the first edge of the substrate; breaking the bond region to form a slit through the substrate between the leading edge region and the trailing edge region by displacing the bond region in a Z-direction that is normal to the machine direction and the cross direction relative to the first side edge and the second side edge of the substrate; and providing a chassis comprising a topsheet, a backsheet, and an absorbent core positioned between the topsheet and the backsheet; and bonding a portion of the chassis with the substrate to define a chassis overlap region.

BRIEF DESCRIPTION OF THE DRAWINGS

FIG. 3A1 is a cross-sectional detailed view of another example configuration wherein the first belt is provided with panel layers wherein one panel layer is folded over another panel layer.

FIG. 3A2 is a cross-sectional detailed view of another example configuration wherein the first belt is provided with panel layers wherein one panel layer is folded over another panel layer.

FIG. 3B is a cross-sectional detailed view of a second belt provided with panel layers wherein one panel layer is folded over another panel layer.

FIG. 8AA1 is a cross-sectional view of the fastener component of FIG. 8A taken along line 8AA-8AA.

FIG. 8AA2 is a cross-sectional view of the fastener component of FIG. 8A taken along line 8AA-8AA, wherein the fastener component is integrally formed from belt components.

DETAILED DESCRIPTION

Definitions

Figure 1:
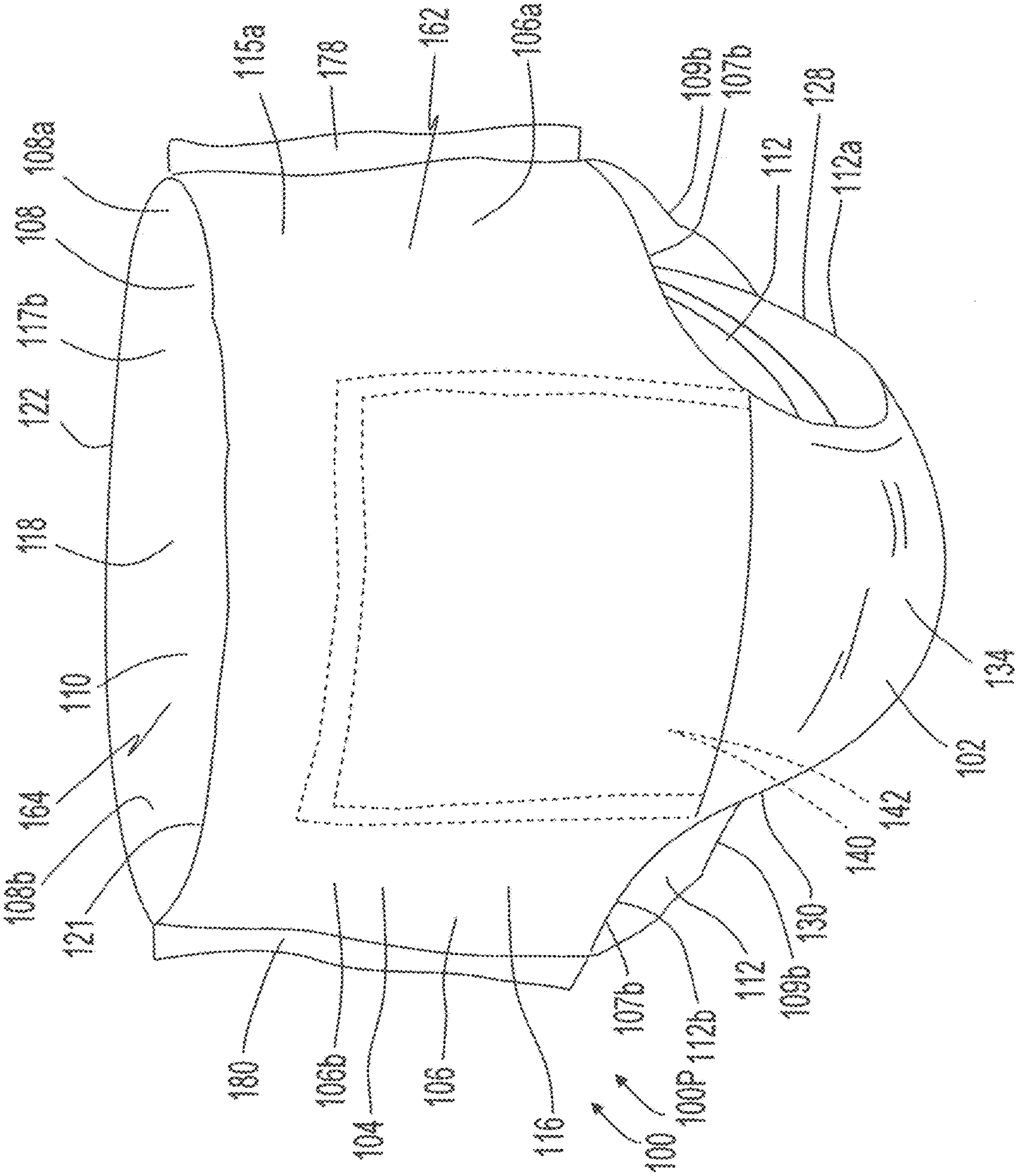
FIG. 1 shows a perspective view of a diaper pant in a pre-fastened configuration.

The following term explanations may be useful in understanding the present disclosure:

"Absorbent article" refers to devices, which absorb and contain body exudates and, more specifically, refers to devices, which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, menstrual pads and the like.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

The terms "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force. Elastomeric materials may include elastomeric films, scrims, nonwovens, ribbons, strands and other sheet-like structures.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "distal" is used to describe a position situated away from a center of a body or from a point of attachment, and the term "proximal" is used to describe a position situated nearer to a center of a body or a point of attachment.

The term "substrate" is used herein to describe a material which is primarily two-dimensional (i.e., in an XY plane) and whose thickness (in a Z direction) is relatively small (i.e., 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

"Pre-strain" refers to the strain imposed on an elastic or elastomeric material prior to combining it with another element of the elastomeric laminate or the absorbent article. Pre-strain is determined by the following equation Pre-strain=((extended length of the elastic-relaxed length of the elastic)/relaxed length of the elastic)*100.

"Decitex" also known as Dtex is a measurement used in the textile industry used for measuring yarns or filaments. 1 Decitex=1 gram per 10,000 meters. In other words, if 10,000 linear meters of a yarn or filament weights 500 grams that yarn or filament would have a decitex of 500.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, back waist fastened or seamed). Example diaper pants in various configurations are disclosed in U.S. Pat. Nos. 4,940,464; 5,092,861; 5,246,433; 5,569,234; 5,897,545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

"Closed-form" means opposing waist regions are joined, as packaged, either permanently or refastenably to form a continuous waist opening and leg openings.

"Open-form" means opposing waist regions are not initially joined to form a continuous waist opening and leg openings but comprise a closure means such as a fastening system to join the waist regions to form the waist and leg openings before or during application to a wearer of the article.

The present disclosure relates to methods of making absorbent articles including a first belt and a second belt, wherein laterally opposing end portions of the second belt are connected with laterally opposing end portions of the first belt at a first side seam and a second side seam to form a waist opening. As discussed in more detail below, a substrate in the form of an elastic laminate comprising a first edge separated from a second edge in a cross direction may be advanced in a machine direction. A bond region is formed in the substrate, wherein the bond region extends in the cross direction and comprises a leading edge region and a trailing edge region. The bond region comprises material of the substrate fused together that extends between the leading edge region and the trailing edge region. A frangible pathway is formed in the substrate extending between the bond region and the first edge of the substrate. The bond region is displaced in a Z-direction that is normal to the machine direction and the cross direction relative to the first side edge and the second side edge of the substrate. The displacement of the bond region causes the bond region to break and form a slit through the substrate between the leading edge region and the trailing edge region. In additional assembly steps, a chassis comprising a topsheet, a backsheet, and an absorbent core positioned between the topsheet and the backsheet is bonded with the substrate to define a chassis overlap region, wherein the slit and at least a portion of the frangible pathway are positioned in the chassis overlap region.

Figure 2A:
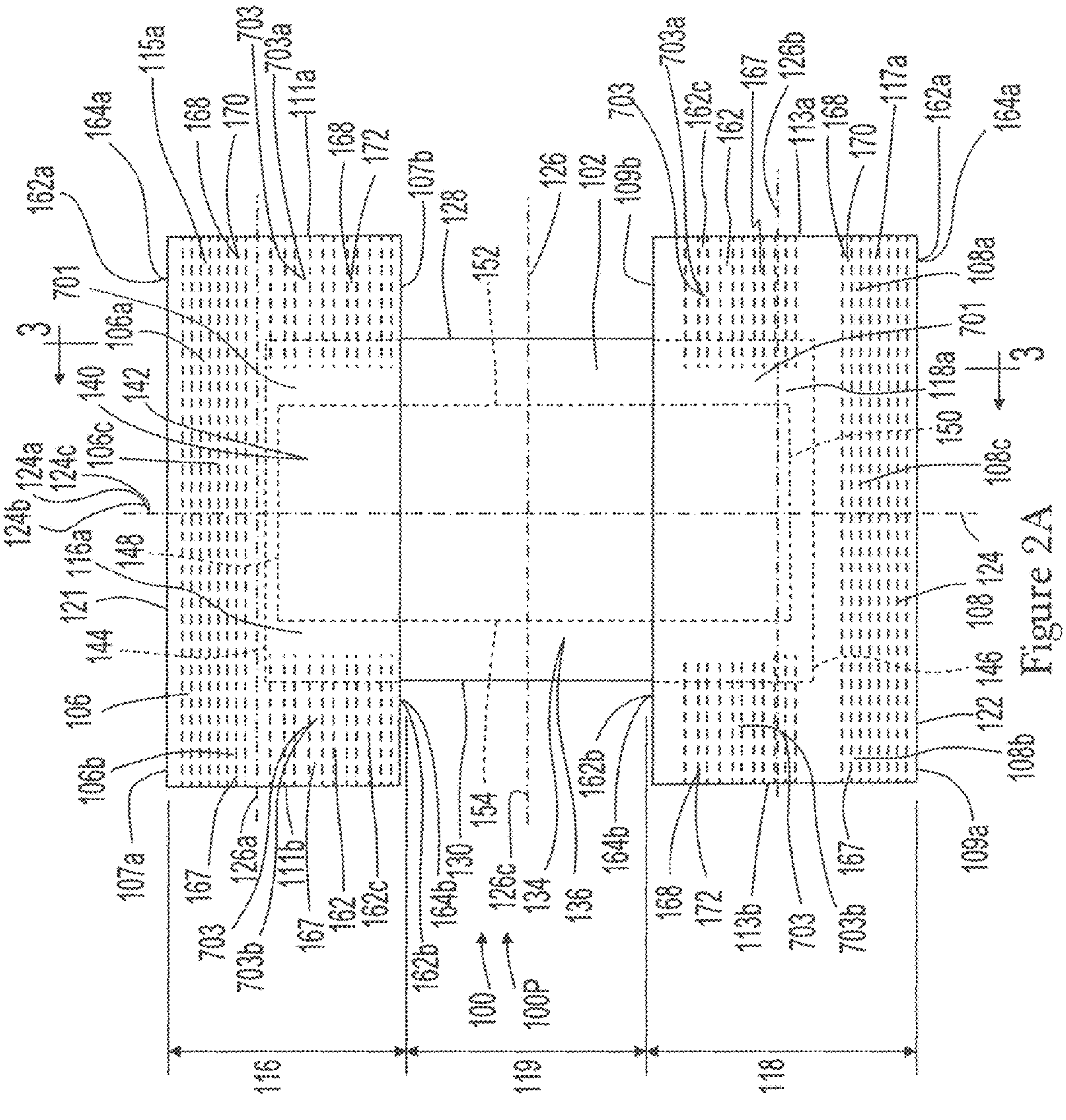
FIG. 2A shows a plan view of a diaper pant with the portion of the diaper that faces away from a wearer oriented toward the viewer.
Figure 2B:
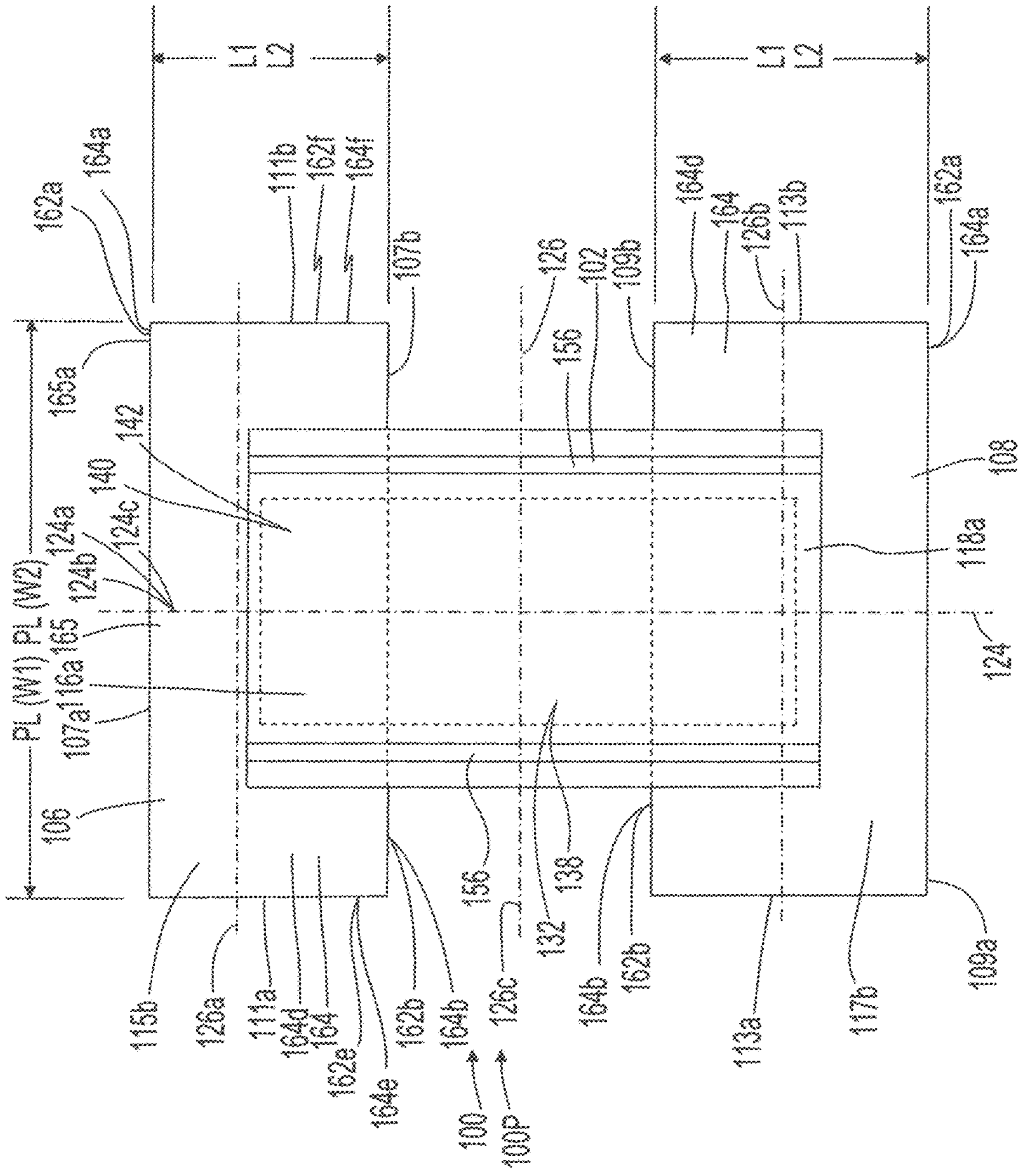
FIG. 2B shows a plan view of a diaper pant with the portion of the diaper that faces toward a wearer oriented toward the viewer.

FIGS. 1-2B show an example of an absorbent article 100 in the form of a diaper pant 100P that may include components constructed in accordance with the configurations disclosed herein. In particular, FIG. 1 shows a perspective views of a diaper pant 100P in a pre-fastened configuration. FIG. 2A shows a plan view of the diaper pant 100P with the portion of the diaper that faces away from a wearer oriented toward the viewer, and FIG. 2B shows a plan view of the diaper pant 100P with the portion of the diaper that faces toward a wearer oriented toward the viewer. The diaper pant 100P includes a chassis 102 and a ring-like elastic belt 104. As discussed below in more detail, a first elastic belt 106 and a second elastic belt 108 are bonded together to form the ring-like elastic belt 104.

With continued reference to FIGS. 1-2B, the diaper pant 100P and the chassis 102 each include a first waist region 116, a second waist region 118, and a crotch region 119 disposed intermediate the first and second waist regions. It may also be described that the chassis 102 includes a first end region 116*a*, a second end region 118*a*, and a crotch region 119 disposed intermediate the first and second end regions 116*a*, 118*a*. The first waist region 116 may be configured as a front waist region, and the second waist region 118 may be configured as back waist region. The diaper 100P may also include a laterally extending front waist edge 121 in the front waist region 116 and a longitudinally opposing and laterally extending back waist edge 122 in the back waist region 118. To provide a frame of reference for the present discussion, the diaper 100P and chassis 102 of FIGS. 2A and 2B are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a second longitudinal or left side edge 130 of the chassis 102. As previously mentioned, the longitudinal axis 124 extends perpendicularly through the front waist edge 121 and the back waist edge 122, and the lateral axis 126 extends perpendicularly to the longitudinal axis 124. When the diaper pant 100P is worn, the longitudinal direction may extend from the wearer's front waist, through the crotch, to the wearer's back waist. To provide a further frame of reference for the present discussion, the diapers 100P of FIGS. 2A, 2B, and 18B are shown wherein: the first elastic belt 106 comprises a longitudinal centerline 124*a* and lateral centerline 126*a*; the second elastic belt 108 comprises a longitudinal centerline 124*b* and lateral centerline 126*b*; and the chassis 102 comprises a longitudinal centerline 124*c* and lateral centerline 126*c*. The longitudinal centerlines 124*a*, 124*b*, 124*c* are perpendicular to the lateral center lines 126*a*, 126*b*, 126*c*.

As shown in FIGS. 1-2B, the diaper pant 100P may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100P may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 may be located longitudinally inward from the laterally extending front waist edge 121 in the front waist region 116 and the laterally extending back waist edge 122 in the back waist region 118. In some configurations, the laterally extending end edges 144 and 146 may be coterminous with or located longitudinally outward from the laterally extending front waist edge 121 in the front waist region 116 and the laterally extending back waist edge 122 in the back waist region 118. When the diaper pant 100P is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

As previously mentioned, the diaper pant 100P may include a backsheet 136. The backsheet 136 may also define the outer, garment facing surface 134 of the chassis 102. The backsheet 136 may also comprise a woven or nonwoven material, polymeric films such as thermoplastic films of polyethylene or polypropylene, and/or a multi-layer or composite materials comprising a film and a nonwoven material. The backsheet may also comprise an elastomeric film. An example backsheet 136 may be a polyethylene film having a thickness of from about 0.012 mm (0.5 mils) to about 0.051 mm (2.0 mils). Further, the backsheet 136 may permit vapors to escape from the absorbent core (i.e., the backsheet is breathable) while still preventing exudates from passing through the backsheet 136.

Also described above, the diaper pant 100P may include a topsheet 138. The topsheet 138 may also define all or part of the inner, wearer facing surface 132 of the chassis 102. The topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art. Topsheets 138 may be selected from high loft nonwoven topsheets, apertured film topsheets and apertured nonwoven topsheets. Exemplary apertured films may include those described in U.S. Pat. Nos. 5,628,097; 5,916,661; 6,545,197; and 6,107,539, all of which are incorporated by reference herein.

As mentioned above, the diaper pant 100P may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735, all of which are incorporated by reference herein.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1, all of which are incorporated by reference herein.

As previously mentioned, the diaper 100P may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730 A1, all of which are incorporated by reference herein.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1. The ring-like elastic belt may be formed by joining a first elastic belt to a second elastic belt with a permanent side seam or with an openable and reclosable fastening system disposed at or adjacent the laterally opposing sides of the belts.

As previously mentioned, the ring-like elastic belt 104 may be defined by a first elastic belt 106 connected with a second elastic belt 108. As shown in FIGS. 2A and 2B, the first elastic belt 106 extends between a first longitudinal side edge 111*a* and a second longitudinal side edge 111*b* and defines first and second opposing end regions 106*a*, 106*b* and a central region 106*c*. And the second elastic 108 belt extends between a first longitudinal side edge 113*a* and a second longitudinal side edge 113*b* and defines first and second opposing end regions 108*a*, 108*b* and a central region 108*c*. As measured in an extended state, the distance between the first longitudinal side edge 111*a* and the second longitudinal side edge 111*b* defines the pitch length, PL, of the first elastic belt 106, and the distance between the first longitudinal side edge 113*a* and the second longitudinal side edge 113*b* defines the pitch length, PL, of the second elastic belt 108. The central region 106*c* of the first elastic belt is connected with the first waist region 116 or first end region 116*a* of the chassis 102, and the central region 108*c* of the second elastic belt 108 is connected with the second waist region 118 or second end region 118*a* of the chassis 102. As shown in FIG. 1, the first end region 106*a* of the first elastic belt 106 is connected with the first end region 108*a* of the second elastic belt 108 at first side seam 178, and the second end region 106*b* of the first elastic belt 106 is connected with the second end region 108*b* of the second elastic belt 108 at second side seam 180 to define the ring-like elastic belt 104 as well as the waist opening 110 and leg openings 112. It is to be appreciated that the first belt 106 and the second belt 108 may be permanently or refastenably connected with each other at the first side seam 178 and the second side seam 180. The side seams 178, 180 may comprise a permanent bond, such as a thermal, pressure, or adhesive bond, or may be a releasable bond, such as a mechanical or cohesive fastener.

As shown in FIGS. 2A and 2B, the first elastic belt 106 also defines an outer laterally extending edge 107*a* and an inner laterally extending edge 107*b*, and the second elastic belt 108 defines an outer laterally extending edge 109*a* and an inner laterally extending edge 109*b*. The outer edge 107*a* of the first belt 106 is positioned longitudinally outward of the inner edge 107*b*, and the outer edge 109*a* of the second belt 108 is positioned longitudinally outward of the inner edge 109*b*. As such, as shown in FIG. 1, a perimeter edge 112*a* of one leg opening may be defined by portions of the inner laterally extending edge 107*b* of the first elastic belt 106, the inner laterally extending edge 109*b* of the second elastic belt 108, and the first longitudinal or right side edge 128 of the chassis 102. And a perimeter edge 112*b* of the other leg opening may be defined by portions of the inner laterally extending edge 107*b*, the inner laterally extending edge 109*b*, and the second longitudinal or left side edge 130 of the chassis 102. The outer laterally extending edges 107*a*, 109*a* may also define the front waist edge 121 and the laterally extending back waist edge 122 of the diaper pant 100P.

It is to be appreciated that the first elastic belt 106 and the second elastic belt 108 may define different sizes and shapes. In some configurations, the first elastic belt 106 and/or second elastic belt 108 may define curved contours. For example, the inner lateral edges 107*b*, 109*b* of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168 that extend along non-linear or curved paths that may correspond with the curved contours of the inner lateral edges 107*b*, 109*b*.

Figure 2C:
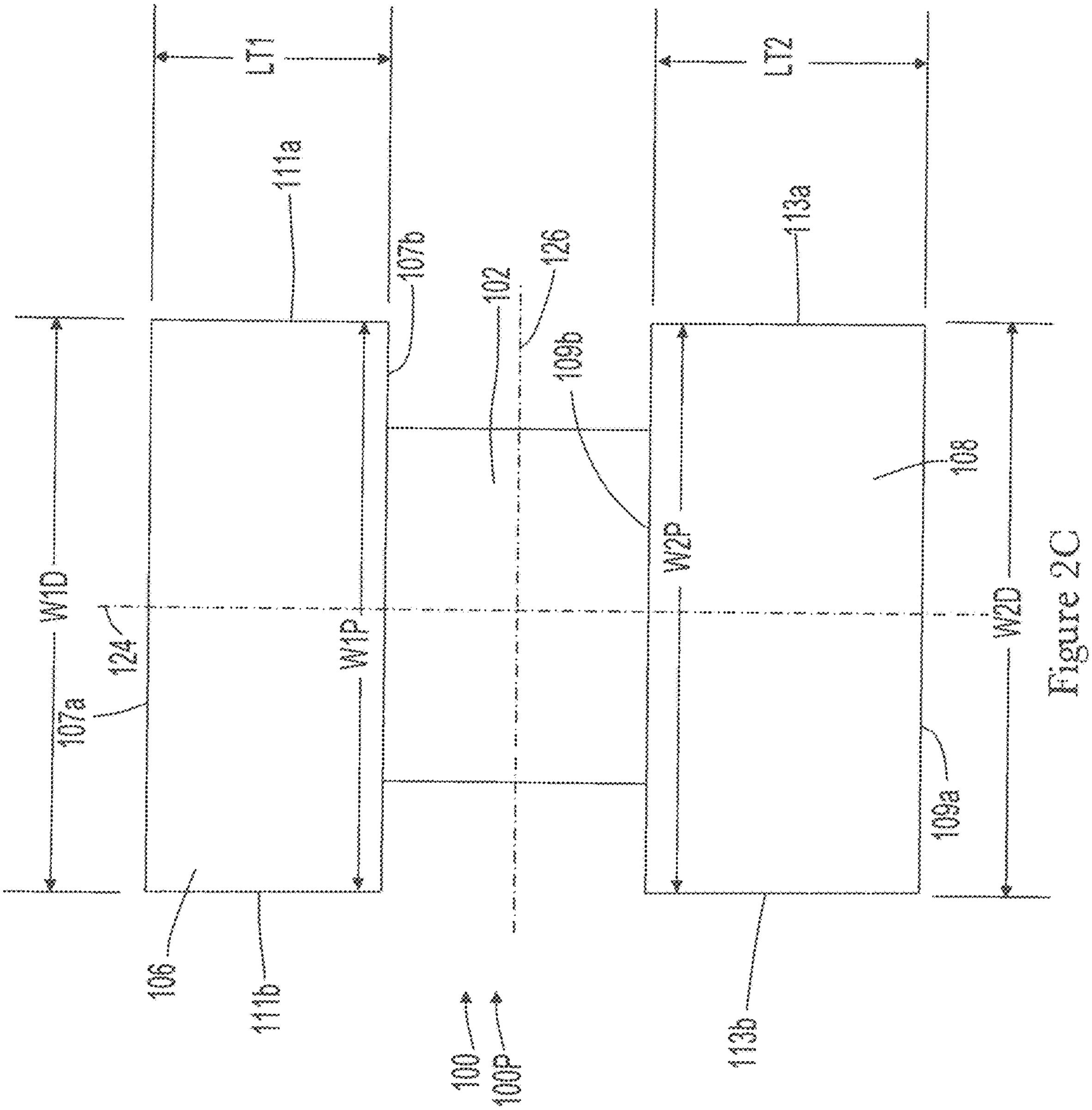
FIG. 2C shows a plan view of a diaper pant with the portion of the diaper that faces away from a wearer oriented toward the viewer, illustrating first and second belt size and shape features.

FIG. 2C shows a configuration wherein the first elastic belt 106 and the second elastic belt 108 both define generally rectangular shapes. For example, as shown in FIG. 2C, the outer laterally extending edge 107*a* of the first elastic belt 106 may comprise a lateral width of W1D and the inner laterally extending edge 107*b* may comprise a lateral width of W1P, wherein W1D and W1P are equal or substantially equal. In addition, the outer laterally extending edge 109*a* of the second elastic belt 108 may comprise a lateral width of W2D and the inner laterally extending edge 109*b* may comprise a lateral width of W2P, wherein W2D and W2P are equal or substantially equal.

Figure 2D:
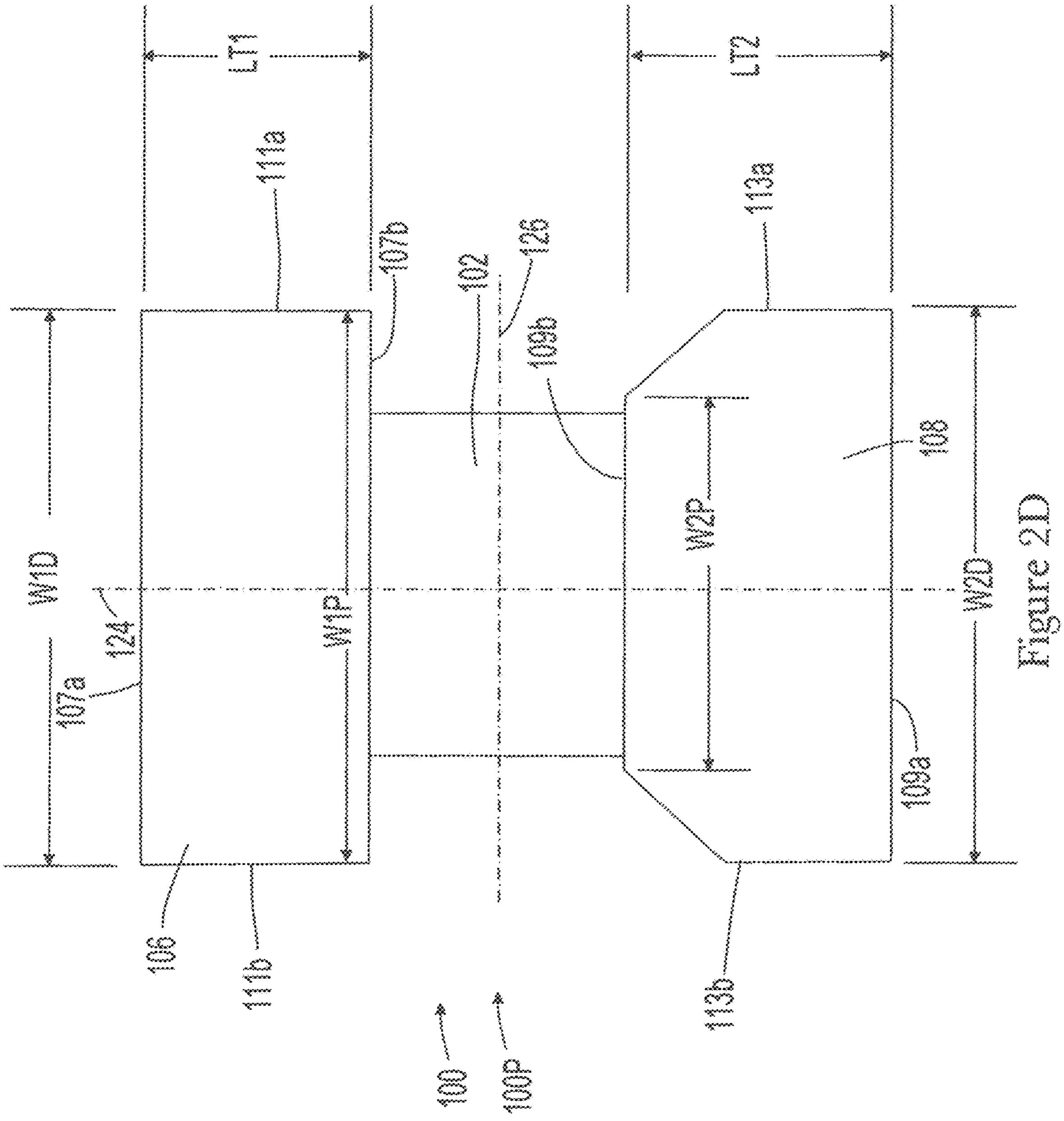
FIG. 2D shows a plan view of a diaper pant with the portion of the diaper that faces away from a wearer oriented toward the viewer, illustrating first and second belt size and shape features.

In some configurations, at least one of the first elastic belt 106 and the second elastic belt 108 may comprise lateral edges having different lengths. For example, FIG. 2D shows a configuration wherein the first elastic belt 106 defines a generally rectangular shape, such as described with reference to FIG. 2C, and wherein the outer laterally extending edge 109*a* of the second elastic belt 108 and the inner laterally extending edge 109*b* have different lengths. As shown in FIG. 2D, the outer laterally extending edge 109*a* of the second elastic belt 108 may comprise a lateral width of W2D and the inner laterally extending edge 109*b* may comprise a lateral width of W2P, wherein W2D is greater than W2P.

Figure 2E:
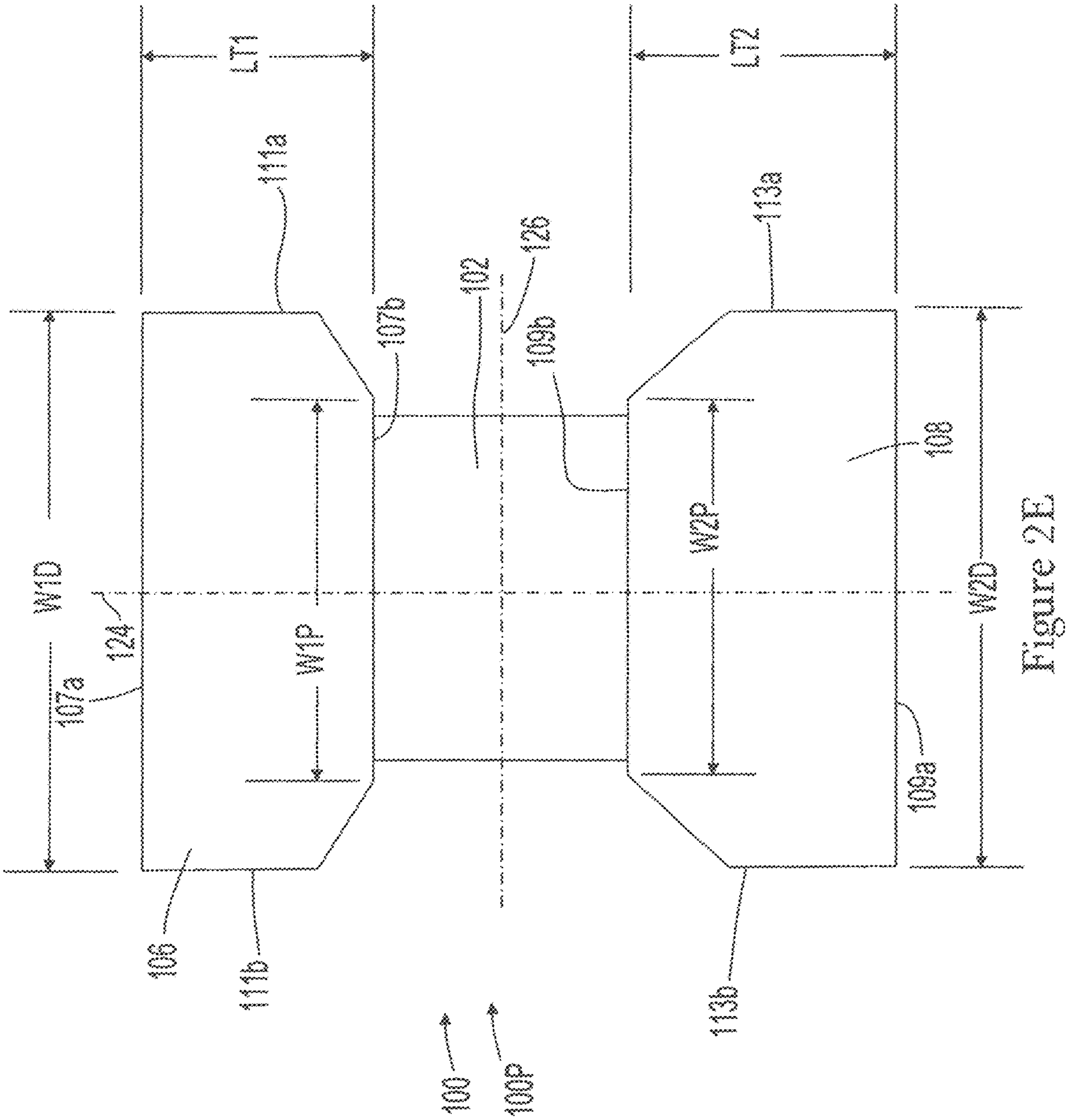
FIG. 2E shows a plan view of a diaper pant with the portion of the diaper that faces away from a wearer oriented toward the viewer, illustrating first and second belt size and shape features.

In some configurations, both the first elastic belt 106 and the second elastic belt 108 may comprise lateral edges having different lengths. For example, FIG. 2E shows a configuration wherein the outer laterally extending edge 107*a* of the first elastic belt 106 and the inner laterally extending edge 107*b* have different lengths, and wherein the outer laterally extending edge 109*a* of the second elastic belt 108 and the inner laterally extending edge 109*b* have different lengths. As shown in FIG. 2E, the outer laterally extending edge 107*a* of the first elastic belt 107 may comprise a lateral width of W1D and the inner laterally extending edge 107*b* may comprise a lateral width of W1P, wherein W1D is greater than W1P, and wherein the outer laterally extending edge 109*a* of the second elastic belt 108 may comprise a lateral width of W2D and the inner laterally extending edge 109*b* may comprise a lateral width of W2P, wherein W2D is greater than W2P.

With reference to FIGS. 2C-2E, the first elastic belt 106 may define a longitudinal length LT1 extending between outer laterally extending edge 107*a* and the inner laterally extending edge 107*b*, and the second elastic belt 108 may define a longitudinal length LT2 extending between outer laterally extending edge 109*a* and the inner laterally extending edge 109*b*. In some configurations, LT1 may be equal to LT2. In some configurations, LT1 may be less or greater than LT2. With continued reference to FIGS. 2C-2E, in some configurations, W1D may be equal to W1P, or W1D may be different than W1P. In some configurations, W2D may be equal to W2P, or W2D may be different than W2P. In some configurations, W1D and/or W1P may be equal to or different W2D and/or W2P.

Figure 3:
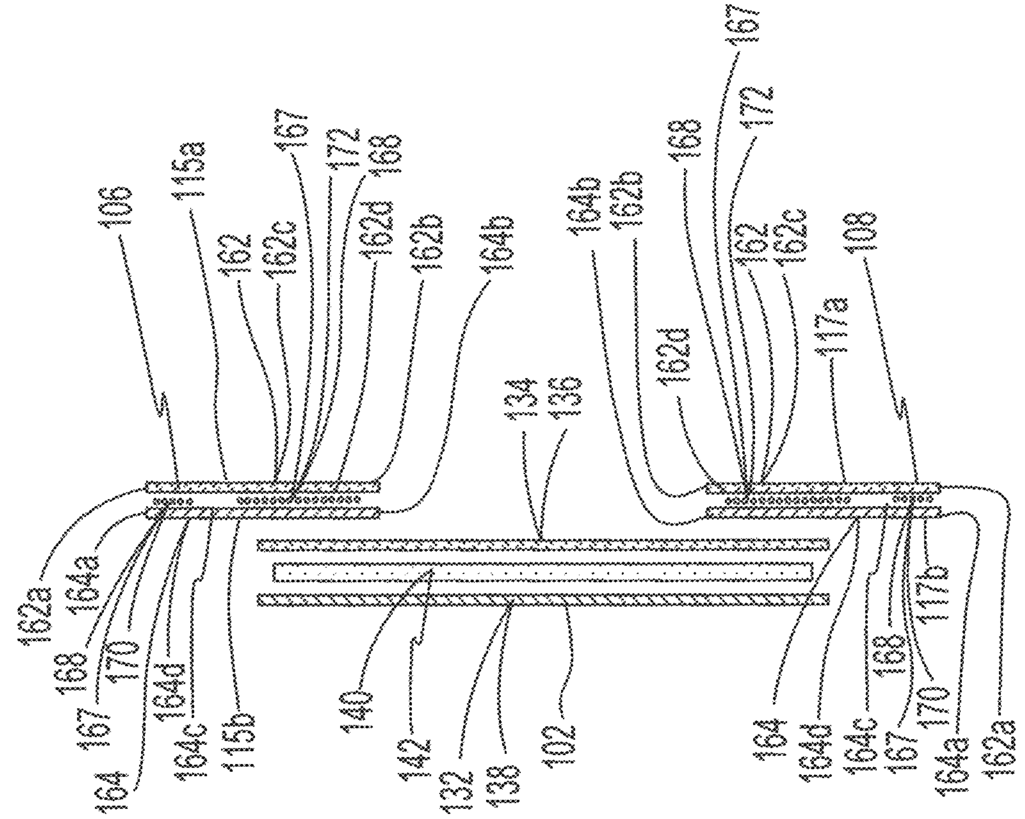
FIG. 3 is a cross-sectional view of the diaper pant of FIG. 2A taken along line 3-3 showing first and second elastic belts provided with panel layers.

With reference to FIGS. 2A, 2B, and 3, the first elastic belt 106 and the second elastic belt 108 may also each include a first substrate 162 and a second substrate 164. The first substrates 162 may be oriented to define at least a portion of a garment facing surface 115*a* of the first elastic belt 106 and a garment facing surface 117*a* the second elastic belt 108, and the second substrates 164 may be oriented to define at least a portion of a wearer facing surface 115*b* of the first elastic belt 106 and a wearer facing surface 117*b* of the second elastic belt 108. The first substrate 162 may extend from a proximal edge 162*b* to a distal edge 162*a* for a maximum length L1, and the second substrate 164 may extend from a proximal edge 164*b* to a distal edge 164*a* for a maximum length L2. It is to be appreciated that the distal edge 162*a* and/or the proximal edge 162*b* of the first substrate 162 may be straight and/or curved and/or may be parallel or unparallel to each other. It is also to be appreciated that the distal edge 164*a* and/or the proximal edge 164*b* of the second substrate 164 may be straight and/or curved and/or may be parallel or unparallel to each other. As such, the maximum length L1 refers to the longest distance extending longitudinally between the distal edge 162*a* and the proximal edge 162*b* of the first substrate 162, and the maximum length L2 refers to the longest distance extending longitudinally between the distal edge 164*a* and the proximal edge 164*b* of the second substrate 164. In some configurations, L1 may be equal to, less than, or greater than L2. In some configurations, L1 may be equal to or less than LT1, and L2 may be equal to or less than LT2. In some configurations, the distal edge 162*a* of the first substrate 162 may define at least a portion of the front waist edge 121 and/or at least a portion of back waist edge 122, and/or the distal edge 164*a* of the second substrate 164 may define at least a portion of the front waist edge 121 and/or at least a portion of back waist edge 122. As such, in some configurations, the distal edge 162*a* of the first substrate 162 and/or the distal edge 164*a* of the second substrate 164 may define at least a portion of the waist opening 110.

Figure 1A:
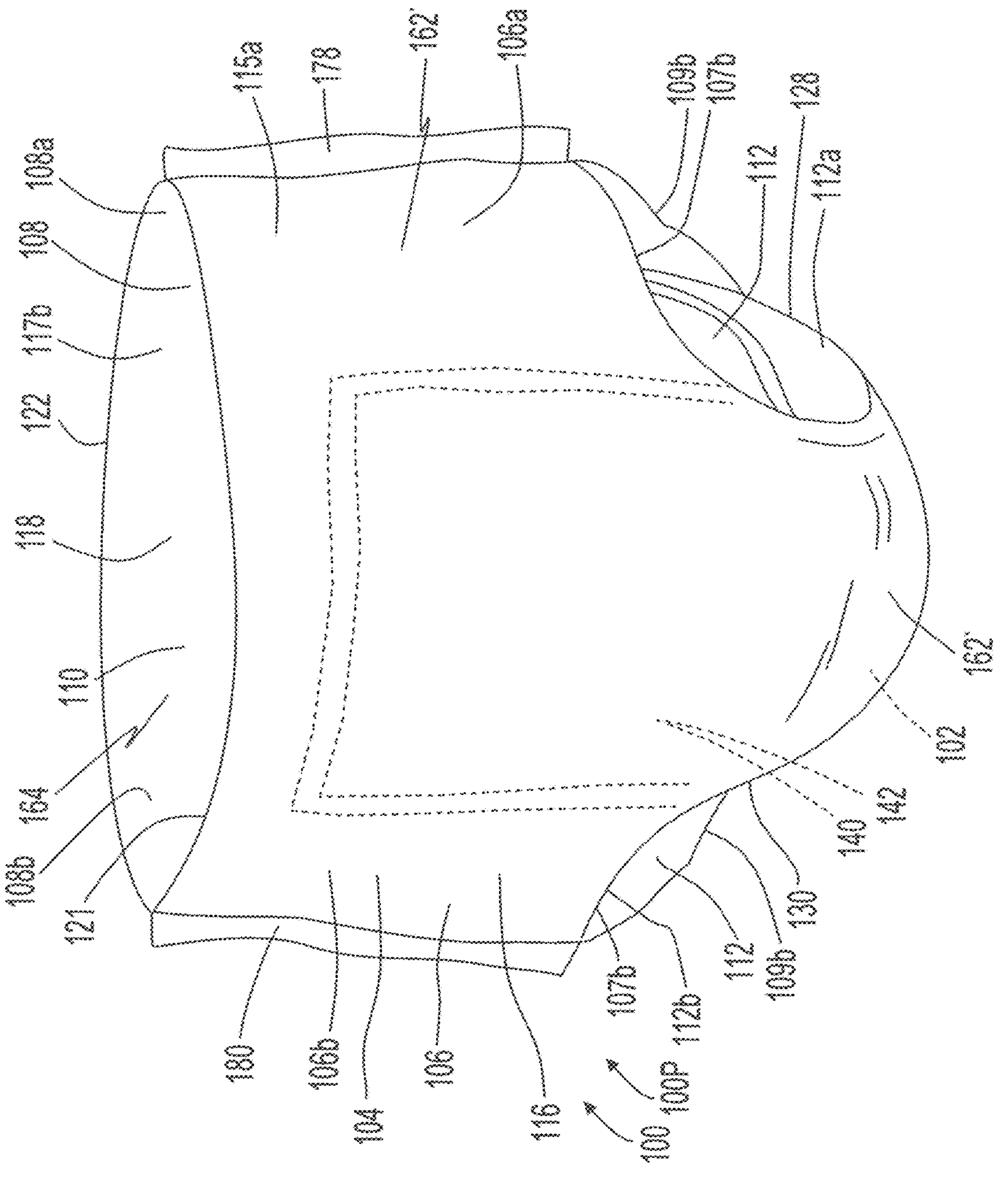
FIG. 1A shows a perspective view of a diaper pant with a continuous outer cover in a pre-fastened configuration.
Figure 2F:
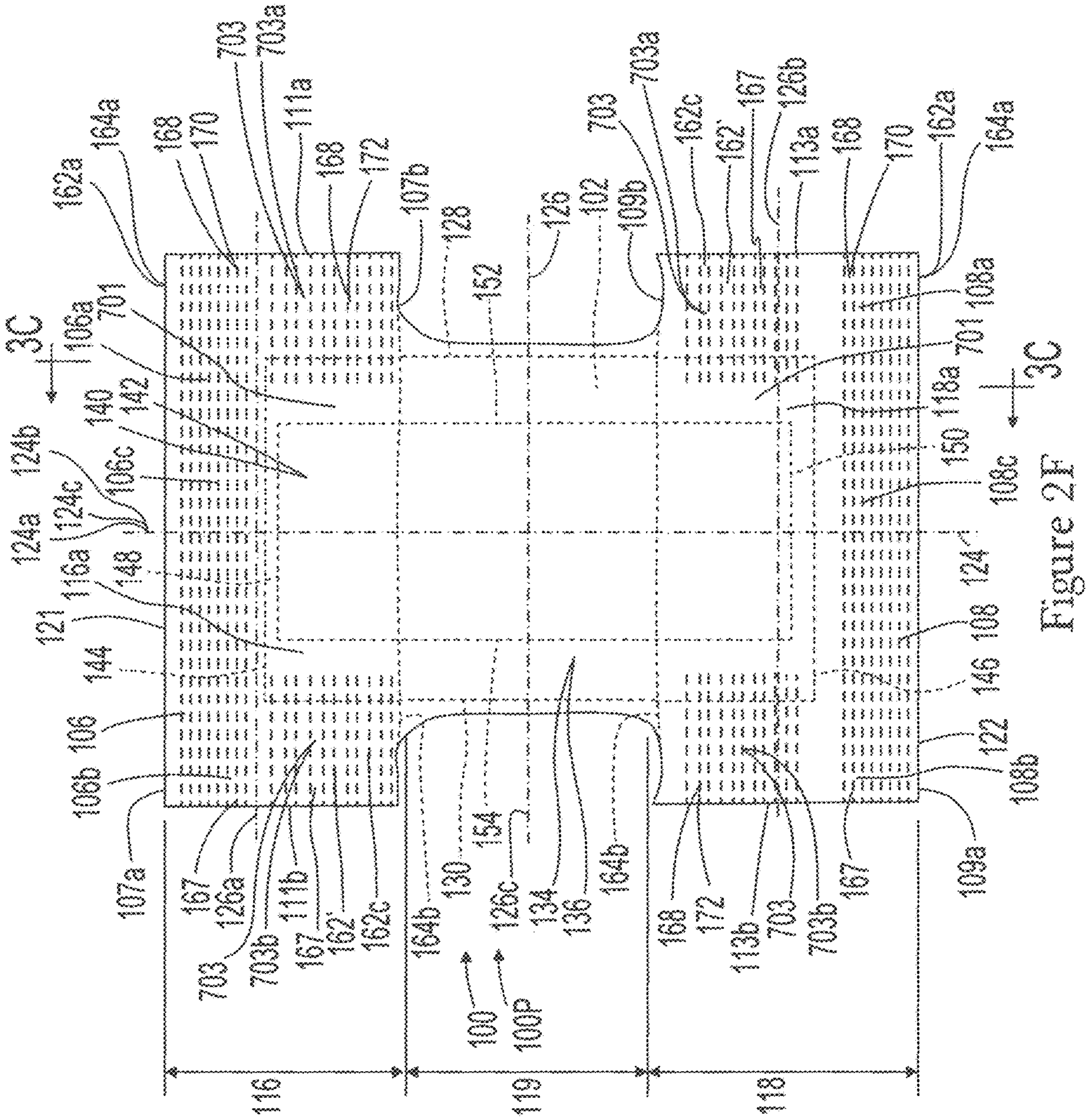
FIG. 2F shows a plan view of a diaper pant with a continuous outer cover with the portion of the diaper that faces away from a wearer oriented toward the viewer.
Figure 3A:
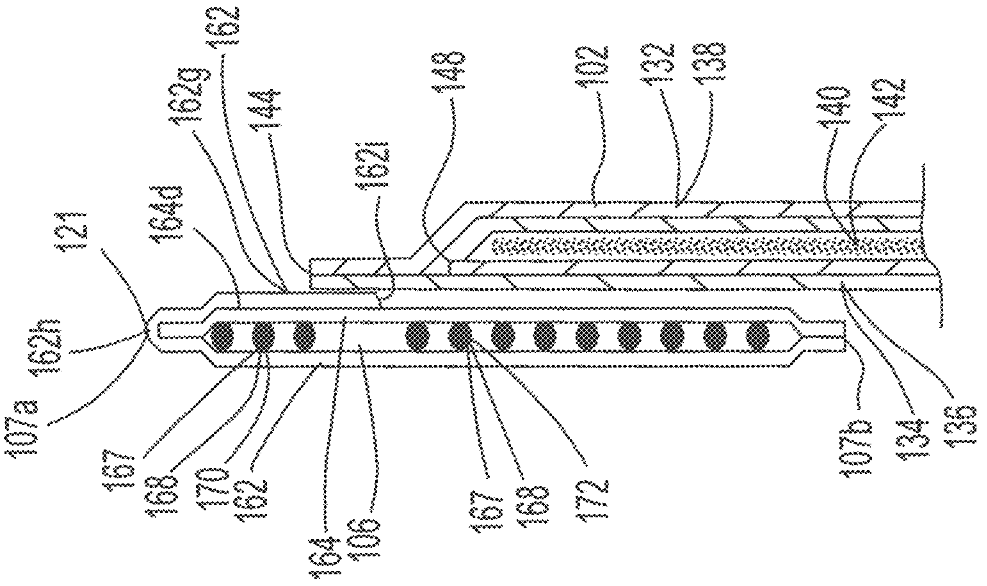
FIG. 3A is a cross-sectional detailed view of a first belt provided with panel layers wherein one panel layer is folded over another panel layer.
Figure 3A:
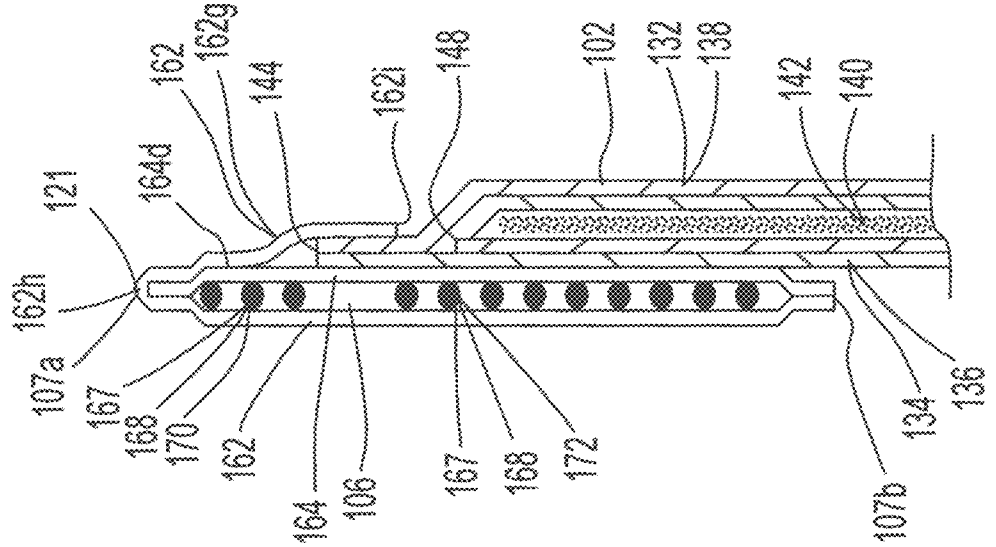
Figure 3C:
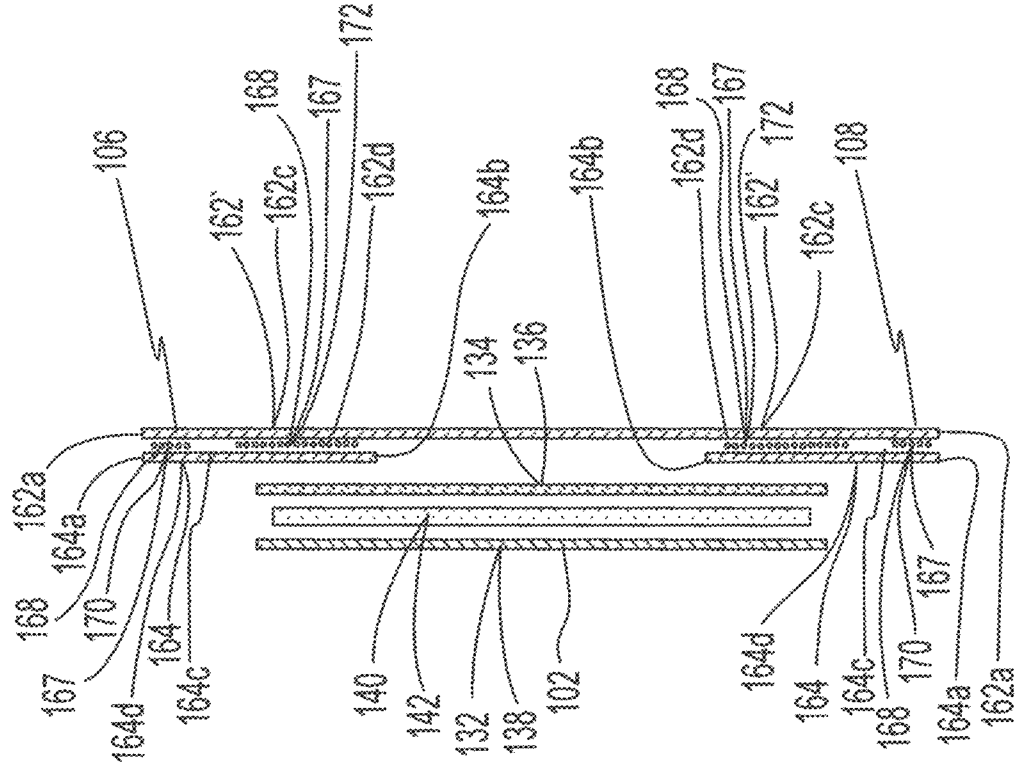
FIG. 3C is a cross-sectional view of the diaper pant of FIG. 2F taken along line 3C-3C showing first and second elastic belts provided with panel layers and a continuous outer cover.

It is also to be appreciated that the first substrate 162 and/or the second substrate 164 may extend continuously from the first belt 106 to the second belt 108. For example, the first substrate 162 may be configured to define a continuous outer cover 162' that extends contiguously from the first waist edge 121 to the second waist edge 122, such as shown in FIGS. 1A, 2F, and 3C. It is also to be appreciated that diaper pants 100P with continuous outer covers, such as shown in FIGS. 1A, 2F, and 3C may also be configured to include various aspects of the frangible pathways and fastener components discussed herein.

It is to be appreciated that the first substrate 162 and the second substrate 164 may define various lateral widths that may or may not be equal. For example, as shown in FIG. 2B, the first substrate 162 may extend laterally between a first longitudinal edge 162*e* and a second longitudinal edge 162*f* to define a first lateral width W1, and the second substrate 164 may extend laterally between a first longitudinal edge 164*e* and a second longitudinal edge 164*f* to define a second lateral width W2.

In some configurations, the proximal edge 162*b* of the first substrate 162 and/or the proximal edge 164*b* of the second substrate 164 may extend laterally across the backsheet 136. As shown in FIGS. 2A-3, the first substrate 162 includes a garment facing surface 162*c* and an opposing wearer facing surface 162*d*, and the second substrate 164 includes a garment facing surface 164*c* and an opposing wearer facing surface 164*d*.

In some configurations, the first elastic belt 106 and/or the second elastic belt 108 may include a folded portion of at least the first substrate 162 and/or the second substrate 164. For example, as shown in FIGS. 3A and 3B, the first elastic belt 106 and/or the second elastic belt 108 may include a folded portion 162*g* of the first substrate 162 extending longitudinally between a fold line 162*h* in the first substrate 162 and a lateral edge 162*i*. As such, the folded portion 162*g* of the first substrate 162 may be connected with the wearer facing surface 164*d* of the second substrate 164. In some configurations, the folded portion 162*g* of the first substrate 162 may also be connected with and/or overlap the chassis 102. In some configurations, the folded portion 162*g* of the first substrate 162 may also be connected with the wearer facing surface 162*d* of the first substrate 162. In some configurations, a portion of the folded portion 162*g* of the first substrate 162 may be left unbonded to the chassis 102 and/or the second substrate 164, forming a pocket having an opening oriented toward the lateral centerline 162*c* of the chassis 102. In another example, the first elastic belt 106 and/or the second elastic belt 108 may include a folded portion of the second substrate 164 extending longitudinally between a fold line in the second substrate 164 and a lateral edge. As such, the folded portion of the second substrate 164 may be connected with the garment facing surface 162*c* of the first substrate 162. As such, in some configurations, a fold line of the first substrate 162 and/or a fold line of the second substrate 164 may define at least a portion of the waist opening 110. It is to be appreciated that various waist configurations may be utilized. For example, as shown in FIG. 3A1, the folded portion 162*g* may be sandwiched between the second substrate 164 and the backsheet 136. In another example shown in FIG. 3A2, the second substrate 164 may be sandwiched between the folded portion 162*g* and the backsheet 136. Although FIGS. 3A1 and 3A2 show configurations of the first belt 106, it is to be appreciated that such configurations may be applied with the second belt 108.

It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that components of the first elastic belt 106 and the second elastic belt 108, such as the first substrate 162, and/or second substrate 164 may be constructed from various materials. For example, the first and/or second belts may include a first substrate 162, and/or second substrate 164 that may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some configurations, the first and/or second belts may include a first substrate 162, and/or second substrate 164 comprising a nonwoven web of synthetic fibers, and may include a stretchable nonwoven. In some configurations, the first and second elastic belts may include an inner hydrophobic, non-stretchable nonwoven material and an outer hydrophobic, non-stretchable nonwoven material. It is to be appreciated that the belts may configured in various ways, such as disclosed for example, in U.S. Patent Publication No. 2022/0142828 A1, which are both incorporated by reference.

Elastic material 167 may be positioned between the wearer facing surface 162*d* of the first substrate 162 and the garment facing surface 164*c* of the second substrate 164. It is to be appreciated that the elastic material 167 may include one or more elastic elements such as strands, ribbons, elastic films, or panels extending along the lengths of the elastic belts. As shown in FIGS. 2A and 3, the elastic material 167 may include a plurality of elastic strands 168. In some configurations, the elastic material 167 may be an elastic film used to form a zero-strain elastic laminate comprising an elastic film bonded to one or more nonwoven layers and subsequently subjected to mechanical deformation or activation sufficient to weaken the nonwoven layer(s) and enable the laminate to stretch and recover elastically.

It is also to be appreciated that the first substrate 162, second substrate 164, and/or elastic material 167 of the first elastic belt 106 and/or second elastic belt 108 may be bonded together and/or with other components, such as the chassis 102, with adhesive and/or mechanical bonds. It is to be appreciated that adhesive and mechanical bonding methods may be utilized alone or in combination with each other.

In some configurations, adhesive may be applied to at least one of the first substrate 162, second substrate 164, and/or elastic material 167 when being combined to form the first elastic belt 106 and/or second elastic belt 108. In some configurations, mechanical bonding devices may apply mechanical bonds to the to at least one of the first substrate 162, second substrate 164, and/or elastic material 167 when being combined to form the first elastic belt 106 and/or second elastic belt 108. Such mechanical bonds may be applied with heat, pressure, and/or ultrasonic devices. In some configurations, mechanical bonding devices may apply bonds that bond the first substrate 162, second substrate 164, and/or elastic material 167 together and/or may act to trap or immobilize discrete lengths of the contracted elastic strands in the first elastic belt 106 and/or second elastic belt 108.

It is to be appreciated that components of the first elastic belt 106 and/or the second elastic belt 108 may be assembled in various ways and various combinations to create various desirable features that may differ along the lateral width and/or longitudinal length of the first elastic belt 106 and/or the second elastic belt 108. Such features may include, for example, Dtex values, bond patterns, aperture arrangements, elastic positioning, Average Dtex values, Average Pre-Strain values, rugosity frequencies, rugosity wavelengths, height values, and/or contact area. It is to be appreciated that differing features may be imparted to various components, such as for example, the first substrate 162, second substrate 164, and elastic material 167 before and/or during stages of assembly of the first elastic belt 106 and/or the second elastic belt 108.

It is to be appreciated that the first elastic belt 106 and/or the second elastic belt 108 may include various configurations of belt elastic materials 167 arranged in relation to each other and to the first substrate 162, and the second substrate 164. As discussed above, the elastic material 167 may include configurations of one or more elastic elements such as strands, ribbons, films, or panels positioned in various arrangements. In some configurations, the elastic material 167 may comprise various elastics, elastic features and arrangements, and processes for assembly, and that the first substrate 162, second substrate 164, and/or elastic material 167 may be bonded together with various methods and apparatuses to create various elastomeric laminates, such as described in 2018/0168889 A1; 2018/0168874 A1; 2018/0168875 A1; 2018/0168890 A1; 2018/0168887 A1; 2018/0168892 A1; 2018/0168876 A1; 2018/0168891 A1; 2019/0298586 A1; 2019/0070042 A1; 2018/0168878 A1; 2018/0168877 A1; 2018/0168880 A1; 2018/0170027 A1; 2018/0169964 A1; 2018/0168879 A1; 2018/0170026 A1; 2019/0070041 A1; 2021/0282797A1; and 2021/0275362 A1, which are all incorporated by reference. It is also to be appreciated the elastic materials 167 herein may be configured with identical or different colors in various different locations on the first elastic belt 106 and/or the second elastic belt 108.

In some configurations, the elastic material 167 may be configured as elastic strands 168 disposed at a constant interval in the longitudinal direction. In other embodiments, the elastic strands 168 may be disposed at different intervals in the longitudinal direction. In some configurations, the Dtex values of the elastic strands 168 may be constant or varied along the longitudinal direction. In some configurations, the elastic material 167 in a stretched condition may be interposed and joined between uncontracted substrate layers. When the elastic material 167 is relaxed, the elastic material 167 returns to an unstretched condition and contracts the substrate layers. The elastic material 167 may provide a desired variation of contraction force in the area of the ring-like elastic belt. It is to be appreciated that the chassis 102 and elastic belts 106, 108 may be configured in different ways other than as depicted in attached Figures. It is also to be appreciated that the elastic material 167 material may be joined to the substrates continuously or intermittently along the interface between the elastic material 167 material and the substrates. In some configurations, the elastic strands 168 may be in the form of extruded elastic strands, which may also be bonded with the first substrate 162 and/or second substrate 164 in a pre-corrugated configuration, such as disclosed for example in U.S. Pat. No. 5,681,302, which is incorporated by reference herein.

As discussed above for example with reference to FIGS. 2A and 3, the elastic material 167 discussed herein may be in the form of elastic strands 168. In some configurations, the elastic strands 168 may be parallel with each other and/or with the lateral axis 126. It is to be appreciated that the first elastic belt 106 and/or second elastic belt 108 may be configured to include various quantities of elastic strands 168. In some configurations, elastic strands 168 may be grouped in pairs. In some configurations, the first elastic belt 106 and/or second elastic belt 108 may comprise from about 10 to about 1500 elastic strands 168. It is also to be appreciated that elastic strands 168 herein may comprise various Dtex values, strand spacing values, and pre-strain values and such elastic strands 168 may utilized with other elastic strands to create first and second elastic belts 106, 108 comprising elastic strands 168 in various combinations of Dtex values, strand spacing values, and pre-strain values. For example, in some configurations, the Average-Dtex of one or more elastic strands 168 may be greater than 500. In some configurations, the Average-Dtex of one or more elastic strands 168 may be from about 10 to about 1500, specifically reciting all 1 Dtex increments within the above-recited range and all ranges formed therein or thereby. In some configurations, a plurality of elastic strands 168 may comprise an Average-Strand-Spacing of less than or equal to 4 mm. In some configurations, a plurality of elastic strands 168 may comprise an Average-Strand-Spacing from about 0.25 mm to about 4 mm, specifically reciting all 0.01 mm increments within the above-recited range and all ranges formed therein or thereby. In some configurations, a plurality of elastic strands 168 may comprise an Average-Strand-Spacing of greater than 4 mm. In some configurations, the Average-Pre-Strain of each of a plurality of elastic strands may be from about 50% to about 400%, specifically reciting all 1% increments within the above-recited range and all ranges formed therein or thereby. In some configurations, the elastic strands 168 comprise an Average-Strand-Spacing from about 0.25 mm to about 4 mm and an Average-Dtex from about 10 to about 500. In some configurations, the elastic strands 168 may comprise an Average-Pre-Strain from about 75% to about 300%.

In some configurations, a first plurality of elastic strands may comprise a first Average-Pre-Strain from about 75% to about 300%, and a second plurality of elastic strands may comprise a second Average-Pre-Strain that is greater than first Average-Pre-Strain. In some configurations, a first plurality of elastic strands comprises an Average-Strand-Spacing from about 0.25 mm to about 4 mm and an Average-Dtex from about 10 to about 500; and a second plurality of elastic strands may comprise an Average-Strand-Spacing greater than about 4 mm and an Average-Dtex greater than about 450.

In some configurations, such as shown in FIG. 2A, the elastic strands 168 may be referred to herein as outer waist elastics 170 and inner waist elastics 172. Elastic strands 168, such as the outer waist elastics 170, may continuously extend laterally between the first and second opposing end regions 106*a*, 106*b* of the first elastic belt 106 and between the first and second opposing end regions 108*a*, 108*b* of the second elastic belt 108. Some elastic strands 168, such as the inner waist elastics 172, may be configured with discontinuities in areas, such as for example, where the first and second elastic belts 106, 108 overlap portions of the chassis 102, such as the absorbent assembly 140.

As shown in FIG. 2A, the first elastic belt 106 and/or the second elastic belt 108 may be configured with low-stretch zones 701 and high-stretch zones 703. The first elastic belt 106 and/or the second elastic belt 108 may include a first high-stretch zone 703*a* and a second high-stretch zone 703*b* separated laterally by a low-stretch zone 701. Portions of the chassis 102, such as the backsheet 136 and absorbent assembly 140, may be connected with the first elastic belt 106 and/or the second elastic belt 108 in the low-stretch zones 701 in the first waist region 116 and/or the second waist region 118. The high-stretch zones 703 are elasticated by the elastic material 167, such as the elastic strands 168, 172; and the low-stretch zones 701 may comprise cut lines separating the elastic material 167, such as the elastic strands 168, 172. In some configurations, the elastic material 167 may be cut in an unbonded region where the elastic material is not bonded with first substrate 162 and the second substrate 164. Thus, the elastic material 167 retracts from the unbonded region and form low-stretch zone 701. In some configurations, the elastic material 167 may be cut into several discrete pieces. In turn, the low-stretch zones 701 define regions of the first elastic belt 106 and/or the second elastic belt 108 that have relatively less elasticity than the high-stretch zones 703. The discrete elastic material 167 that has been cut and which are elastically contracted do not add any substantial amount of elastication to the low-stretch zone 701. As such, upon application of a force, the high-stretch zones 703 will elongate more than the low-stretch zones 701. As provided above, the terms "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force. In some configurations, the first elastic belt 106 and/or the second elastic belt 108 may be configured with high-stretch zones 703 that are elastic and may be configured with low-stretch zones 701 that are not elastic or "inelastic."

Figure 4B:
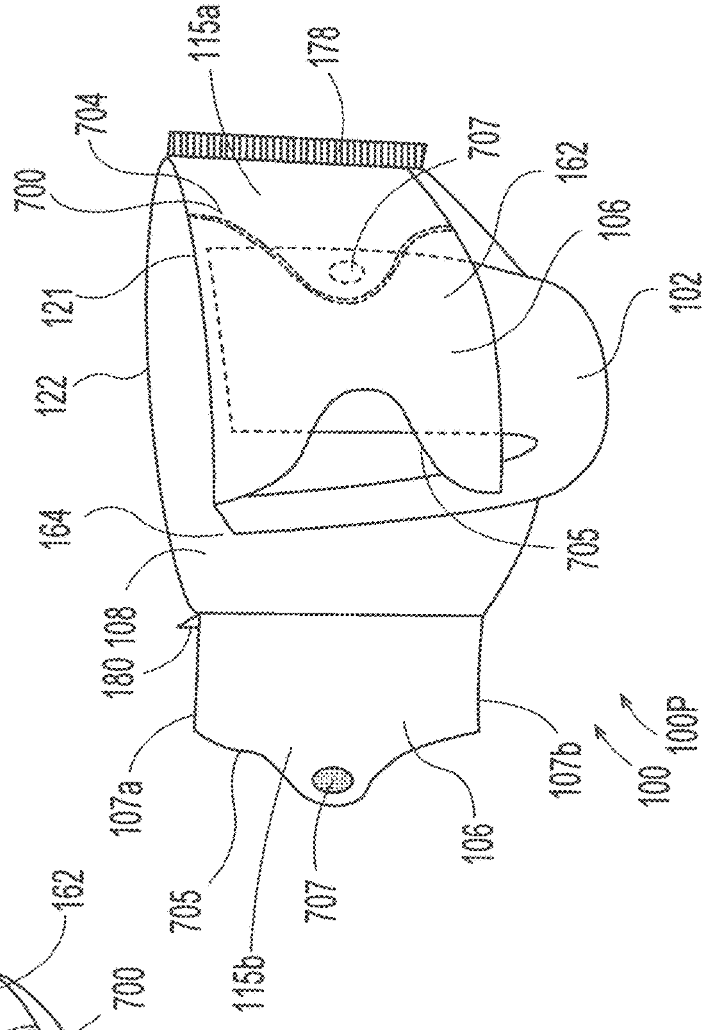
FIG. 4B is a perspective view of the diaper pant of FIG. 4A showing the front belt having been torn along one of the frangible pathways.
Figure 4A:
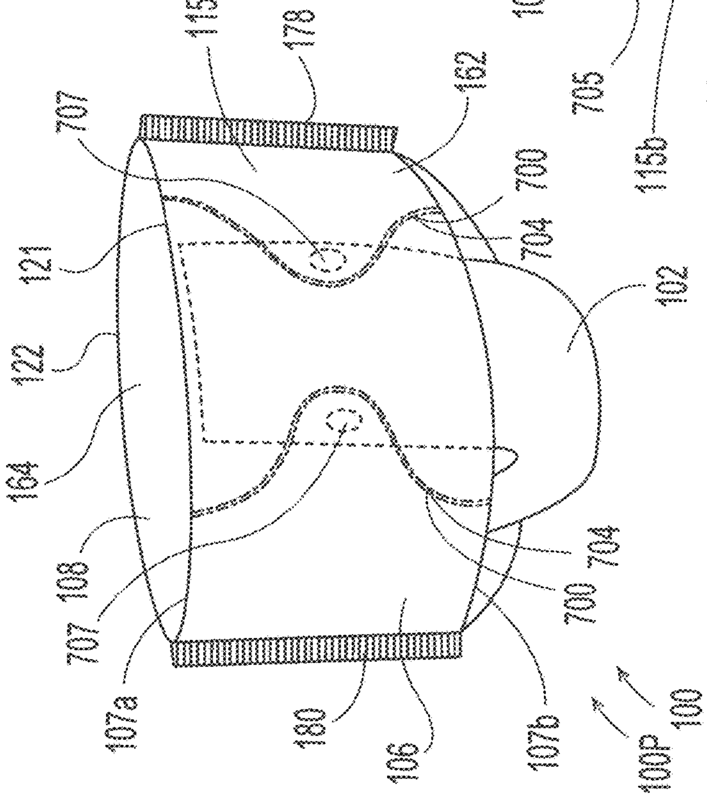
FIG. 4A is perspective view of a diaper pant including frangible pathways in a front belt and adjacent an absorbent chassis.
Figure 4C:
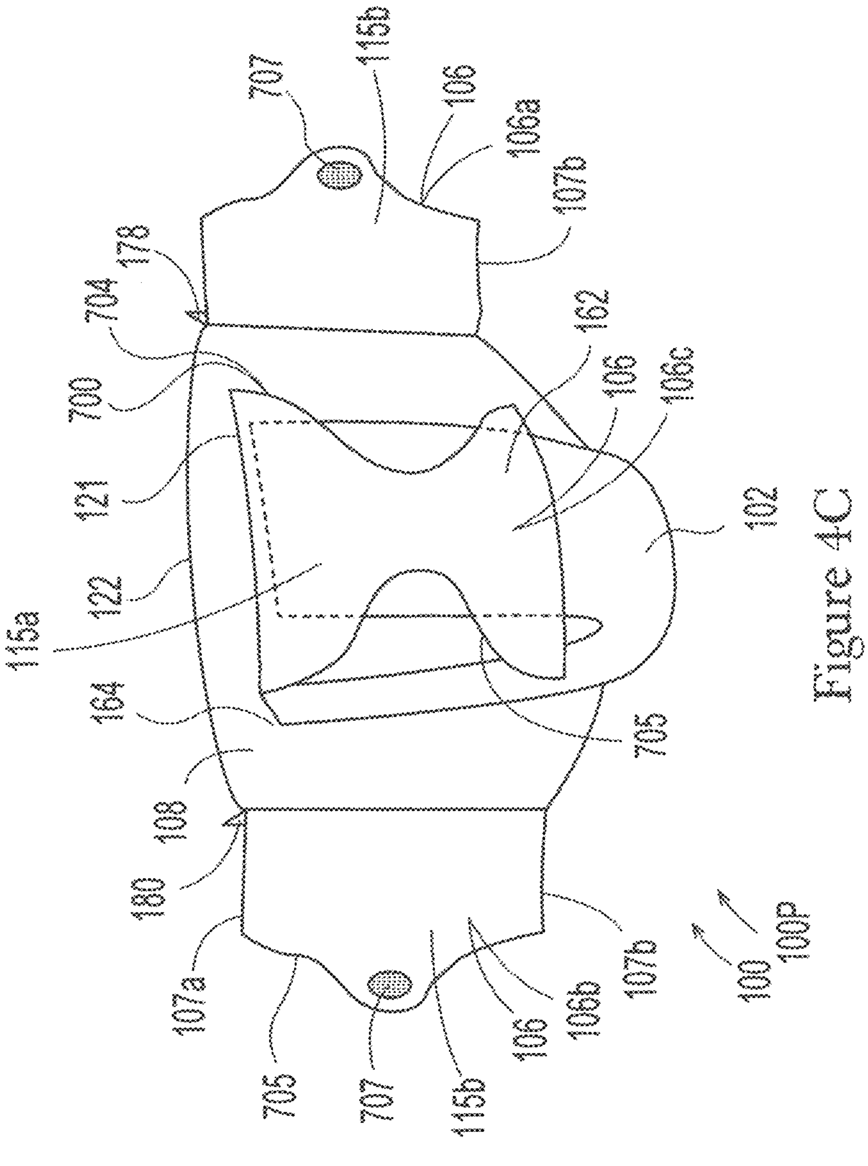
FIG. 4C is a perspective view of the diaper pant of FIG. 4A showing the front belt having been torn along two frangible pathways.

As discussed above, the diaper pants 100P described with reference to FIGS. 1-3C may include one or more frangible pathways in the first belt 106 and/or the second belt 108. For example, FIGS. 4A-4C show an example diaper pant 100P with a first belt 106 that includes frangible pathways 700. The frangible pathways 700 may be configured to allow the first elastic belt 106 to be relatively easily torn along the frangible pathway 700, such as when removing the diaper pant 100P from a wearer. FIG. 4B shows a view of the diaper pant 100P from FIG. 4A, illustrating the first belt 106 after having been torn along the frangible pathway 700 through both the outer longitudinal outer laterally extending edge 107*a* and the inner laterally extending edge 107*b* of the first belt 106. As such, the first elastic belt 106 shown in FIG. 4B is separated by opposing tear lines 705. It is to be appreciated the first elastic belt 106 may be torn along both frangible pathways 700 in FIG. 4B. For example, FIG. 4C shows the diaper pant of FIG. 4A showing the front belt having been torn along two frangible pathways 700. As shown in FIG. 4C, the central region 106*c* of the first elastic belt 106 may remain bonded with the chassis 102 after separating the first and second opposing end regions 106*a*, 106*b* from the central region 106*c* by tearing the elastic belt 106 along the frangible pathways 700.

As discussed in more detail below, the frangible pathways 700 comprise a plurality of lines of weakness 704 configured such that all elastic strands 168 in the first elastic belt 106 are severed at least once in the frangible pathway 700. Severing the elastic strands 168 in the frangible pathway 700 helps make it relatively easier to tear the first elastic belt 106 along the frangible pathway 700. For example, when the elastic strands 168 are severed, the first substrate 162 and second substrate 164 of the first elastic belt 106 need only need to be torn without having to also tear uncut elastic strands 168. It is to be appreciated that the diaper pant 100P may include various quantities of frangible pathways 700 that may be: positioned in various locations; define various shapes; and extend for various lengths. For example, the first elastic belt 106 may comprise a first belt length defined by a longitudinal distance between the proximal edge 107*b* and the distal edge 107*a*, and the frangible pathway 700 may extend for a total length from an outermost edge of a line of weakness 704 nearest the proximal edge 107*b* of the first belt 106 to an outermost edge of a line of weakness 704 nearest the distal edge 107*a* of the first belt 106. In some configurations, the frangible pathway 700 may extend for a total length that is greater than, equal to, or less than the first belt length. In some configurations, the lines of weakness 704 may extend for a length from a first end to a second end, and a sum of the all the lengths of lines of weakness 704 in the frangible pathway 700 may be greater than the frangible pathway total length.

In some configurations, diaper pants 100P may be configured such that one or both of the first elastic belt 106 and the second elastic belt 108 include one or more frangible pathways 700. The frangible pathways 700 may be positioned in various locations on the first and second elastic belts 106, 108. For example, such as shown in FIGS. 4A-4C, frangible pathways 700 may extend to overlap with the chassis 102. In some configurations, the frangible pathways 700 may extend in straight lines and/or may be curved and/or have curved portions. In some configurations, the frangible pathways 700 may extend longitudinally for the entire length or less than the entire length of the first belt 106 and/or second belt 108. In some configurations, frangible pathways 700 may be positioned partially or entirely laterally between the first and second side seams 178, 180 and the chassis 102.

Figure 5A:
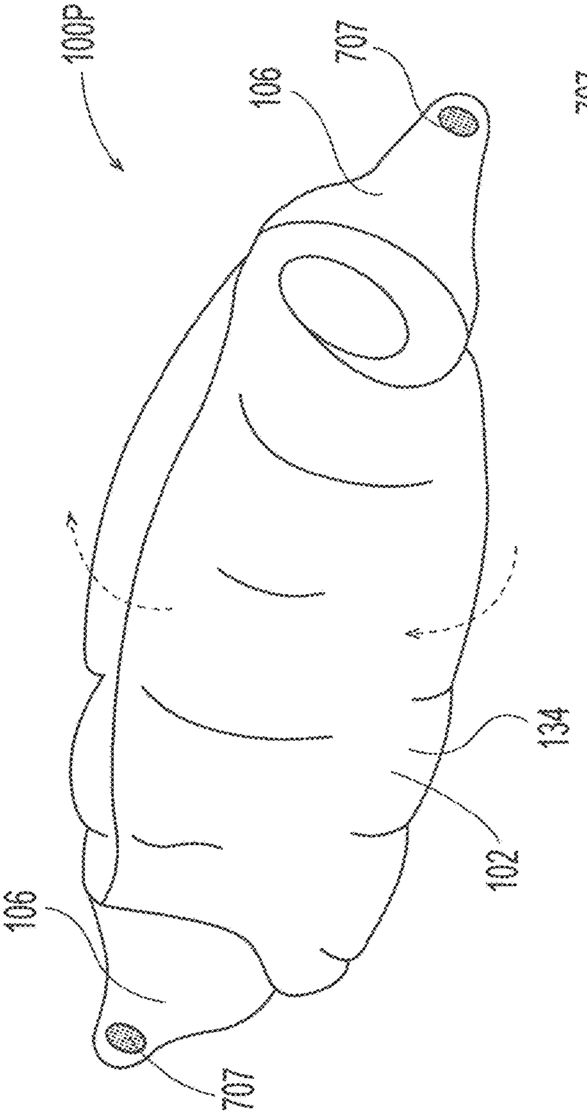
FIG. 5A shows the diaper pant of FIG. 4C being rolled up onto itself in a longitudinal direction.
Figure 5B:
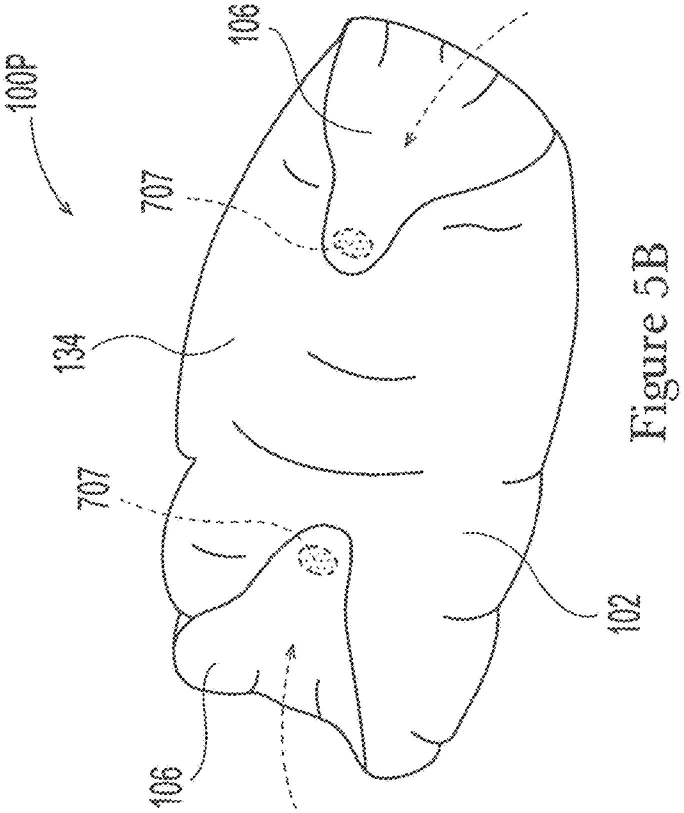
FIG. 5B shows the diaper pant of FIG. 5A with fastener components connected with the backsheet of the chassis to maintain the diaper pant in a disposal configuration.

In some configurations, the frangible pathways 700 may be configured and/or positioned to provide access to and/or function with other features, such as disposal features. For example, the diaper pant 100P shown in FIGS. 4A-4C includes fastener components 707 positioned on the wearing facing surface 115*b* of the first elastic belt 106. In some configurations, the fastener components 707 may be positioned between the first elastic belt 106 and the chassis 102. The fastener component 707 may be configured to refastenably connect with other portions of the diaper pant 100P, such as for example, the garment facing surfaces of the first elastic belt 106, the second elastic belt 108, or the chassis 102. As such, once the first elastic belt 106 is torn along the frangible pathways 700, the diaper pant 100P may be removed from a wearer and rolled or folded up for disposal, and the fastener component 707 may be connected with another portion of the diaper pant 100P to help maintain the diaper pant 100P in a disposal configuration. For example, FIG. 4C shows a diaper pant 100P after tearing the first elastic belt 106 along two frangible pathways. FIG. 5A shows the diaper pant 100P of FIG. 4C with the chassis 102 being rolled up onto itself in a longitudinal direction. And FIG. 5B shows the diaper pant 100P of FIG. 5A with fastener components 707 refastenably connected with the backsheet 136 of the chassis 102 to maintain the diaper pant 100P in a disposal configuration. In some configurations, when tearing the elastic belt along the frangible pathway 700, the tearing process may begin by tearing from the outer edge 107*a* or the inner edge 107*b* of the elastic belt 106. As discussed in more detail below, in some configurations, the first elastic belt 106 may also include an opening, such as a slit located adjacent to or in the proximity of the fastener component 707 and the weakened region 700 to help facilitate starting to tear the frangible pathway 700 in a region of the elastic belt 106 longitudinally between the outer edge 107*a* and the inner edge 107*b*.

It is also to be appreciated that the frangible pathways 700 may comprise lines of weakness 704 that are: configured in various ways; positioned in various locations and orientations relative to each other; defined by various shapes; and extend for various lengths. For example, in some configurations, the lines of weakness 704 comprise discrete cut lines that penetrate through some or all the layers of the elastic belt 106. In some configurations, the lines of weakness 704 comprise discrete bonds wherein materials of the first substrate and the second substrate are fused together. In some configurations, the lines of weakness 704 may be linear, curvilinear, or have a regular or irregular geometry and may comprise one or more of a perforation, a bond, an aperture, or a mechanically thinned region of a material such as a nonwoven, or a combination thereof. It is also to be appreciated that the lines of weakness 704 can be formed with different lengths and spacings to achieve different separation forces.

As discussed above, absorbent articles 100, such as diaper pants 100P, may be configured with frangible pathways 700 comprising lines of weakness 704 arranged in various ways to help improve a caregiver's ability to remove a soiled diaper pant 100P from a wearer without having to remove a soiled diaper pant from a wearer by sliding the soiled diaper pant down the wearer's legs. As discussed above, the frangible pathways 700 may be configured to allow the first elastic belt 106 and/or the second elastic belt 108 to be relatively easily torn along the frangible pathway 700, such as when removing the diaper pant 100P from a wearer. In addition, the frangible pathways 700 may also be configured to provide access to fastener components 707 that may be used to help hold a soiled product in a disposal configuration. The following provides a discussion of example implementations of frangible pathways 700 on diaper pants 100P in the context of the above description of various details of absorbent articles 100, fastener components 707, frangible pathways 700, and lines weakness 704. It is to be appreciated that discussions of frangible pathways 700 in the first elastic belt 106 herein may also apply to frangible pathways 700 in the second elastic belt 108.

Figure 6A:
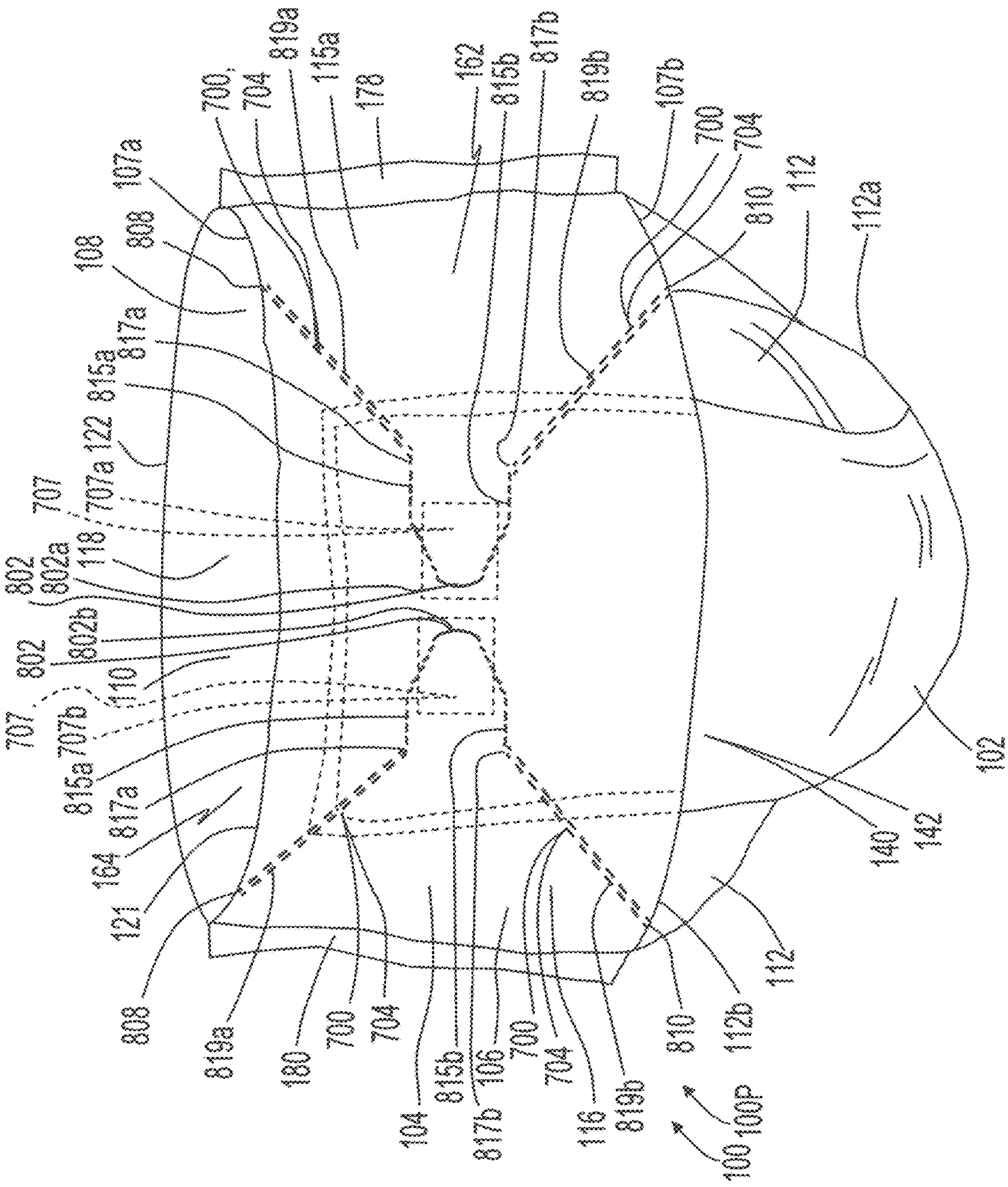
FIG. 6A is a perspective view of a diaper pant with frangible pathways.
Figure 6B:
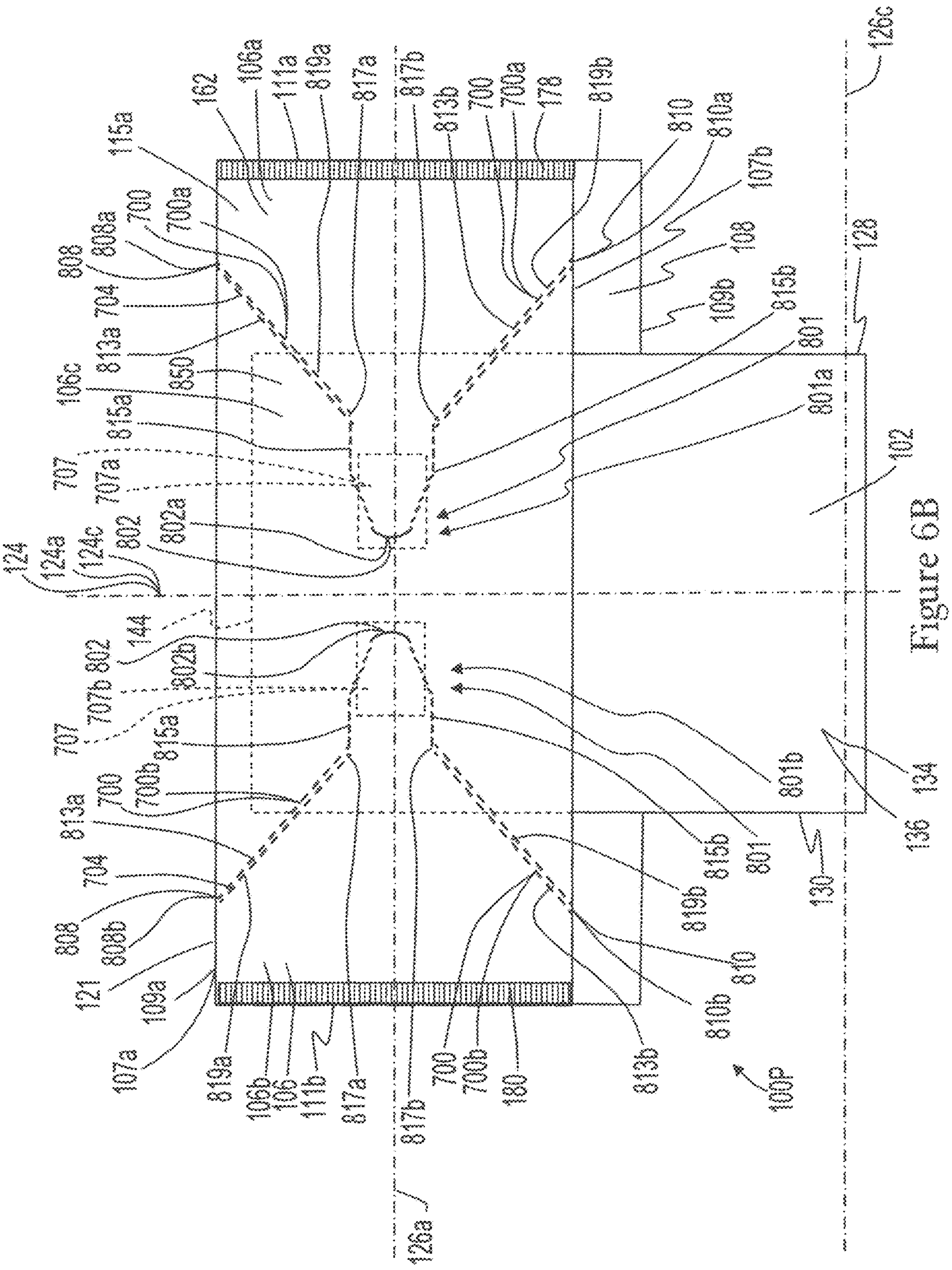
FIG. 6B is a front plan view of the diaper pant of FIG. 6A.

It is to be appreciated that frangible pathways 700 may be positioned in various locations and/or orientations relative to other components of the absorbent article 100 and/or may be configured to function in various ways to help facilitate removal of diaper pant from a wearer. For example, the diaper pant 100P shown in FIGS. 6A and 6B may include one or more frangible pathways 700 extending between a distal terminus 808 on the outer edge 107*a* of the first belt 106 and a distal terminus 810 on the inner edge 107*b* of the first belt 106. As illustrated in FIGS. 6A and 6B, the diaper pant 100P includes a first frangible pathway 700*a* and a second frangible pathway 700*b* in the first belt 106. The first frangible pathway 700*a* may extend between a first distal terminus 808*a* on the outer edge 107*a* of the first belt 106 and a first proximal terminus 810*a* on the inner edge 107*b* of the first belt 106. And the second frangible pathway 700*b* may extend between a second distal terminus 808*b* on the outer edge 107*a* of the first belt 106 and a second proximal terminus 810*b* on the inner edge 107*b* of the first belt 106. It is to be appreciated that the first and second frangible pathways 700*a*, 700*b* may comprise lines of weakness 704 as described above.

It is to be appreciated that the first distal terminus 808*a* and the second distal terminus 808*b* may be located in various lateral positions on the outer edge 107*a* of the first belt 106. For example, in some configurations, the first distal terminus 808*a* and/or the second distal terminus 808*b* may be positioned in the central region 106*c* of the first belt 106. In some configurations, the first distal terminus 808*a* and/or the second distal terminus 808*b* may be positioned laterally between the first longitudinal edge 128 and the second longitudinal edge 130 of the chassis 102. In some configurations, the first distal terminus 808*a* and/or the second distal terminus 808*b* may be positioned in the first end region 106*a* and/or the second end region 106*b* of the first belt 106. In some configurations, the first distal terminus 808*a* and/or the second distal terminus 808*b* may be positioned laterally outboard of the first longitudinal edge 128 and the second longitudinal edge 130 of the chassis 102. In some configurations, the first distal terminus 808*a* and/or the second distal terminus 808*b* may be positioned laterally between the first longitudinal edge 128 of the chassis 102 and the first side seam 178 and/or may be positioned laterally between the second longitudinal edge 130 of the chassis 102 and the second side seam 180. In some configurations, the first distal terminus 808*a* may be laterally aligned with the first longitudinal edge 128 of the chassis 102 or the first longitudinal side edge 111*a* of the first belt 106. In some configurations, the first distal terminus 808*a* may be positioned laterally between the first longitudinal edge 128 of the chassis 102 and the first longitudinal side edge 111*a* of the first belt 106. In some configurations, the second distal terminus 808*b* may be laterally aligned with the second longitudinal edge 130 of the chassis 102 or the second longitudinal side edge 111*b* of the first belt 106. In some configurations, the second distal terminus 808*b* may be positioned laterally between the second longitudinal edge 130 of the chassis 102 and the second longitudinal side edge 111*b* of the first belt 106.

It is also to be appreciated that the first proximal terminus 810*a* and the second proximal terminus 810*b* may be located in various lateral positions on the inner edge 107*b* of the first belt 106. For example, in some configurations, the first proximal terminus 810*a* and/or the second proximal terminus 810*b* may be positioned in the central region 106*c* of the first belt 106. In some configurations, the first proximal terminus 810*a* and/or the second distal terminus 810*b* may be positioned laterally between the first longitudinal edge 128 and the second longitudinal edge 130 of the chassis 102. In some configurations, the first proximal terminus 810*a* and/or the second proximal terminus 810*b* may be positioned in the first end region 106*a* and/or the second end region 106*b* of the first belt 106. In some configurations, the first proximal terminus 810*a* and/or the second proximal terminus 810*b* may be positioned laterally outboard of the first longitudinal edge 128 and the second longitudinal edge 130 of the chassis 102. In some configurations, the first proximal terminus 810*a* and/or the second proximal terminus 810*b* may be positioned laterally between the first longitudinal edge 128 of the chassis 102 and the first side seam 178 and/or may be positioned laterally between the second longitudinal edge 130 of the chassis 102 and the second side seam 180. In some configurations, the first proximal terminus 810*a* may be laterally aligned with the first longitudinal edge 128 of the chassis 102 or the first longitudinal side edge 111*a* of the first belt 106. In some configurations, the first proximal terminus 810*a* may be positioned laterally between the first longitudinal edge 128 of the chassis 102 and the first longitudinal side edge 111*a* of the first belt 106. In some configurations, the second proximal terminus 810*b* may be laterally aligned with the second longitudinal edge 130 of the chassis 102 or the second longitudinal side edge 111*b* of the first belt 106. In some configurations, the second proximal terminus 810*b* may be positioned laterally between the second longitudinal edge 130 of the chassis 102 and the second longitudinal side edge 111*b* of the first belt 106.

As shown in FIG. 6B, the frangible pathways 700 may be configured to extend laterally inward from the from the distal terminus 808 and/or the proximal terminus 810. In turn, portions of the frangible pathway 700 may extend to define an angle that is less than 90 degrees with respect to the outer edge 107*a* and/or the inner edge 107*b* of the first belt 106. Thus, the frangible pathway may define an overall length that is greater than a longitudinal length LT1 of the first belt 106 and/or the longitudinal length LT2 of the second belt 108 discussed above with reference to FIGS. 2C-2E.

With continued reference to FIG. 6B, the first belt 106 may also comprise grip regions 801 providing a place where a user may grasp a portion of the first belt 106 and begin the process of tearing the first belt along the frangible pathway 700. The grip region 801 may comprise an accessibility opening 802 in the first belt 106 and may also comprise a fastener component 707 positioned adjacent the accessibility opening 802. The accessibility opening 802 may comprise slits and/or openings in the first belt 106 and may penetrate through some or all layers of the first belt 106. It is to be appreciated that such slits or openings may be curved and/or straight. The accessibility opening 802 may also be considered part of the frangible pathway 700.

As shown in FIG. 6B, the diaper pant 100P may include a first grip region 801*a* including a first accessibility opening 802*a* and second grip region 801*b* including a second accessibility opening 802*b* in the first belt 106. The first and second accessibility openings 802*a*, 802*b* may be positioned between the outer edge 107*a* and the inner edge 107*b* of the first belt 106. The first and second accessibility openings 802*a*, 802*b* may also be positioned in the central region 106*c* of the first belt 106 and may be positioned between the first longitudinal edge 128, the second longitudinal edge 130 of the chassis 102, and the first lateral edge 144 of the chassis 102. In addition, a first fastener component 707*a* may be positioned adjacent the first accessibility opening 802*a*, and a second fastener component 707*a* may be positioned adjacent the second accessibility opening 802*a*.

As discussed in more detail below, the accessibility opening 802 may help provide a caregiver or wearer access to and/or to grasp the fastener component 707 in the grip region 801 with a finger or thumb. The caregiver or user may then pull on grip region 801 to begin tearing the first belt 106 on the frangible pathway 700. In some configurations, tear lines may simultaneously propagate along the first tear zone 813*a* and the second tear zone 813*b* laterally outward from the central region 106*c* of the first belt 106 toward the distal terminus 808 and the proximal terminus 810. In some configurations, a tear line propagating along the first tear zone 813*a* and a tear line propagating along the second tear zone 813*b* may reach the distal terminus 808 and the proximal terminus 810, respectively, simultaneously or approximately simultaneously. It is also to be appreciated that some diaper pants 100P herein may be configured to include a frangible pathway 700 that extends through or around the fastener component 707 without an accessibility opening. In turn, a user may pinch and/or pull the belt where the frangible pathway 700 is located at or adjacent the fastener component 707 to initiate the tearing process along the frangible pathway 700.

With continued reference to FIG. 6B, the first frangible pathway 700*a* may comprise a first tear zone 813*a* extending from the first accessibility opening 802*a* to the first distal terminus 808*a* and a second tear zone 813*b* extending from the first accessibility opening 802*a* to the first proximal terminus 810*a*. The second frangible pathway 700*b* may comprise a first tear zone 813*a* extending from the second accessibility opening 802*b* to the second distal terminus 808*b* and a second tear zone 813*b* extending from the second accessibility opening 802*b* to the second proximal terminus 810*b*.

It is to be appreciated that the frangible pathways 700 may also comprise one or more functional zones. In turn, the frangible pathways 700 may comprise transition zones 817 that may operatively connect such zones to help facilitate propagation of a tear along the frangible pathway 700 from one zone to another zone. The lines of weakness in the transition zones may be of particular lengths and/or angles relative to lateral centerlines and row spacing to help provide desired propagation of material failure when, for example, removing a product from a wearer. It is to be appreciated that the lengths, angles, and spacings in transition zones may be different from those in adjacent lines of weakness.

As shown in FIG. 6B for example, the first tear zone 813*a* of the first frangible pathway 700*a* may comprise a first initial tear zone 815*a* extending from the first accessibility opening 802*a* to a first transition zone 817*a*. In addition, the first tear zone 813*a* of the first frangible pathway 700*a* may comprise a secondary tear zone 819*a* extending from the first transition zone 817*a* to the first distal terminus 808*a*. The first tear zone 813*a* of the first frangible pathway 700*a* may also comprise a second initial tear zone 815*b* extending from the first accessibility opening 802*a* to a second transition zone 817*b*. Further, the first tear zone 813*a* of the first frangible pathway 700*a* may comprise a second secondary tear zone 819*b* extending from the second transition zone 817*b* to the first proximal terminus 810*a*. The first transition zone 817*a* may operatively connect the first initial tear zone 815*a* with the first secondary tear zone 819*a* to help facilitate the propagation of the tear along the first frangible pathway 700*a* from first initial tear zone 815*a* to the first secondary tear zone 819*a*. With continued reference to FIG. 6B, the first tear zone 813*a* of the second frangible pathway 700*b* may comprise a first initial tear zone 815*a* extending from the second accessibility opening 802*b* to a first transition zone 817*a*. In addition, the first tear zone 813*a* of the second frangible pathway 700*b* may comprise a secondary tear zone 819*a* extending from the first transition zone 817*a* to the second distal terminus 808*b*. The first tear zone 813*a* of the second frangible pathway 700*b* may also comprise a second initial tear zone 815*b* extending from the second accessibility opening 802*b* to a second transition zone 817*b*. Further, the first tear zone 813*a* of the second frangible pathway 700*b* may comprise a second secondary tear zone 819*b* extending from the second transition zone 817*b* to the second proximal terminus 810*b*. The second transition zone 817*b* may operatively connect the second initial tear zone 815*b* with the second secondary tear zone 819*b* to help facilitate the propagation of the tear along the second frangible pathway 700*b* from second initial tear zone 815*b* to the second secondary tear zone 819*b*.

As discussed above, the first elastic belt 106 and/or the second belt 108 may be relatively easily torn along the frangible pathway 700, such as when removing the diaper pant 100P from a wearer. As discussed below with reference to FIGS. 6A-6F, the frangible pathway 700 may be configured to allow a caregiver or wearer to initiate and/or completely tear the first belt 106 and/or the second belt 108 with one hand when removing a diaper pant 100P from a wearer. In addition, the first belt 106 may be separable along the first frangible pathway 700*a* and the second frangible pathway 700*b* to define a first belt zone 831, a second belt zone 832, and a third belt zone 833 positioned laterally between the first and second belt zones 831, 832.

Referring now to FIGS. 6A and 6B, when removing a diaper pant 100P from a wearer, a user may grab the first belt 106 in the grip region 801 by inserting one or more fingers and/or a thumb through the accessibility opening 802 to grasp a portion of the first 106 and fastener component 707. For example, with reference to FIGS. 6B and 6C, a caregiver may insert a finger or thumb through the first accessibility opening 802*a* and grasp the first belt 106 and the first fastener component 707*a* with a first hand. The caregiver's opposing second hand may be used to help stabilize the wearer. For example, the caregiver's opposing second hand may apply a holding or stabilizing force to the wearer at the central region 106*c* of the first belt 106. The user's first hand may then exert a pulling force Fp on the first grip region 801*a* of the first belt 106 outward away from the wearer to initiate a tearing of the first belt 106 along the first frangible pathway 700*a*, such as shown in FIG. 6C.

Figure 6C:
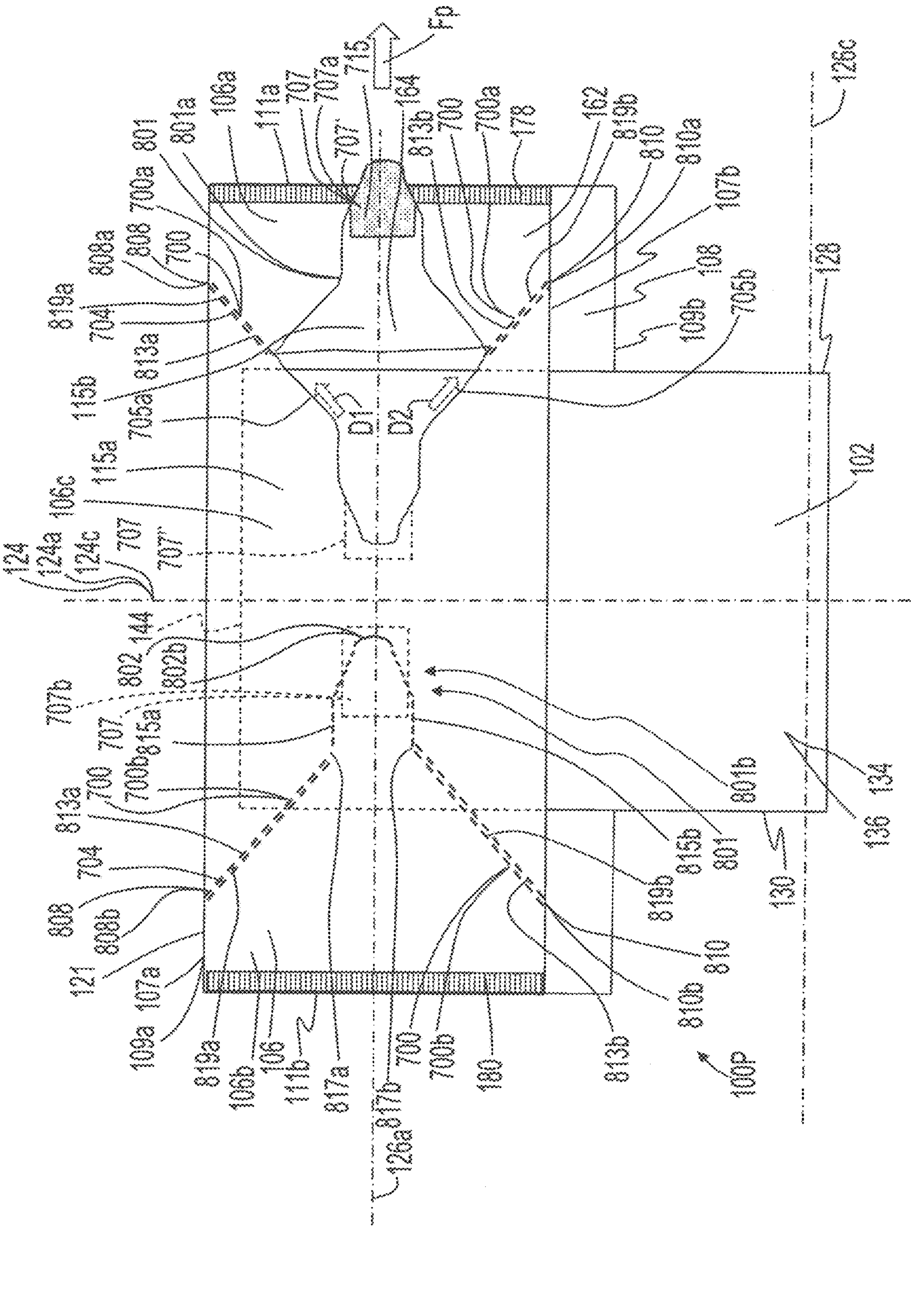
FIG. 6C shows a front plan view of the diaper pant of FIG. 6B as a first frangible pathway is being torn.

With continued reference to FIG. 6C, a pulling force Fp (generally represented by an arrow) may be applied to the first grip region 801*a* in a direction generally toward the first end region 106*a* of the first belt 106 and/or outward away from the first belt 106 and the wearer. As the force Fp is applied, a first tear line 705*a* and a second tear line 705*b* may simultaneously propagate along the first tear zone 813*a* and the second tear zone 813*b*, respectively. The first tear line 705*a* may propagate from the first accessibility opening 802*a* along the first tear zone 813*a* of the first frangible pathway 700*a* in longitudinal and lateral directions partially through and adjacent to the first fastener component 707*a* and then in a direction D1 that is generally laterally and longitudinally outward from the central region 106*c* of the first belt 106 and toward the first distal terminus 808*a* in the first end region 106*a* of the first belt 106. Simultaneously, the second tear line 705*b* may propagate from the first accessibility opening 802*a* in longitudinal and lateral directions partially through and adjacent to the first fastener component 707*a* along the second tear zone 813*b* of the first frangible pathway 700*a* in a direction D2 that is generally laterally outward and longitudinally inward from the central region 106*c* of the first belt 106 and toward the first proximal terminus 810*a* in the first end region 106*a* of the first belt 106.

In some configurations, the first tear line 705*a* may propagate from the first accessibility opening 802*a* along the first initial tear zone 815*a* of the first frangible pathway 700*a* to the first transition zone 817*a*. From the first transition zone 817*a*, the first tear line 705*a* may then propagate along the first secondary tear zone 819*a* to the first distal terminus 808*a*. In addition, the second tear line 705*b* may propagate from the first accessibility opening 802*a* along the second initial tear zone 815*b* of the first frangible pathway 700*a* to the second transition zone 817*b*. From the second transition zone 817*b*, the second tear line 705*b* may then propagate along the second secondary tear zone 819*b* to the first proximal terminus 810*a*. As discussed in more detail below, the first frangible pathway 700*a* may be configured such that the first tear line 705*a* and the second tear line 705*b* may reach first distal terminus 808*a* and the first proximal terminus 810*a*, respectively, at the same time or about the same time.

Figure 6D:
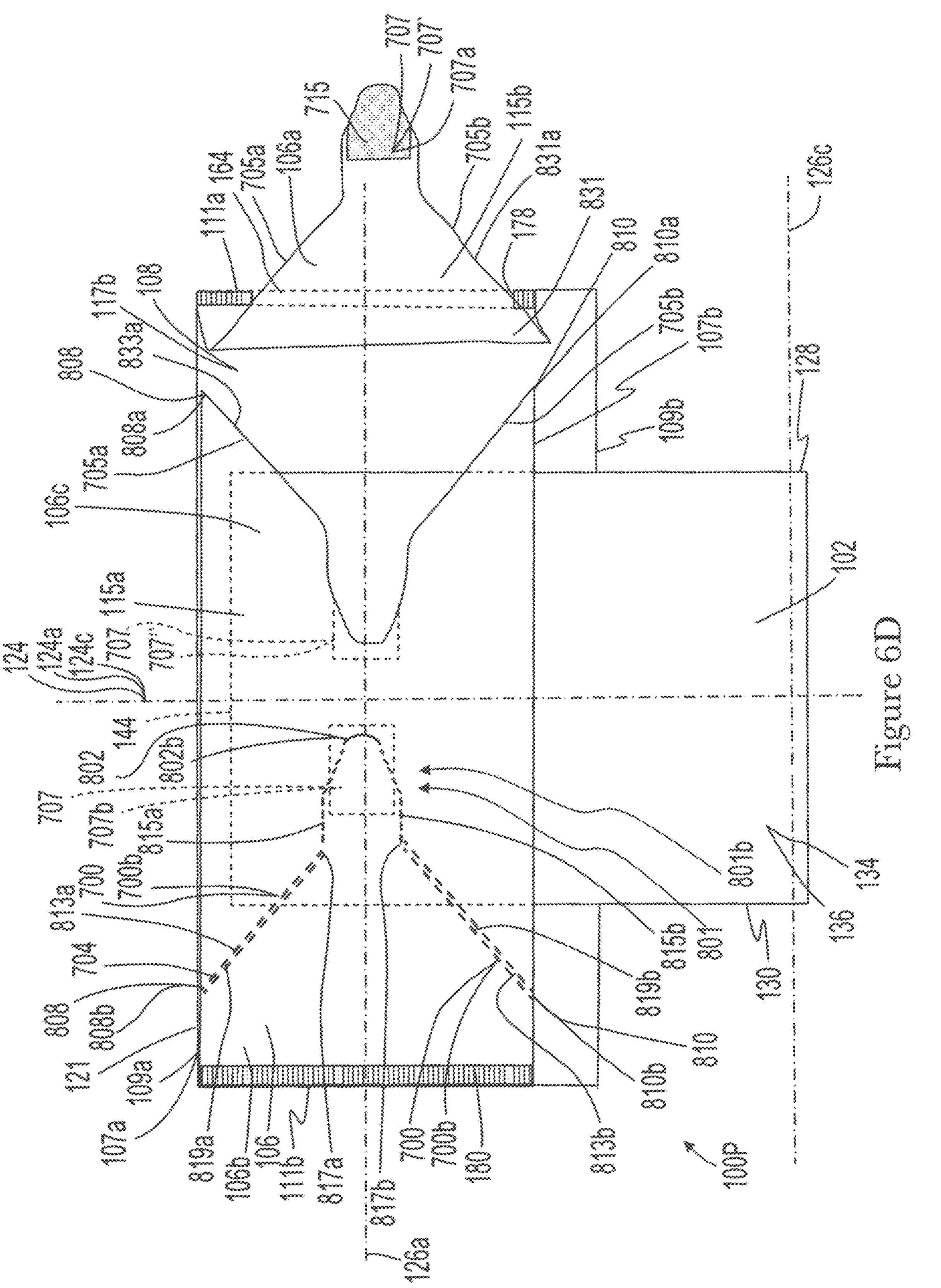
FIG. 6D shows a front plan view of the diaper pant of FIG. 6C after the first frangible pathway has been completely torn.

As shown in FIG. 6D, the first belt 106 may be separable along the first frangible pathway 700*a* to define a first belt zone 831. For example, the first belt zone 831 may be formed once the first tear line 705*a* propagates through the first distal terminus 808*a* and the second tear line 705*b* propagates through to the first proximal terminus 810*a*, the first belt zone 831 may be formed. As shown in FIG. 6D, a first edge 831*a* of the first belt zone 831 is formed by tearing the first frangible pathway 700*a*. In addition, a first edge 833*a* of the third belt zone 833 discussed in more detail below is also formed by tearing the first frangible pathway 700*a*. The first belt zone 831 may extend from the first edge 831*a* of the first and second tear lines 705*a*, 705*b* to the first side seam 178 or the first longitudinal side edge 111*a* of the first belt 106. In addition, the first belt zone 831 may include the first fastener component 707*a*. As discussed below, the first belt zone 831 may include the entirety of or a portion of first fastener component 707*a*.

Figure 6E:
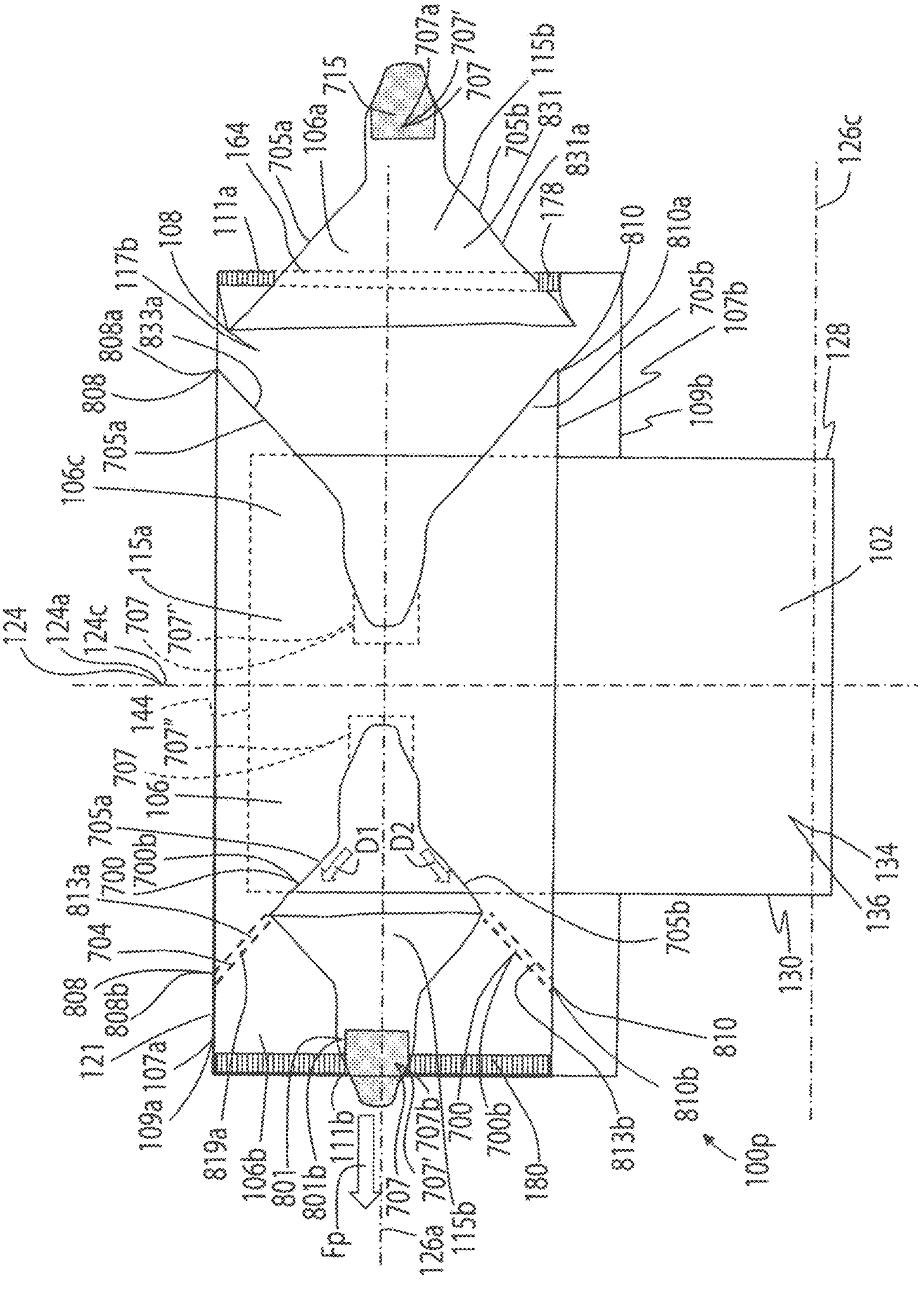
FIG. 6E shows a front plan view of the diaper pant of FIG. 6D as a second frangible pathway is being torn.

With the first belt zone 831 being defined by tearing the first belt 106 along the first frangible pathway 700*a*, a user may proceed to define the second belt zone 832 by tearing the first belt 106 along the second frangible pathway 700*b*. Referring now to FIGS. 6D and 6E, a caregiver may insert a finger or thumb through the second accessibility opening 802*b* and grasp the first belt 106 and the second fastener component 707*b* with a first hand. The caregiver's opposing second hand may be used to help stabilize the wearer. For example, the caregiver's opposing second hand may apply a holding or stabilizing force to the wearer at the central region 106*c* of the first belt 106. The user's first hand may then exert a pulling force Fp on the second grip region 801*b* of the first belt 106 outward away from the wearer to initiate a tearing of the first belt 106 along the second frangible pathway 700*b*, such as shown in FIG. 6E.

With continued reference to FIG. 6E, a pulling force Fp (generally represented by an arrow) is applied to the second grip region 801*b* in a direction generally toward the second end region 106*b* of the first belt 106 and/or outward away from the first belt 106. As the pulling force Fp is applied, a first tear line 705*a* and a second tear line 705*b* may simultaneously propagate along the first tear zone 813*a* and the second tear zone 813*b*, respectively. The first tear line 705*a* may propagate from the second accessibility opening 802*b* along the first tear zone 813*a* of the second frangible pathway 700*b* in longitudinal and lateral directions partially through and adjacent to the second fastener component 707*b* and then in a direction D1 that is generally laterally and longitudinally outward from the central region 106*c* of the first belt 106 and toward the second distal terminus 808*b* in the second end region 106*b* of the first belt 106. Simultaneously, the second tear line 705*b* may propagate from the second accessibility opening 802*b* in longitudinal and lateral directions partially through and adjacent to the second fastener component 707*b* along the second tear zone 813*b* of the second frangible pathway 700*b* in a direction D2 that is generally laterally outward and longitudinally inward from the central region 106*c* of the first belt 106 and toward the second proximal terminus 810*b* in the second end region 106*b* of the first belt 106.

In some configurations, the first tear line 705*a* may propagate from the second accessibility opening 802*b* along the first initial tear zone 815*a* of the second frangible pathway 700*b* to the first transition zone 817*a*. From the first transition zone 817*a*, the first tear line 705*a* may then propagate along the first secondary tear zone 819*a* to the second distal terminus 808*b*. In addition, the second tear line 705*b* may propagate from the second accessibility opening 802*b* along the second initial tear zone 815*b* of the second frangible pathway 700*b* to the second transition zone 817*b*. From the second transition zone 817*b*, the second tear line 705*b* may then propagate along the second secondary tear zone 819*b* to the second proximal terminus 810*b*. As discussed in more detail below, the second frangible pathway 700*b* may be configured such that the first tear line 705*a* and the second tear line 705*b* may reach second distal terminus 808*b* and the second proximal terminus 810*b*, respectively, at the same time or about the same time.

Figure 6F:
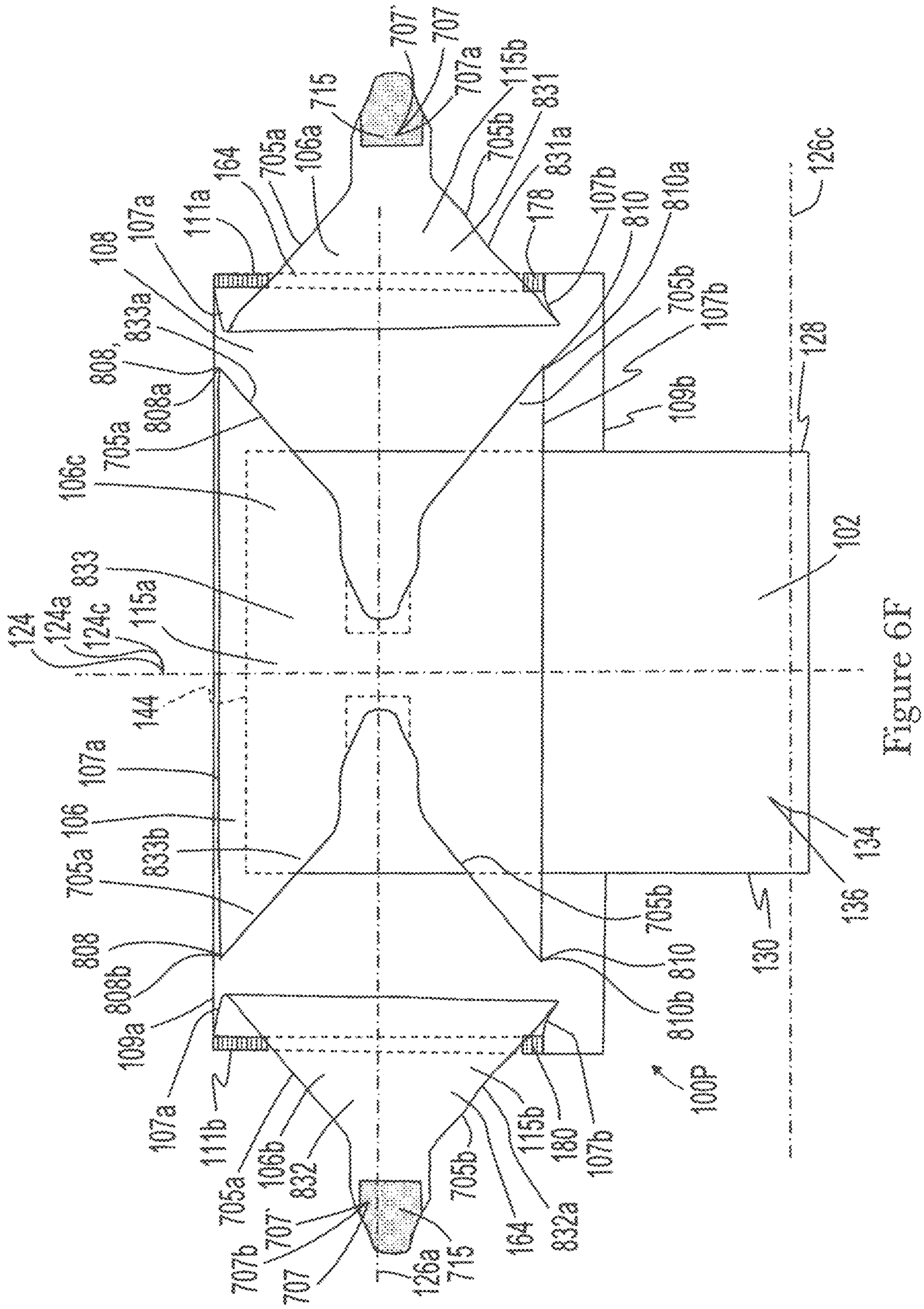
FIG. 6F shows a front plan view of the diaper pant of FIG. 6E after the second frangible pathway has been completely torn.

As shown in FIG. 6F, the first belt 106 may be separable along the second frangible pathway 700*b* to define a second belt zone 832 and a third belt zone 833. For example, the second belt zone 832 may be formed once the first tear line 705*a* propagates through the second distal terminus 808*b* and the second tear line 705*b* propagates through to the second proximal terminus 810*b*, the second belt zone 832 may be formed. As shown in FIG. 6F, a first edge 832*a* of the second belt zone 832 is formed by tearing the second frangible pathway 700*b*. In addition, a second edge 833*b* of the third belt zone 833 is also formed by tearing the second frangible pathway 700*b*. The second belt zone 832 may extend from the first edge 832*a* of the first and second tear lines 705*a*, 705*b* to the second side seam 180 or the second longitudinal side edge 111*b* of the first belt 106. In addition, the second belt zone 832 may include the second fastener component 707*b*. The third belt zone 833 may extend laterally between the first edge 833*a* and the second edge 833*b* and may remain connected with the chassis 102.

Although the tearing process is described above with reference to FIGS. 6A-6F as tearing the first belt 106 along the first frangible pathway 700*a* before tearing the first belt along the second frangible pathway 700*b*, it is to be appreciated that the tearing of first belt 106 along the frangible pathways 700 may occur in various different orders and in different manners. For example, the first belt 106 may be torn along second frangible pathway 700*b* to define the second belt zone 832 before tearing the first belt 106 along the first frangible pathway 700*a* to define the first belt zone 831. In another example, the first belt 106 may be torn simultaneously along the first frangible pathway 700*a* and the second frangible pathway 700*b* to define the first belt zone 831, the second belt zone 832, and the third belt zone 833.

Once the first belt 106 is torn along the frangible pathways 700 to define the first belt zone 831, the second belt zone 832, and the third belt zone 833, the diaper pant 100P may be removed from a wearer in a manner similar to that of a conventional taped diaper. After being removed from a wearer, the diaper pant 100P may be placed in a disposal configuration, such as discussed above with reference to FIGS. 5A and 5B, by rolling and/or folding the chassis 102 onto itself in a longitudinal direction. The first belt zone 831 and the second belt zone 832 may be used to further wrap the diaper pant 100P onto itself. And the fastener components 707 on the first belt zone 831 and the second belt zone 832 may be connected with another portion of the diaper pant 100P to help maintain the diaper pant 100P in the disposal configuration.

Figure 7A:
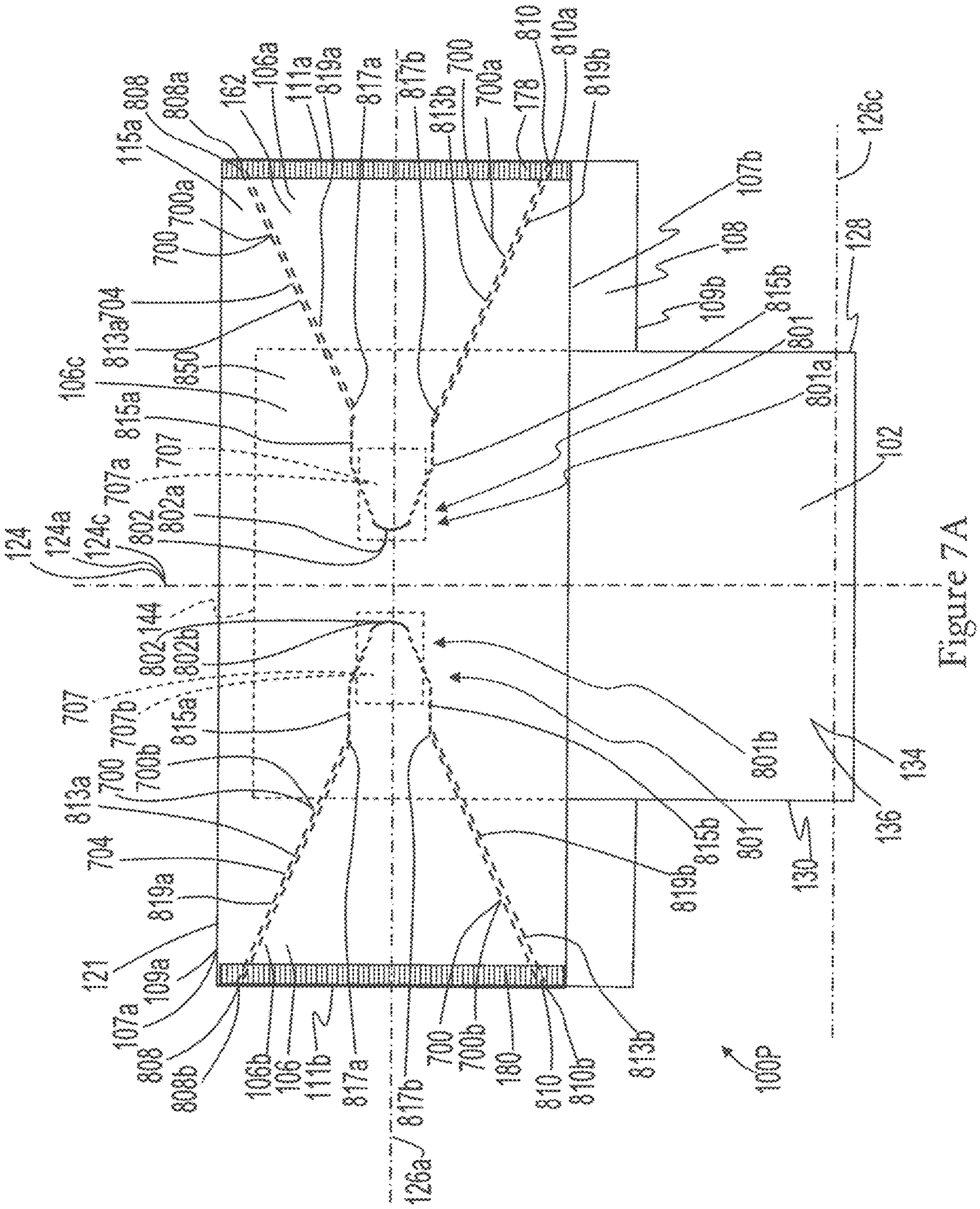
FIG. 7A is a front plan view of another configuration of a diaper pant with frangible pathways having a distal terminus and a proximal terminus positioned on side seams.

As discussed above, it is to be appreciated that the first distal terminus 808*a* and the second distal terminus 808*b* may be located in various longitudinal positions between the outer edge 107*a* and the inner edge 107*b* of the first belt 106. And the first proximal terminus 810*a* and the second proximal terminus 810*b* may be located in various longitudinal positions between the outer edge 107*a* and the inner edge 107*b* of the first belt 106. For example, in some configurations, such as shown in FIG. 7A for example, the first distal terminus 808*a* and/or the first proximal terminus 810*a* may be located on the first side seam 178 at positions longitudinally inboard of the outer edge 107*a* and longitudinally outboard of the inner edge 107*b* of the first belt 106. Also, as shown in FIG. 7A, the second distal terminus 808*b* and/or the second proximal terminus 810*b* may be located on the second side seam 180 at positions longitudinally inboard of the outer edge 107*a* and longitudinally outboard of the inner edge 107*b* of the first belt 106. As such, completing the tearing process of the first belt 106 may also require tearing portions of the first and/or second side seams 178, 180.

With reference to various aspects of the Figures described above, it is also to be appreciated that grip regions 801 and accessibility openings 802 may be located in various positions in the first end region 106*a*, the second end region 106*b*, and/or the central region 106*c* of the first belt 106. Grip regions 801 and accessibility openings 802 may be positioned between the first longitudinal side edge 111*a*, the second longitudinal side edge 111*b*, the outer edge 107*a*, and the inner edge 107*b* of the first belt 106. For example, the first accessibility opening 802*a* and/or the second accessibility 802*b* may be entirely laterally positioned between the first longitudinal edge 128 and the second longitudinal edge 130 of the chassis 102. In some configurations, the first accessibility opening 802*a* may be positioned laterally between the first longitudinal side edge 128 of the chassis 102 and the first longitudinal side edge 111*a* of the first belt 106 and/or first side seam 178. In some configurations, the second accessibility opening 802*b* may be positioned laterally between the second longitudinal side edge 130 of the chassis 102 and the second longitudinal side edge 111*b* of the first belt 106 and/or second side seam 180. In some configurations, the first accessibility opening 802*a* and/or the second accessibility opening 802*b* may be positioned longitudinally between the first lateral edge 144 of the chassis 102 and the inner edge 107*b* of the first belt 106 and/or may be positioned longitudinally between the first lateral edge 144 of the chassis 102 and the outer edge 107*a* of the first belt 106. In some configurations, the first accessibility opening 802*a* may extend across the first longitudinal edge 128 and/or the first lateral edge 144 of the chassis 102, and/or the second accessibility opening 802*b* may extend across the second longitudinal edge 130 and/or the first lateral edge 144 of the chassis 102.

Figure 7B:
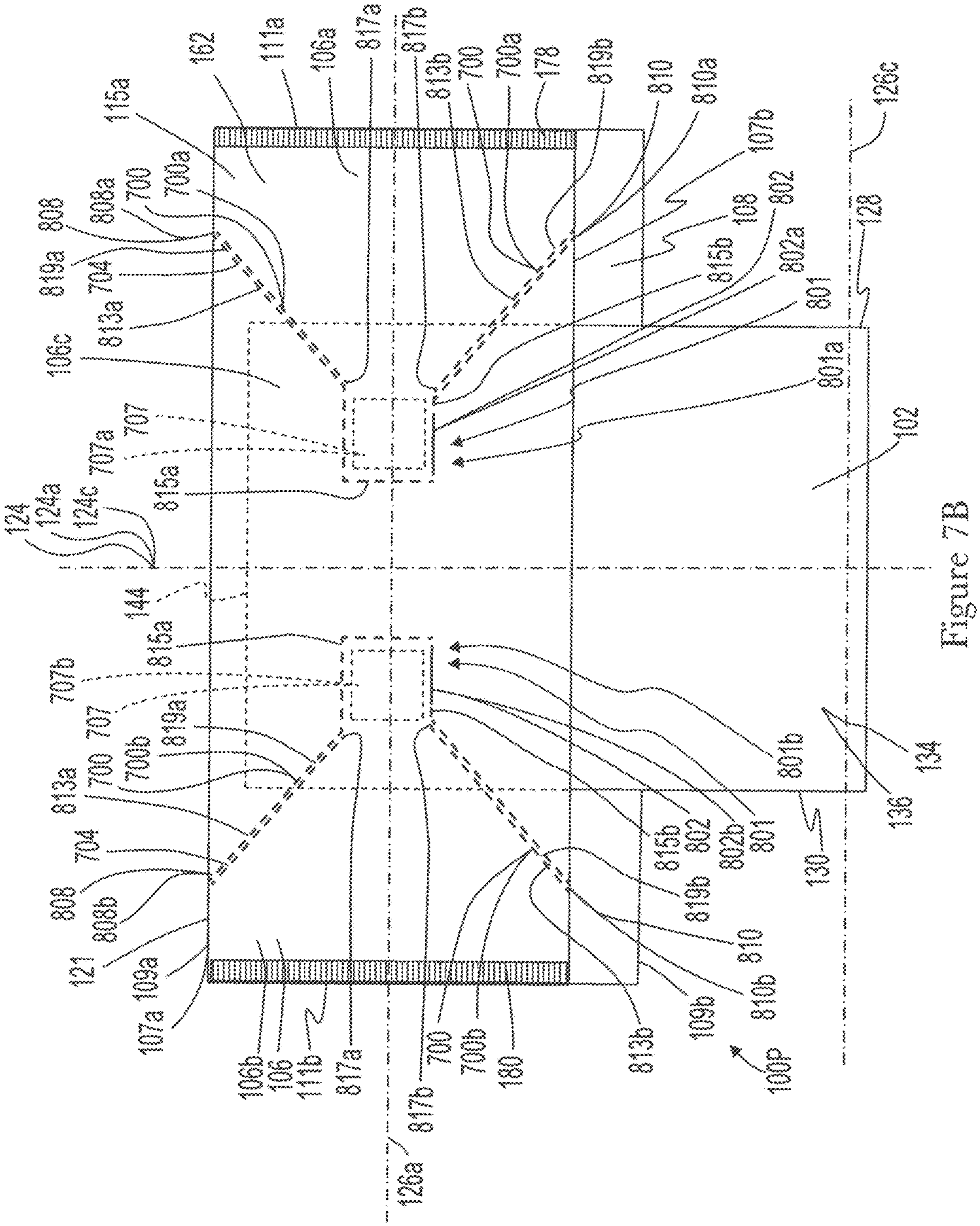
FIG. 7B is a front plan view of another configuration of a diaper pant with frangible pathways having an accessibility opening positioned longitudinally between the fastener component and an inner edge of the first belt.

It is also be appreciated that accessibility openings 802 may be located in various positions relative to fastener components 707. For example, in some configurations, the accessibility opening 802 may be positioned longitudinally between the fastener component 707 and the inner edge 107*b* of the first belt 106, such as shown in FIG. 7B. In some configurations, the accessibility opening 802 may be positioned longitudinally between the fastener component 707 and the outer edge 107*a* of the first belt 106. In some configurations, the accessibility opening 802 may be positioned laterally inboard of the fastener component 707. It is also to be appreciated that more than one accessibility opening 802 may be located adjacent a fastener component 707. As discussed in more detail below, the accessibility opening 802 also be configured to extend partially or entirely through a fastener component 707 and may divide a fastener component 707 into two or more parts.

As mentioned above, the accessibility opening 802 may comprise slits and/or openings in the first belt 106 and may be curved and/or straight. It is to be appreciated that the accessibility openings 802 may also be oriented in various ways. For example, the accessibility opening 802 may be generally oriented perpendicularly relative to the outer edge 107*a* and/or the inner edge 107*b* of the first belt 106. In some configurations, the accessibility opening 802 may be generally oriented parallel relative to the outer edge 107*a* and/or the inner edge 107*b* of the first belt 106. In some configurations, the accessibility opening 802 may comprise a slit that extends along a line in a lateral direction to define an angle from about 0 degrees to about 45 degrees with respect to the outer edge 107*a* and/or the inner edge 107*b* of the first belt 106, specifically reciting all 1 degree increments within the above-recited range and all ranges formed therein or thereby. In some configurations, the accessibility opening 802 may define a length dimension in the range of about 5 mm to about 50 mm, specifically reciting all 0.1 mm increments within the above-recited range and all ranges formed therein or thereby.

Figure 8A:
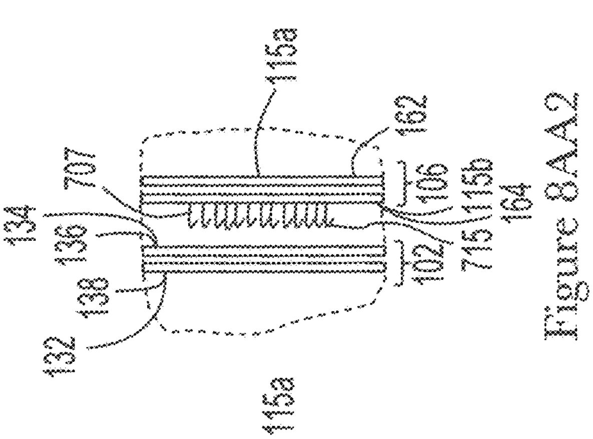
FIG. 8A is a detailed view of a fastener component configuration of FIG. 6A.
Figure 8A:
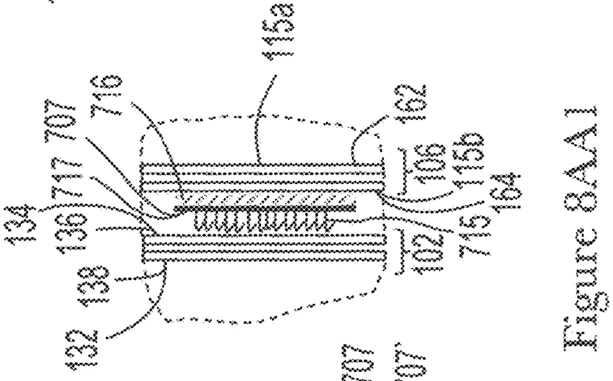
Figure 8A:
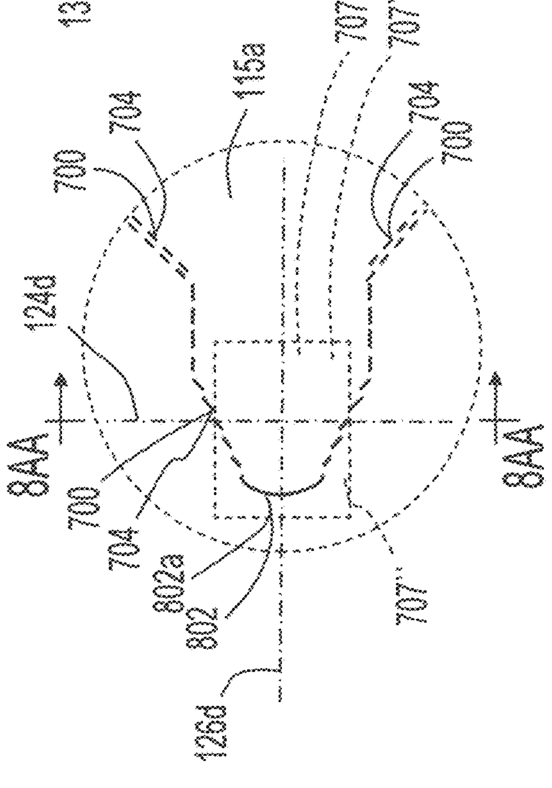
Figure 9B:
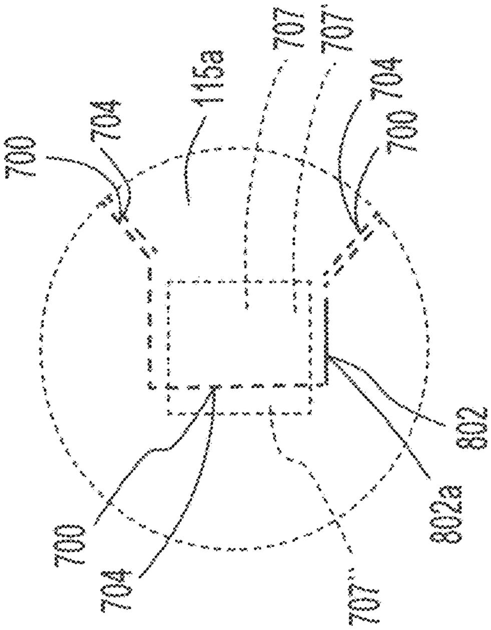
FIG. 9B is a detailed view of another fastener component configuration.
Figure 9A:
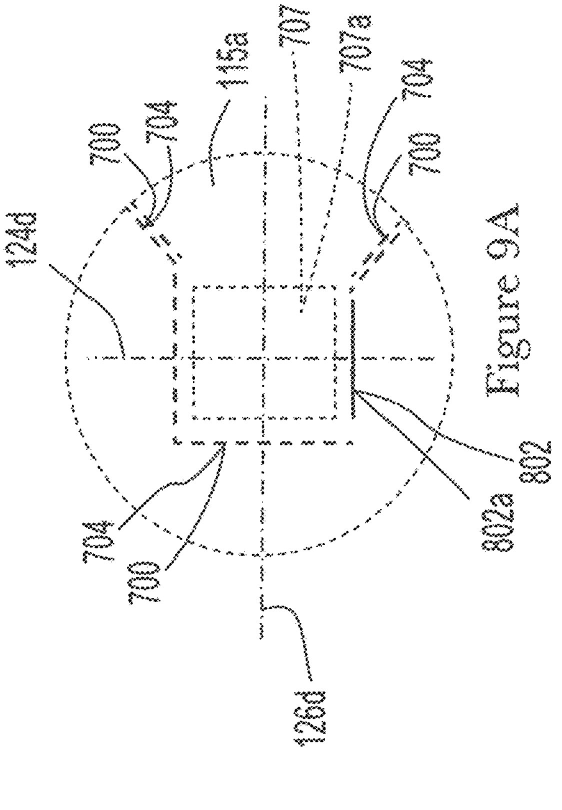
FIG. 9A is a detailed view of another fastener component configuration of FIG. 7A.

As discussed above, the diaper pant 100P may include one or more fastener components 707 adapted to refastenably connect with at least one other component of the diaper pant 100P in a disposal configuration. It is to be appreciated that the fastener components 707 may be configured in various shapes and sizes, and may be located in various positions relative to other components of the diaper pant 100P. As shown in FIGS. 8A and 9A for example, the fastener components 707 may comprise a lateral centerline 126*d* oriented substantially parallel to the lateral centerline 126*a* of the first elastic belt 106 and/or the lateral centerline 126*b* of the second elastic belt 108 and/or the lateral centerline 126*c* of the chassis 102. The fastener components 707 may comprise a longitudinal centerline 124*d* oriented substantially parallel to the longitudinal centerline 124*a* of the first elastic belt 106 and/or the longitudinal centerline 124*b* of the second elastic belt 108 and/or the longitudinal centerline 124*c* of the chassis 102.

As shown in FIG. 8AA1, in some configurations, fastener components 707 may be positioned on and connected with the wearer facing surface 115*b* of the first elastic belt 106 and/or the second elastic belt 108 in a region where the first elastic belt 106 and/or second elastic belt 108 overlaps the chassis 102. In some configurations, the fastener component 707 may be sandwiched between the second substrate 164 of the first elastic belt 106 or the second elastic belt 108 and the backsheet 136 of the chassis 102. In some configurations, such as shown in FIG. 8AA1, the fastener component 707 comprises hooks 715 protruding from a base 717, and the hooks 715 extend from the first belt 106 toward the backsheet 136. The fastener component 707 may be configured as a separate discrete element that may be connected with the wearer facing surface 115*b* of the first belt 106 in various ways. For example, as shown in FIG. 8AA1, adhesive 716 may connect the base 717 of the fastener component 707 with wearer facing surface 115*b* of the first belt 106. It is to be appreciated that the fastener component 707 may be connected with the first belt 106 by mechanical bonding in addition to or instead of adhesive. It is to be appreciated that the base 717 may be configured in various ways. For example, the base 717 may comprise a thermoplastic film. In some configurations, the base 717 may comprise a laminate with various layers bonded together, such as disclosed for example in U.S. Patent Publication No. 2021/0045931 A1. For example, the base 717 may comprise a thermoplastic film layer bonded with a nonwoven layer. It is to be appreciated that such layers may be bonded together in various ways, such as with adhesive, mechanical bonding, and/or extrusion bonding. In some configurations, the fastener component 707 may be integrally formed from materials of the first belt 106, such as shown for example in FIG. 8AA2, or may be integrally formed from materials and attached with the first belt.

As previously mentioned, it is to be appreciated that the fastener components 707 referred to herein may be configured in various ways, such as hooks, loops, and/or adhesive. For example, the fastener component 707 may comprise hook elements or adhesive adapted to refastenably connect with another surface of the diaper pant 100P. In some configurations, the fastener component 707 may comprise loop elements adapted to refastenably connect with hook surface on the diaper pant 100P. The fastener component 707 may be a separate element connected with the elastic belt 106 in various ways, such as mechanical bonding, adhesive bonding, or both. In some configurations, the fastener component 707 may be integrally formed from materials of the elastic belt 106, 108. In some configurations, the fastener component 707 may be printed and/or comprise materials of various different colors such that the fastener component 707 may be visible from outside the diaper pant 100P.

In some configurations, the fastener component 707 may comprise a hook material adapted to refastenably engage with substrates, such as nonwovens for example, on an exterior surface of the diaper pant 100P. For example, the fastener component 707 may comprise a substrate comprising hooks, with the substrate bonded to the elastic belt 106, 108, such as the second substrate 164, which may be in the form of a nonwoven. It is to be appreciated that the substrate may be bonded to the elastic belt 106, 108 in various ways, such as for example, with mechanical bonds, thermal bonds, ultrasonic bonds, and/or adhesive bonds or combinations thereof. In some configurations, hooks may be integrally formed from the second substrate 164, which may be in the form of a nonwoven. The fastener component 707 may comprise one material or a combination of two or more materials arranged in at least partially overlapping configuration. In some configurations, the fastener component 707 may comprise other fastener types as known in the art.

It is to be appreciated that the fastener component 707 may comprise any of a wide variety of shapes, including rectangles or other polygons, circles, ovals, shapes having exterior convexities or concavities or combinations thereof, or one or a plurality of lines or geometric shapes forming an array. It is to be appreciated that the fastener component 707 may comprise various sizes. For example, in some configurations, the fastener component 707 may have a lateral width of between about 5 mm and about 100 mm, specifically reciting all 0.1 mm increments within the above-recited range and all ranges formed therein or thereby. In some configurations, the fastener component 707 may have a longitudinal length of between about 10 mm and about 100 mm, specifically reciting all 0.1 mm increments within the above-recited range and all ranges formed therein or thereby. The fastener component 707 may be aligned parallel the lateral centerline 126*a*, 126*b* of the elastic belt 106, 108 or may be oriented at an angle relative the longitudinal centerline 126*a*, 126 of the elastic belt 106, 108 of between 0 and 90 degrees. The fastener component 707 may comprise an array of two or more spaced-apart fastening elements. The fastener component 707 may have a color that is visible through any layers of the elastic belt 106, 108 on which the fastener component 707 is located. The elastic belt 106, 108 and/or chassis 102 may include printing or other indicia highlighting to a caregiver the location, function, and/or usage of the fastener component 707. The bond, or bond pattern, attaching the fastener component 707 to the elastic belt 106, 108 may be visually or tactilely distinct from the surrounding belt material in order to provide the caregiver a signal or a mechanical grip advantage.

As shown for example in FIG. 6B, a portion of the chassis 102 may overlap the inner wearer facing surface 115*b* of the first belt 106 to define a chassis overlap region 850. As such, the chassis overlap region 850 may extend laterally between the first longitudinal edge 128 and the second longitudinal edge 130 of the chassis 102 and longitudinally between the first lateral edge 144 of the chassis 102 and the inner edge 107*b* of the first belt 106. To help prevent contact of the fastener component 707 with a wearer's skin while wearing the diaper pant 100P, the fastener components 707 may be positioned on and connected with the wearer facing surface 115*b* of the first elastic belt 106 and/or the wearer facing surface 117*b* of the second elastic belt 108 in the chassis overlap region 850 where the first elastic belt 106 and/or second elastic belt 108 overlaps the chassis 102. For example, the fastener component 707 may be sandwiched between the wearer facing surface 115*b* of the first belt 106 and the chassis 102. In some configurations, the fastener component 707 may be sandwiched between the second substrate 164 of the first elastic belt 106 or the second elastic belt 108 and the backsheet 136 of the chassis 102. In some configurations, the fastener component 707 may be positioned laterally between the first longitudinal side edge 128 and the second longitudinal side edge 130 of the chassis 102. The fastener component 707 may also be positioned longitudinally between the first lateral edge 144 of the chassis 102 and the inner edge 107*b* of the first belt 106. As shown in FIG. 9A, the fastener component 707 may be positioned adjacent the frangible pathway 700. In the configuration shown in FIG. 8A, both the frangible pathway 700 and the accessibility opening 802 may extend through the fastener component, effectively dividing the fastener component 707 into a first fastener part 707' and a second fastener part 707". The accessibility openings 802 shown in FIG. 8A may comprise slits that are generally oriented in a longitudinal direction. In addition, the accessibility opening 802 extends through the fastener component 707 and may be positioned entirely within a perimeter of the fastener component. It is to be appreciated that such slits may be straight and/or curved. The accessibility opening 802, which may be considered part of the frangible pathway 700, may be positioned adjacent the fastener component 707. As such, the frangible pathway 700 may partially surround the fastener component 707. In some configurations, such as shown in FIGS. 8A and 9B, the frangible pathway 700 and/or accessibility opening 802 may extend through the fastener component 700, effectively dividing the fastener component 707 into a first fastener part 707' and a second fastener part 707". As discussed above, the first fastener part 707' is separated from the second fastener part 707" as the frangible pathway is torn. When completing the tearing operation, the first belt zone 831 and the second belt zone 832 will include first fastener parts 707', and the third belt zone 833 will include second fastener parts 707" separated from respective first fastener parts 707' during the tearing of frangible pathways 700.

Figure 7C:
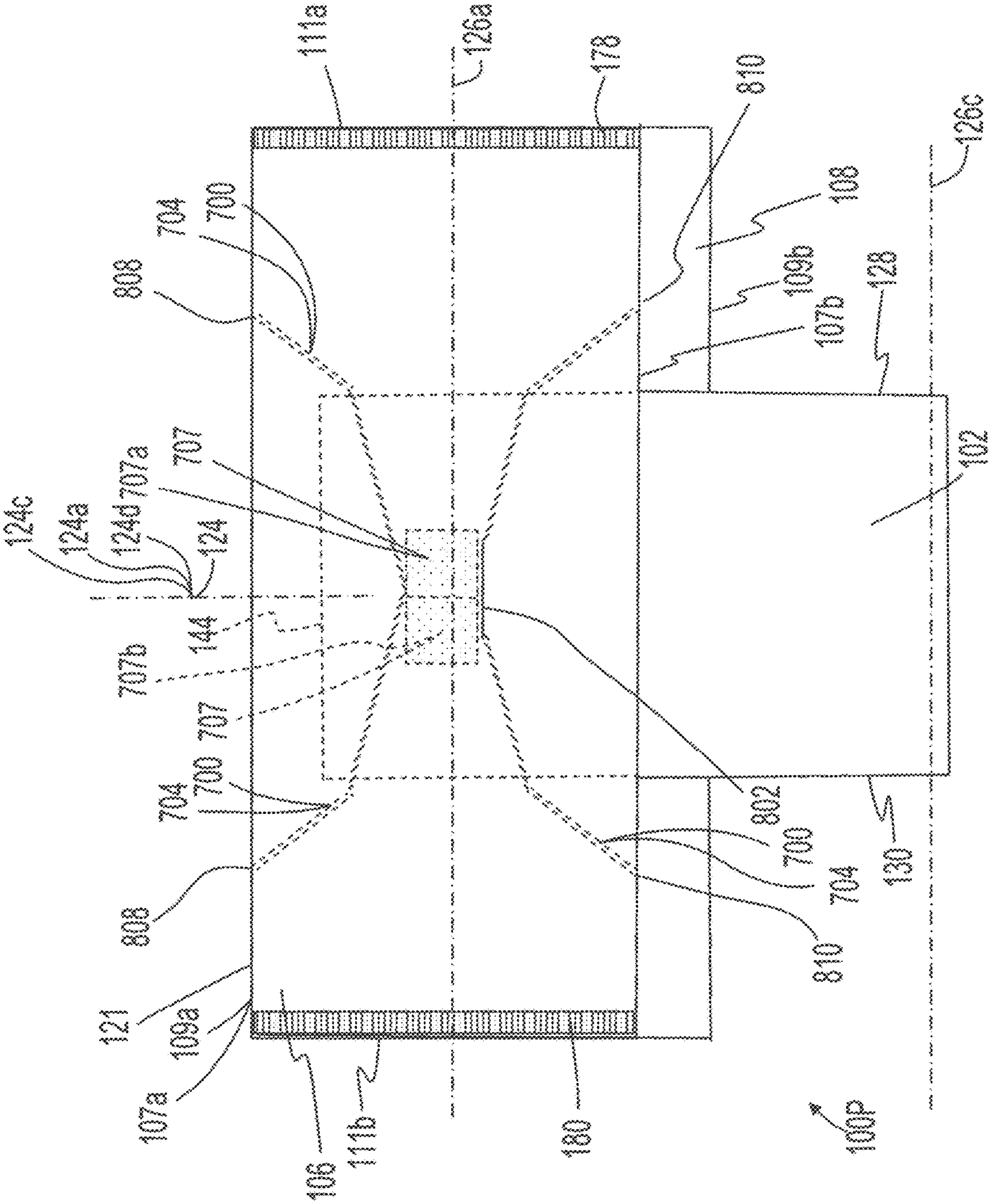
FIG. 7C shows a front plan view of a diaper pant with another configuration of frangible pathways.

In another configuration shown in FIG. 7C, the diaper pant 100P may comprise one fastener component 707 joined to the wearer facing surface 115*b* of the first belt 106 in a location overlapping the longitudinal centerline 124*c* of the chassis 102. The longitudinal centerline 124*d* of the fastener component 707 may be coincident with, or in proximity of, the longitudinal centerline 124*c* of the chassis 102. The frangible pathway 700 may divide fastener component 707 into the first fastener component 707*a* and the second fastener component 707*b* of substantially similar size and geometry. An accessibility opening 802 may be disposed at, or in proximity of, a longitudinally inboard lateral edge of the fastener component 707. Longitudinally outboard the lateral edges of the fastener component 707, the frangible pathway 700 may extend in longitudinal and lateral directions to the waist edge 121 and inner edge 107*b* of the first belt 106. A caregiver or wearer may access and grasp the fastener component 707 through the accessibility opening 802 and subsequently separate the frangible pathway 700 into the first and second fastener components 707*a*, 707*b*.

Figure 7D:
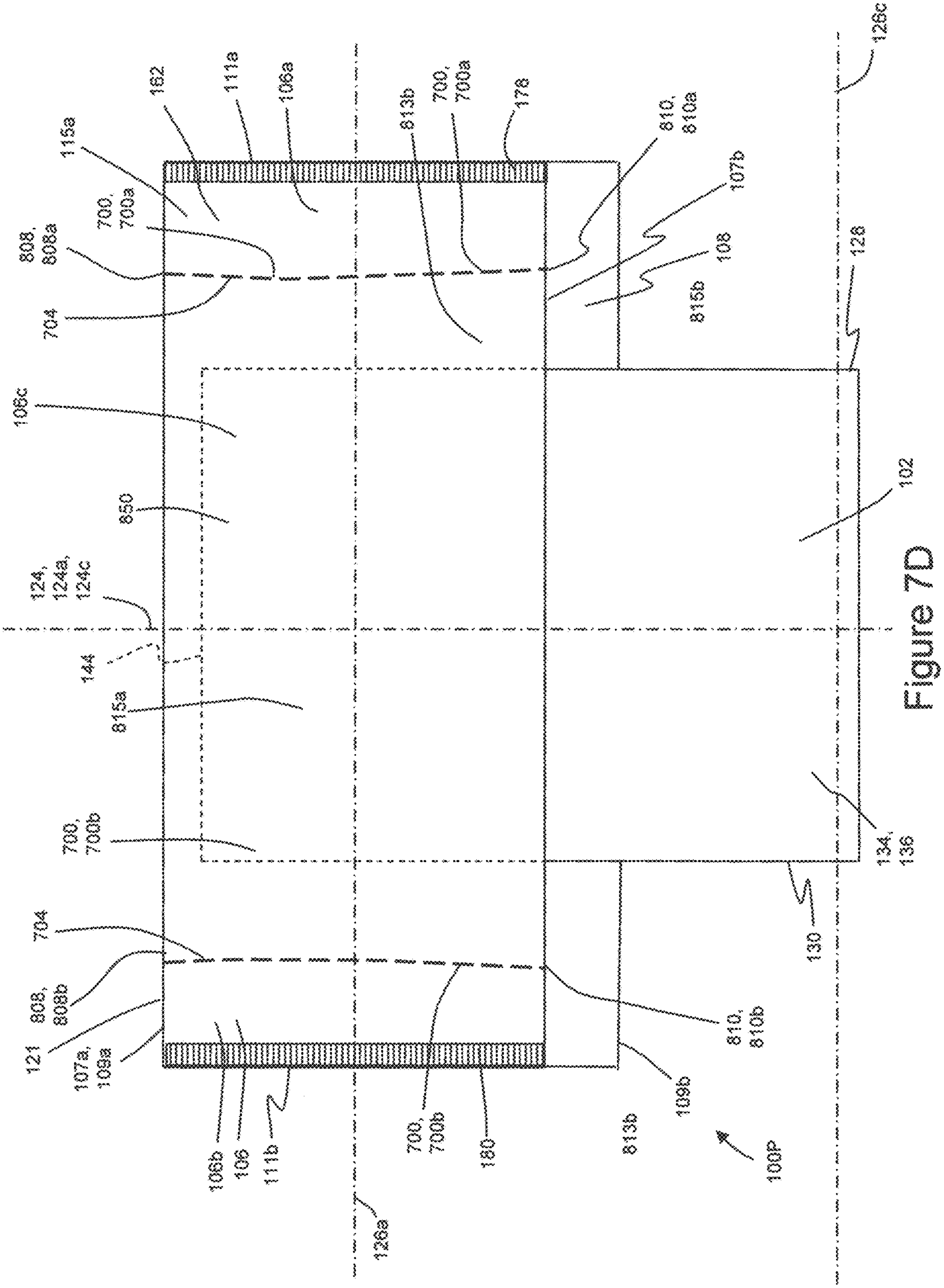
FIG. 7D shows a front plan view of a diaper pant with another configuration of frangible pathways.

In other configurations, such as shown in FIG. 7D, the absorbent article 100P may or may not include fastener components 707 adjacent frangible pathways 700. In some configurations, the frangible pathways 700 may be positioned entirely outside the chassis overlap region 850 and may not overlap the chassis 102. The first frangible pathway 700*a* may be entirely positioned laterally between the first longitudinal edge 128 of the chassis 102 and the first side seam 178, and the second frangible pathway 700*b* may be entirely positioned laterally between the second longitudinal edge 130 of the chassis 102 and the second side seam 180.

It is to be appreciated that absorbent articles herein may be assembled in various ways utilizing various types of apparatuses configured to carry out various transformations in various orders of assembly. As described in more detail below, the converting apparatuses 300 shown in FIGS. 10-27 may operate to provide and advance an elastic laminate 200 and form frangible pathways 700 and accessibility openings 802 in the elastic laminate 200 as well as cut elastic strands that extend through the frangible pathways. The elastic laminate 200 may also be slit and separated along the machine direction MD into lanes, such as for example, a first elastic laminate 200*a* and a second elastic laminate 200*b*. In further diaper pant assembly operations, a continuous length of chassis assemblies may be advanced and cut into discrete chassis 102. The discrete chassis 102 may be spaced apart from each other along the machine direction MD, and opposing waist regions of the spaced apart chassis 102 may be connected with the advancing first and second elastic laminates 200*a*, 200*b*. The chassis 102 may be folded to bring the first and second elastic laminates 200*a*, 200*b* into a facing relationship, and the first and second elastic laminates 200*a*, 200*b* are bonded together. The first and second elastic laminates 200*a*, 200*b* may then be cut in the cross direction CD through bonded regions to create discrete pant diapers 100P, such as shown for example in FIGS. 1-9B. As such, the first and second elastic laminates 200*a*, 200*b* may be converted into the first and second belts 106, 108 of the diaper pants 100P described above.

It is to be appreciated that various apparatuses and methods may be utilized to produce elastic laminates 200 according to the present disclosure that may be used to construct diaper components, such as elastic belts 106, 108. It is to be appreciated that the methods and apparatuses herein may be adapted to operate with various types of absorbent article assembly processes, such as disclosed for example in U.S. Patent Publication Nos. 2013/0255861 A1; 2013/0255862 A1; 2013/0255863 A1; 2013/0255864 A1; and 2013/0255865 A1; and PCT Publication No. WO2023/088179 A1, as well as U.S. patent application Ser. Nos. 18/214,564; 18/214,569; 18/214,573; 18/214,586; 18/214,548; 18/214,680; 18/214,603; 18/214,691; 18/214,750; 18/214,718; 18/342,054; and 18/342,058, which are all incorporated by reference herein.

As discussed in more detail below, elastic laminates 200 may be used as a continuous length of elastomeric belt material that may be converted into first and second elastic belts 106, 108, such as discussed above with reference to FIGS. 1-9B. For example, the elastic laminate 200 may comprise elastic material 167 that may correspond with the belt elastic material 167 interposed between a first substrate 162, also referred to as an outer layer 162, and a second substrate 164, also referred to as an inner layer 164. The elastic material 167 may be stretched and joined with the first and second substrates 162, 164 to produce an elastomeric laminate 200. Although the elastic material 167 is illustrated and referred to herein as elastic strands 168, it is to be appreciated that in some configurations, elastic material 167 may include one or more continuous lengths of elastic strands, ribbons, and/or films. As such, a plurality of stretched elastic strands 168 may be positioned and bonded between the first substrate 162 and the second substrate 164. The elastic strands 168 may be arranged so as to correspond with the outer waist elastics 170 and the inner waist elastics 172 discussed above with reference to the first and second elastic belts 106, 108.

It is to be appreciated that in some configurations, the first substrate 162 and second substrate 164 herein may be defined by two discrete substrates or may be defined by folded portions of a single substrate. It is also to be appreciated that the first and second substrates 162, 164 may comprise edge configurations in various forms that may correspond with the waist edge configurations, such as for example, described above with reference to FIGS. 3-3C as well as disclosed in U.S. patent application Ser. No. 18/214,626 and U.S. Patent Publication No. 2022/0362068 A1, which are incorporated by reference herein.

It is to be appreciated that different components may be used to construct the elastomeric laminates 200 in accordance with the methods and apparatuses herein. As previously mentioned, the elastomeric laminates 200 may be converted into first and second belts 106, 108 discussed above, and as such, it is to be appreciated that components of the elastic laminate 200 may be assembled in various ways and various combinations to create various features that may described above with reference to the first elastic belt 106 and/or the second elastic belt 108. Such features may include, for example, substrate materials, Dtex values, bond patterns, aperture arrangements, elastic positioning, Average Dtex values, Average Pre-Strain values, rugosity frequencies, rugosity wavelengths, height values, and/or contact area. In some examples, the first and/or second substrates 162, 164 may include nonwovens and/or films. In addition, the elastic strands 168 may be configured in various ways and may have various decitex values such as described above. In some configurations, the elastic strands 168 may be configured with decitex values ranging from about 10 decitex to about 1000 decitex, specifically reciting all 1 decitex increments within the above-recited range and all ranges formed therein or thereby. It is also to be appreciated that the elastomeric laminates 200 assembled herein may include various quantities of elastic strands 168 spaced apart from each other by various distances and may include various decitex values. For example, the elastomeric laminates 200 herein may have various elastic densities, wherein the elastic density may be defined as decitex per elastomeric laminate width. For example, some elastomeric laminates 200 may have an elastic density from about 30 decitex/mm to about 150 decitex/mm, specifically reciting all 1 decitex/mm increments within the above-recited range and all ranges formed therein or thereby. In another example, the elastomeric laminates 200 herein may have various numbers of elastic strands arranged in the cross direction CD per meter of elastomeric laminate cross directional width. For example, some elastomeric laminates 200 may have from about 500 elastic strands/meter of elastomeric laminate width to about 2000 elastic strands/meter of elastomeric laminate width, specifically reciting all 1 elastic strand/meter increments within the above-recited range and all ranges formed therein or thereby.

Figure 10:
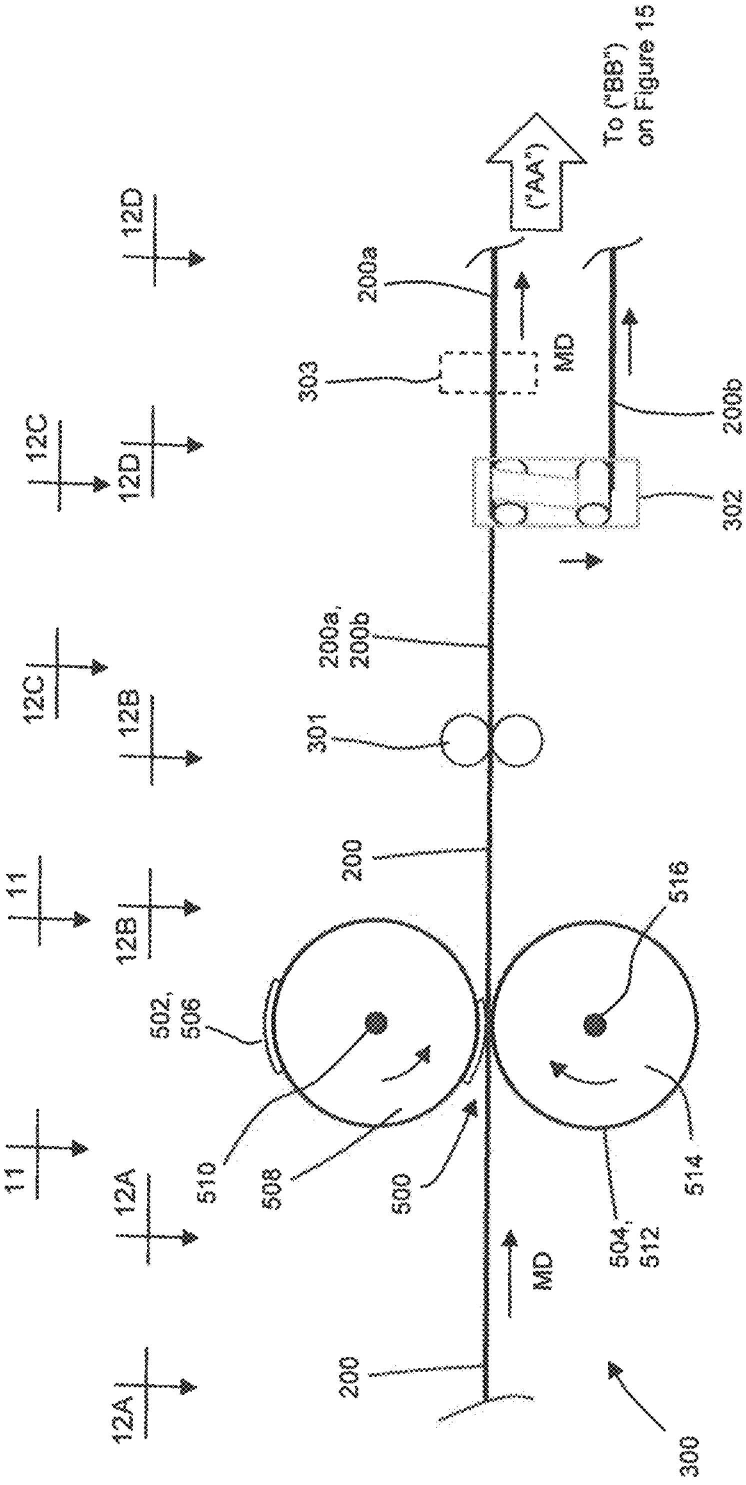
FIG. 10 is a schematic side view of a cutting apparatus adapted to form frangible pathways and accessibility openings in an elastomeric laminate.

Referring now to FIG. 10, an apparatus 300 may be adapted to form accessibility openings 802 and frangible pathways 700 in an elastic laminate 200. For example, the elastic laminate 200 may advance in a machine direction MD through a nip 500 between pattern surfaces 502 and a pressing surface 504. In turn, the pattern surfaces 502 and the pressing surface 504 may compress the elastic laminate 200 to form lines of weakness 704 and accessibility openings 802. It is to be appreciated that various configurations of pattern surfaces 502 and pressing surfaces 504 may be used with the apparatuses and methods herein. Such configurations may include features of the blades/units disclosed, for example, in U.S. Pat. Nos. 5,393,360; 7,708,849; 7,861,756; 7,777,094; and 8,440,043; and U.S. Patent Publication Nos. 2013/0261589 A1; 2018/0154533 A1; and 2019/0176450 A1, which are all incorporated by reference herein. As such, apparatuses 300 may be configured with die blade, flexible blade, and/or compression roll features, and may also include additional features to control blade-anvil gaps and/or force. In some configurations, at least one of the pressing surface 504 and the pattern surface 502 may be heated.

Figure 11:
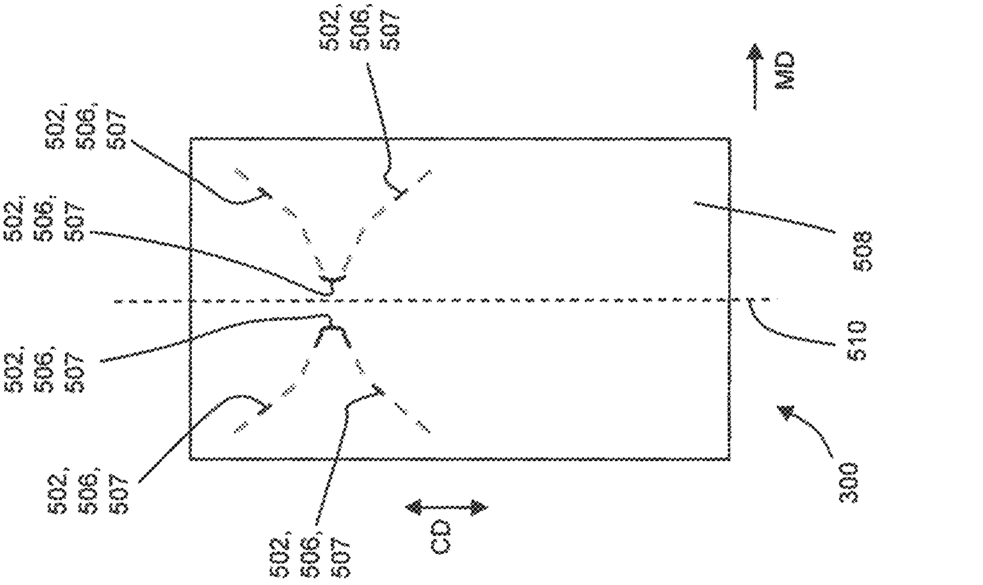
FIG. 11 is a view of the cutting apparatus of FIG. 10 taken along line 11-11.

It is to be appreciated that the pattern surfaces 502 may be configured in various ways. For example, as shown in FIG. 10, the pattern surfaces 502 may comprise protuberances 506 extending radially outward from a pattern roll 508. The pattern roll 508 may be adapted to rotate about a rotation axis 510 extending in the cross direction CD. As shown in FIG. 11, the pattern surfaces 502 and/or protuberances 506 may comprise blades 507 having widths, lengths, and shapes that may correspond with the widths, lengths, and shapes of the corresponding accessibility openings 802 and lines of weakness 704 to be formed in the elastic laminate 200 by the pattern surfaces 502.

It is also to be appreciated that the pressing surface 504 may be configured in various ways. For example, as shown in FIG. 10, the pressing surface 504 may comprise an outer circumferential surface 512 of an anvil roll 514 adapted to rotate about an axis of rotation 516 extending in the cross direction CD. In some configurations, the pressing surface 504 may comprise an energy transfer surface of an ultrasonic horn. As such, the apparatus 300 may include a horn and may be configured to impart ultrasonic energy to the elastic laminate 200 on the pattern surface 502. The ultrasonic device may apply energy to the horn to create resonance of the horn at frequencies and amplitudes so the horn vibrates rapidly in a direction generally perpendicular to the elastic laminate 200 being advanced past the horn on the pattern surface 502. Vibration of the horn may create lines of weakness 704 and/or accessibility openings 802 by generating heat to melt the substrate layers in areas supported by the pattern surfaces 502. Thus, the lines of weakness 704 and accessibility openings 802 may have shapes that correspond with and may mirror shape of the pattern surfaces 502.

It is to be appreciated that aspects of the ultrasonic bonding devices may be configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330. In some configurations, the ultrasonic bonding device may be configured as a linear oscillating type sonotrode, such as for example, available from Herrmann Ultrasonic, Inc. In some configurations, the sonotrode may include a plurality of sonotrodes nested together in the cross direction CD.

It is also to be appreciated that the elastic laminate 200 may be partially wrapped onto the pattern roll 508 and/or the anvil roll 514 when advancing through the nip 500. The extent that the elastic laminate 200 wraps around the pattern roll 508 and/or the anvil roll 514 may be referred to herein as a wrap angle and may be expressed in units of degrees. In some configurations, the wrap angle may be greater than zero degrees and less than or equal to 180 degrees, specifically reciting all 1 degree increments within the above-recited range and all ranges formed therein or thereby. In some configurations, the wrap angle may be greater 180 degrees.

Figure 12A:
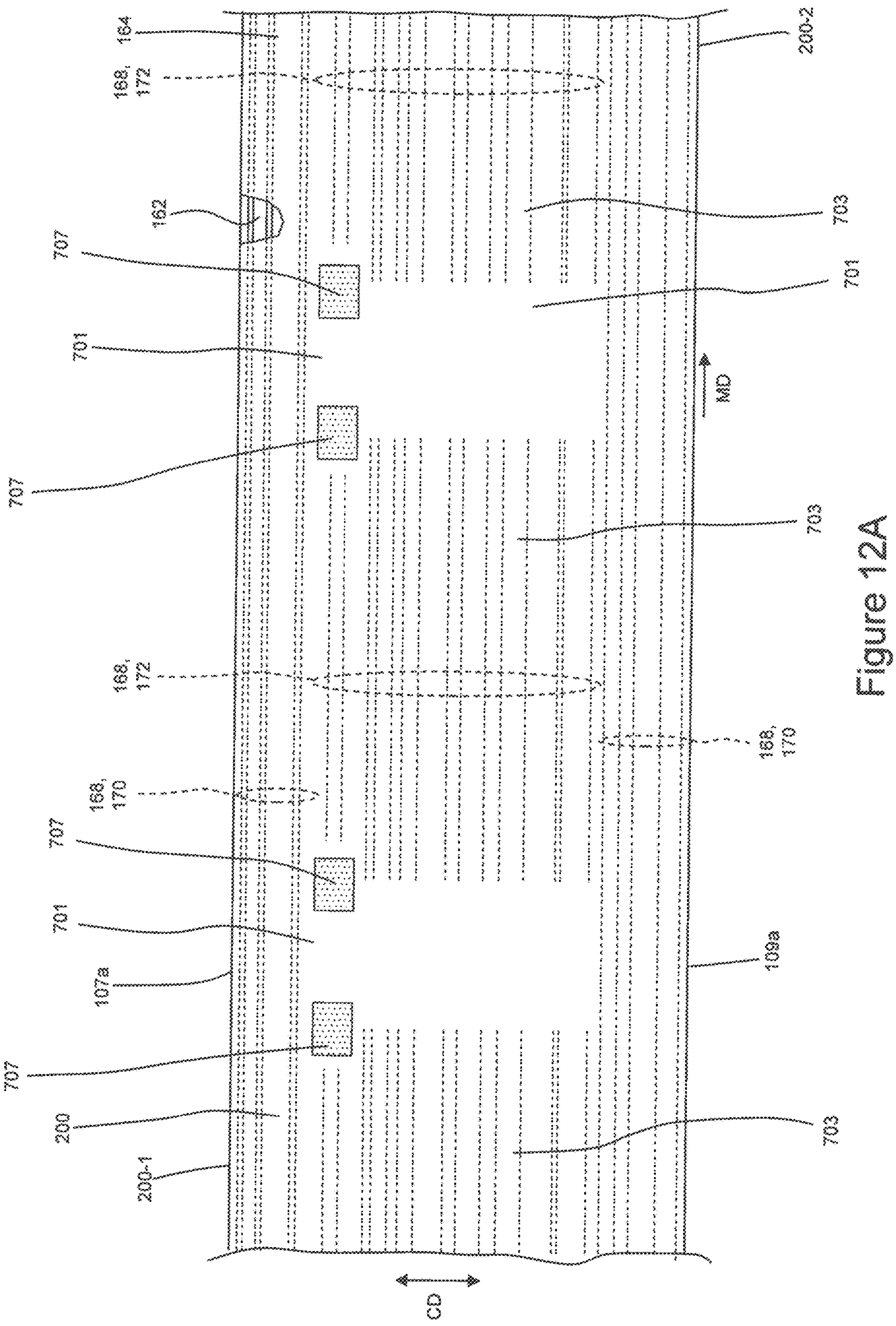
FIG. 12A is a view of the elastic laminate advancing in a machine direction upstream of the cutting apparatus FIG. 10 taken along line 12A-12A.

Referring now to FIGS. 10 and 12A, the elastic laminate 200 may comprise two or more layers of substrates 162, 164 and elastic strands 168 positioned and bonded between two layers of substrates, wherein the elastic strands extend in the machine direction. The elastic laminate 200 may further comprise a first edge 200-1 separated from a second edge 200-2 in a cross direction CD, wherein the elastic laminate comprises a laminate width defined by a distance extending in the cross direction between the first edge 200-1 and the second edge 200-2. As shown in FIG. 12A, the elastic laminate 200 may also comprise outer waist elastics 170 and inner waist elastics 172 in the form of elastic strands 168 positioned between and connected with a first substrate 162 and a second substrate 164. The inner and outer waist elastic strands 170, 172 extend in the machine direction.

Figure 12B:
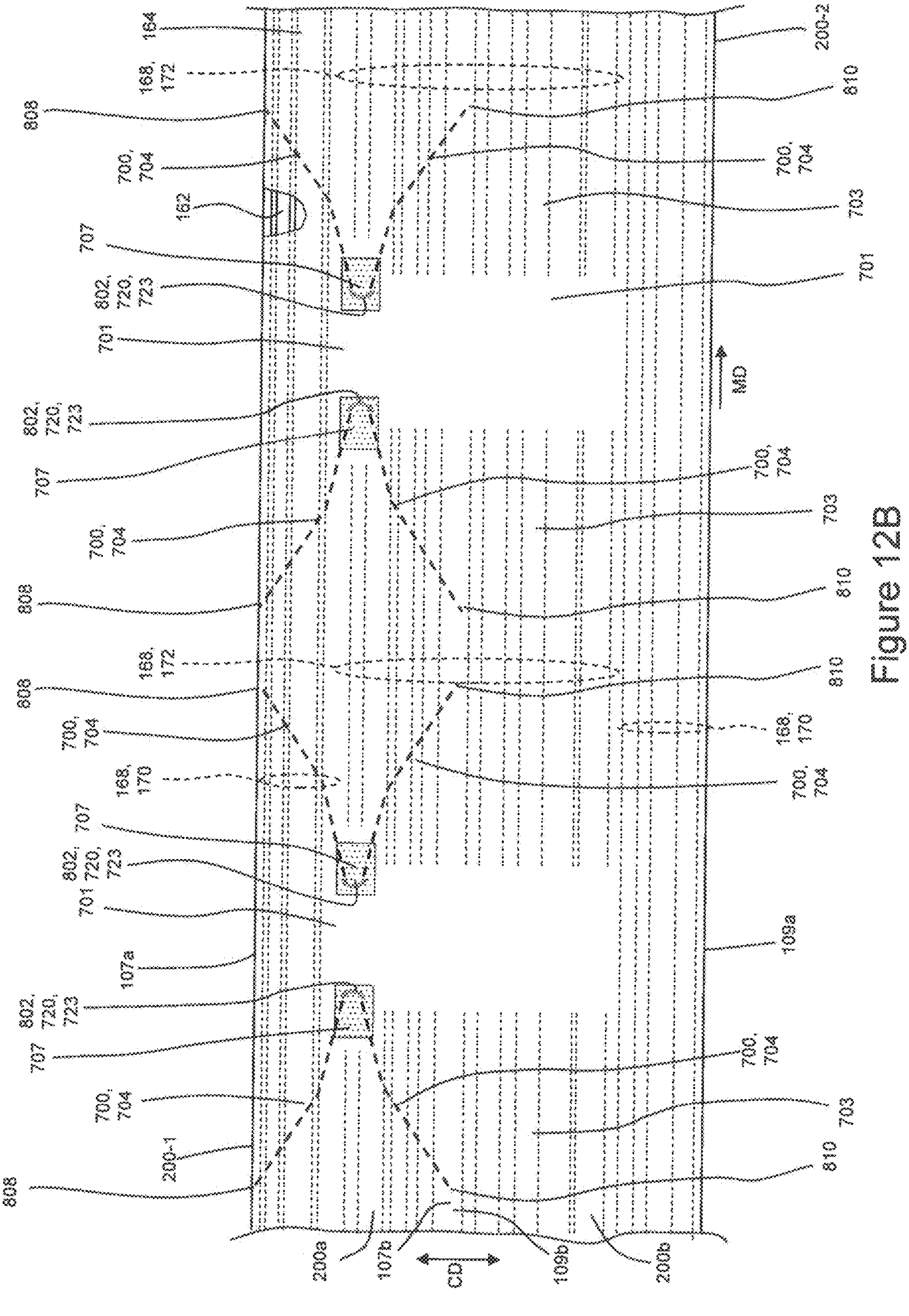
FIG. 12B is a view of the elastic laminate advancing in a machine direction from the cutting apparatus FIG. 10 taken along line 12B-12B.

As shown in FIGS. 10 and 12B, the elastic laminate 200 may advance through the nip 500 between the pattern surfaces 502 and the pressing surface 504 to form lines of weakness 704 of frangible pathways 700 and accessibility openings 802. The frangible pathway 700 may extend in the cross direction CD and may comprise one or more lines of weakness 704 that correspond with the size and shape of the pattern surfaces 502. It is also to be appreciated that the step of forming a line of weakness 704 may further comprise severing some elastic strands.

It is to be appreciated that some web handling/manufacturing operations may be completed upstream of, downstream from, or at the apparatus 300, such as tummy cutting operations that may create alternating low stretch zones 701 and high stretch zones 703 in the elastic laminate 200 as shown in FIG. 12B. In other examples, fastener components 707 may be bonded to the elastic laminate upstream of, downstream from, or at the apparatus 300. In some configurations, cut lines may be formed through the elastic laminate to form lines of weakness 704 in the elastic laminate 200 upstream of, downstream from, or at the apparatus 300.

With continued reference to FIGS. 10 and 12B, the apparatus 300 may be configured to form accessibility openings 802 and frangible pathways 700 extending in the cross direction CD between a distal terminus 808 and a proximal terminus 810. The frangible pathways 700 may be configured as the frangible pathways 700 described above, and as such, may comprise lines of weakness 704 as described above. As shown in FIGS. 10 and 12B, the apparatus 300 may be adapted to form a plurality of frangible pathways 700 and accessibility openings 802 intermittently spaced along the machine direction MD. The apparatus 300 may operate to form the accessibility openings 802 and/or lines of weakness 704 outside of, adjacent to, and/or through the fastener components 707. As such, the apparatus 300 may or may not operate to cut through both the elastic laminate 200 and the fastener components 707 when forming the accessibility openings 802. The inner waist elastic strands 172 and outer waist elastic strands 170 intersected by the frangible pathway 700 may also be severed at the lines of weakness 704. As shown in FIG. 12B, the distal terminus 808 may be positioned at or near the first edge 200-1 of the elastic laminate 200, and the proximal terminus 810 may be spaced from the distal terminus 808 in the cross direction CD and may be positioned in a central region of the elastic laminate 200 between the first edge 200-1 and the second edge 200-2.

Figure 12C:
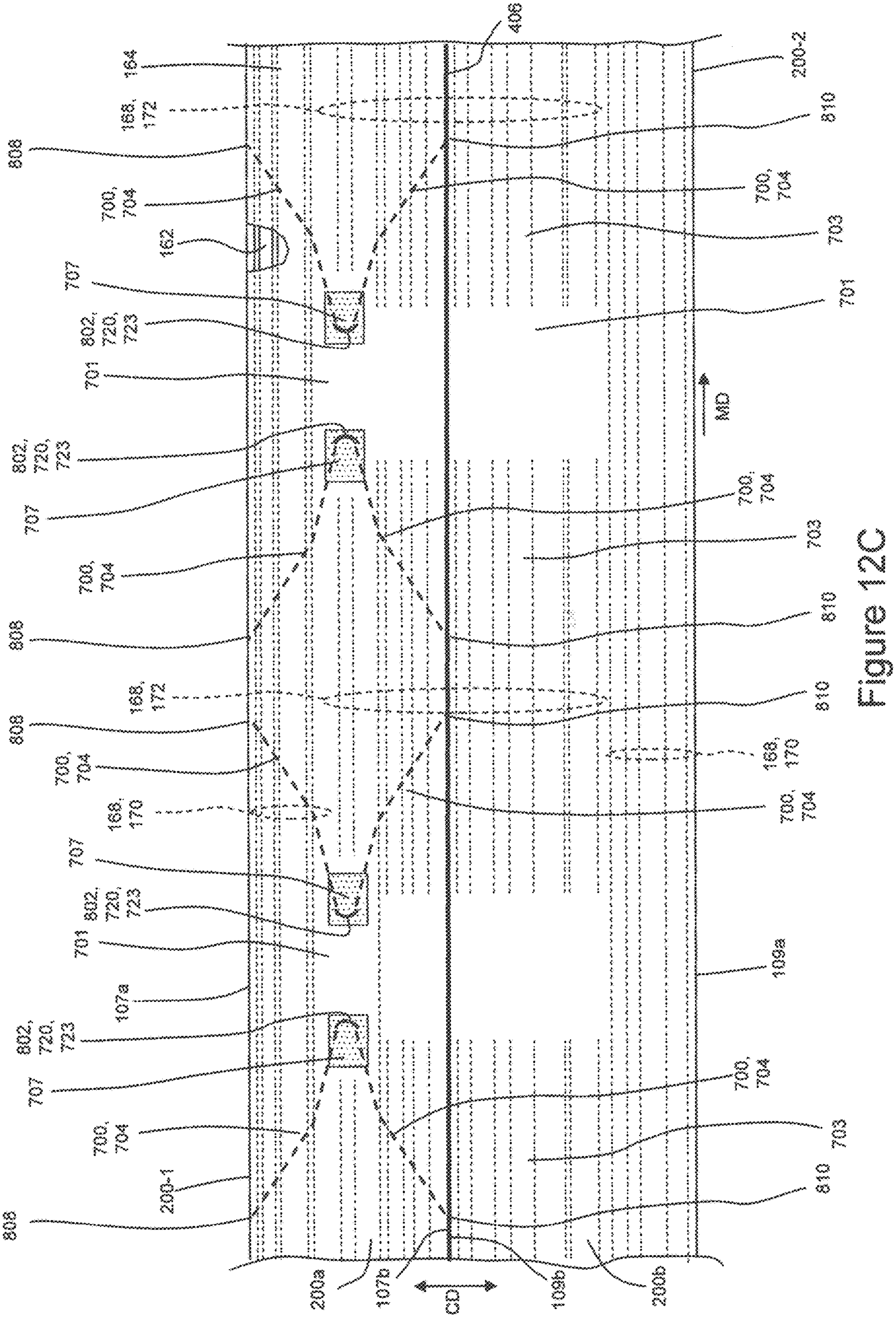
FIG. 12C is a view of the elastic laminate advancing from a slitting station from FIG. 10 taken along line 12C-12C.

Referring now to FIGS. 10 and 12C, the elastic laminate 200 may advance from the apparatus 300 to a slitting station 301 that may be configured to cut the elastic laminate 200 along the machine direction MD to define separate lanes of individual elastic laminates 200. For example, the slitting station 301 may comprise a slitting device that may comprise a knife and anvil that slits and separates the elastomeric laminate 200 along the machine direction MD into lanes, such as for example, a first elastic laminate 200*a* and a second elastic laminate 200*b*. It is to be appreciated slitting station 301 may be adapted to slit the elastomeric laminate 200 in various ways, such as for example with a shear slitting operation or a crush slit operation. In a crush slit operation, the first substrate 162 and the second substrate 164 may be bonded together during the slitting operation. It is to be appreciated that the slitting station 310 may be configured to perform slitting and/or cutting operations in various other ways, such as with lasers or ultrasonics, for example as disclosed in U.S. Patent Publication Nos. 2016/0354254 A1; 2016/0128874 A1; 2017/0266941 A1; 2017/0266057 A1; and 2017/0266056 A1, which are all incorporated by reference herein.

With continued reference to FIGS. 10 and 12, the slitting station 301 may be configured to cut the elastic laminate 200 in the machine direction MD along a cut line 406 that extends through the low stretch zones 701. As such, the first elastic laminate 200*a* and the second elastic laminate may each include low stretch zones 701. The cut line 406 may also be positioned to extend adjacent the proximal terminus 810 of the frangible pathways 700. As previously mentioned, the first elastic laminate 200*a* may be converted to the first elastic belt 106 and the second elastic laminate 200*b* may be converted to the second elastic belt 108 described above. As such, the first elastic laminate 200*a* may include an outer edge 200-1 and an inner edge 107*b*, and the second elastic laminate 200*b* may include an outer edge 200-2 and an inner edge 109*b*. It is to be appreciated that the outer edge 200-1 of the first elastic laminate 200*a* may correspond with the outer edge 107*a* of the first belt 106 or may be subject to subsequent operations such as waist edge folding to define the outer edge 107*a* of the first belt 106. It is also to be appreciated that the outer edge 200-2 of the second elastic laminate 200*b* may correspond with the outer edge 109*a* of the second belt 108 or may be subject to subsequent operations such as waist edge folding to define the outer edge 109*a* of the second belt 108.

Figure 12D:
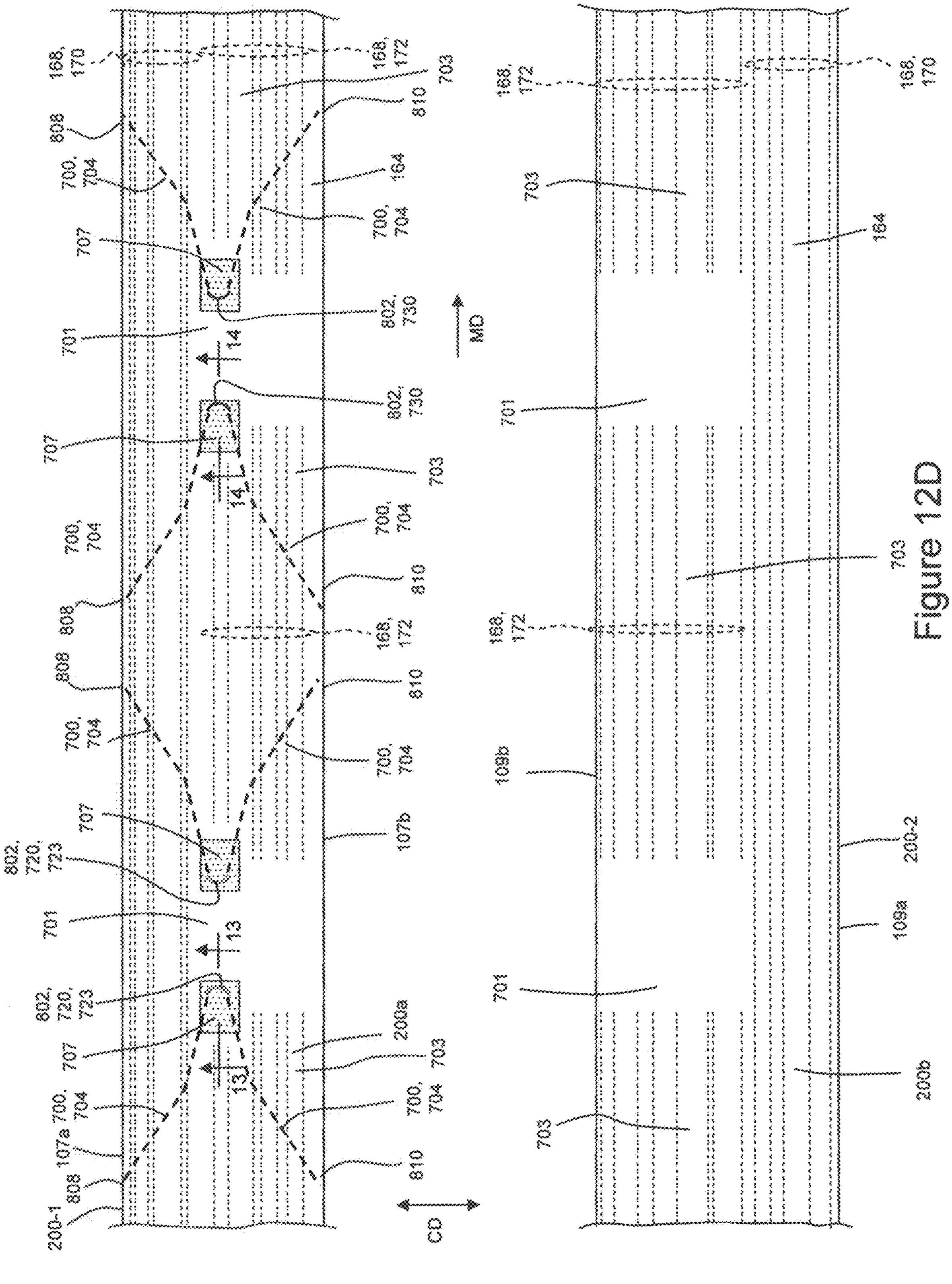
FIG. 12D is a view of first and second elastic laminates advancing from diverter and also wherein the first elastic laminate advances through a displacement apparatus from FIG. 10 taken along line 12D-12D.

As shown in FIGS. 10 and 12D, the first and second elastic laminates 200*a*, 200*b* may advance from the slitting station 310 through a diverter 302 that separates the first and second elastic laminates 200*a*, 200*b* from each other in the cross direction CD. In some configurations, the diverter 302 may separate the first and second elastic laminates 200*a*, 200*b* in the cross direction CD to define a gap between the inner edge 107*b* of the first elastic laminate 200*a* and the inner edge 109*b* of the second elastic laminate 200*b*.

As previously mentioned, the first elastic laminate 200*a* may correspond with the first elastic belt 106 and the second elastic laminate 200*b* may correspond with the second elastic belt 108 described above. As discussed in more detail with reference to FIGS. 18 and 19, when assembling diaper pants 100P, the first elastic laminate 200*a* and the second elastic laminate 200*b* may be separated from each other in the cross direction CD. In turn, opposing end regions of the chassis 102 may be connected with the low-stretch zones 701 in the first elastic laminate 200*a* and/or low stretch zones 701 in the second elastic laminate 200*b*. During subsequent assembly operations, the chassis 102 may be folded so as to position the first elastic laminate 200*a* into a facing relationship with the second elastic laminate 200*b*. The overlapping elastic laminates 200*a*, 200*b* may be bonded together, and subsequently, discrete diaper pants 100P may be formed by separating the first and second elastic laminates 200*a*, 200*b* into first and second belts 106, 108 by cutting along the cross direction CD through bonded regions of the first and second belt laminates 200*a*, 200*b*. As such, the bonded regions may be divided to define the first and second side seams 178, 180, respectively.

Figure 15:
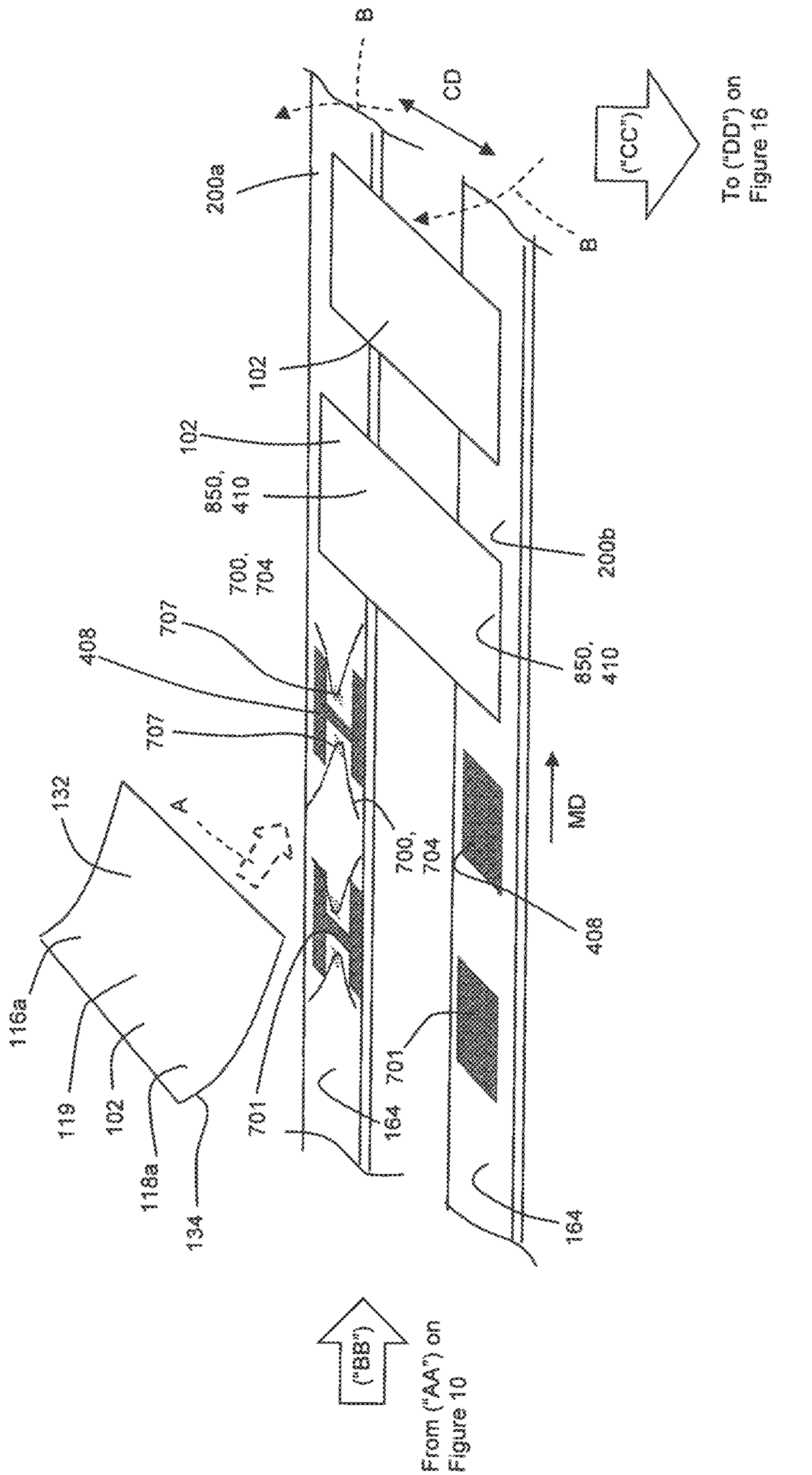
FIGS. 15 and 16 illustrate schematic representations of assembly transformations that may be utilized to assemble diaper pants 100P from the first and second elastic laminates.

As shown in FIG. 15, the first elastic belt laminate 200*a* and the second elastic belt laminate 200*b* are separated from each other in the cross direction CD and adhesive 408 may be intermittently applied to first elastic laminate 200*a* and the second elastic laminate 200*b*. As shown in FIG. 15, adhesive 408 may be applied in a pattern to define adherence regions 410. It is to be appreciated that adhesive 408 may be applied in various ways and to define various shapes, such as disclosed for example in U.S. patent application Ser. No. 18/214,573, which is incorporated herein by reference. Chassis 102 may be provided that comprise a body facing surface 132 and a garment facing surface 134, and an absorbent core 140 positioned between the body facing surface 132 and the garment facing surface 134 as discussed above. The chassis 102 may further comprise a first end region 116*a* and a second end region 118*a* separated in a cross direction CD from the first end region 116*a* by the crotch region 119. In turn, opposing end regions 116*a*, 118*a* of chassis 102 may be permanently bonded with the adhesive 408 in overlap regions 850 on the first elastic laminate 200*a* and/or a second elastic laminate 200*b* (represented by the dashed arrow "A"). In addition, the first end region 116*a* of the chassis 102 may be bonded with the first elastic laminate 200*a* overlapping the low-stretch zone 701, and the second end region 118*a* of the chassis 102 may be bonded with the second elastic laminate 200*b* overlapping the low-stretch zone 701. The first end region 116*a* of the chassis 102 may also be positioned between a first frangible pathway 700 and a second frangible pathway 700. As such, the first end region 116*a* of the chassis 102 may overlap portions of the first frangible pathway 700 and the second frangible pathway 700. In addition, the fastener components 707 may be positioned between the chassis 102 and the first elastic laminate 200*a*.

Figure 16:
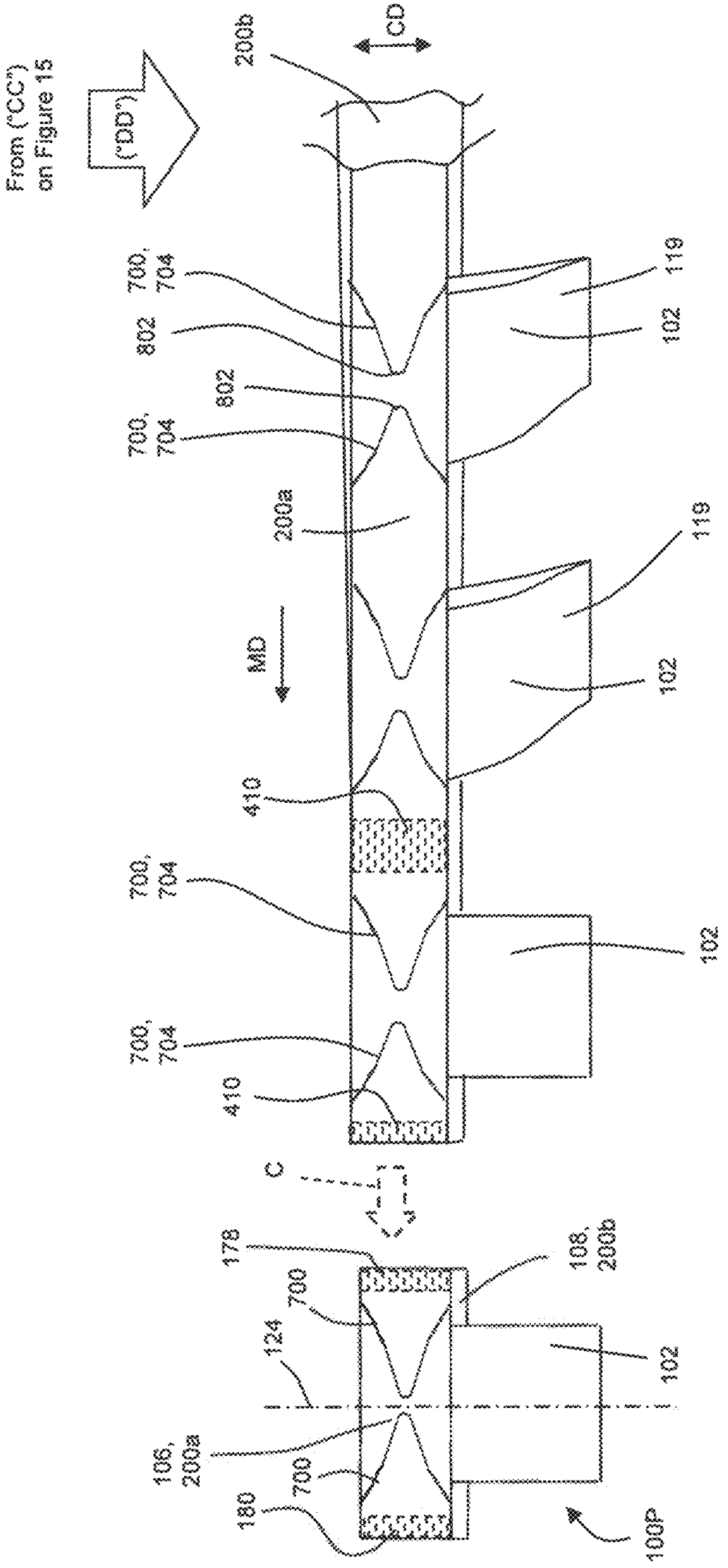

During subsequent assembly operations shown in FIGS. 15 and 16, the chassis 102 may be folded in the crotch region 119 (represented by the dashed arrow "B") so as to position the first elastic laminate 200*a* into a facing relationship with the second elastic laminate 200*b* as shown in FIG. 16. Bonds 410 may be applied to the overlapping belt laminates 200*a*, 200*b*. Subsequently, discrete diaper pants 100P may be formed by separating the first and second laminates 200*a*, 200*b* into first and second belts 106, 108 by cutting along the cross direction CD through the first and second laminates 200*a*, 200*b* adjacent the bonds 410 (represented by the dashed arrow "C"). As such, the bonds 410 may be divided to define the first and second side seams 178, 180, respectively.

It is to be appreciated that the elastic laminate 200 may be slit upstream or downstream of the apparatus 300. It is also to be appreciated that the apparatus 300 may form frangible pathways 700 in various ways and in various shapes and may be positioned in various locations on the first elastic laminate 200*a* and/or the second elastic laminate 200*b* relative to other features and/or elements formed in other process operations, such as for example: chassis-belt combining operations; waist edge folding operations; side seaming operations; and final knife cutting operations.

Figure 13:
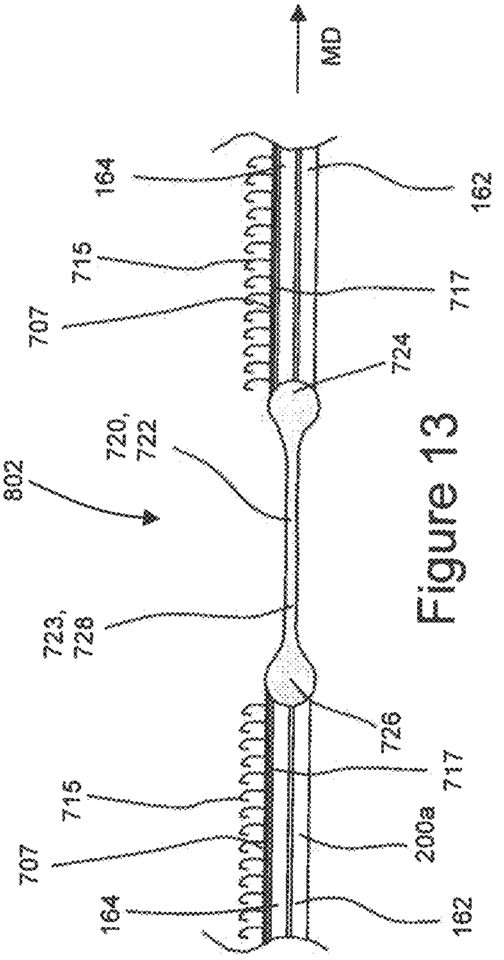
FIG. 13 is a sectional view of a bonded region of FIG. 12D upstream of the displacement apparatus, taken along line 13-13.

As discussed above, the converting apparatuses 300 may operate to form accessibility openings 802 and lines of weakness 704 in the elastic laminate 200. The accessibility openings 802 provide a location on the belt for a user to grab and help facilitate starting to tear the frangible pathway 700. The accessibility openings 802 may comprise slits and/or openings in the first belt 106 and may penetrate through some or all layers of the first belt 106. In addition, as discussed above with reference to FIGS. 8A and 8AA1, the accessibility opening 802 may positioned to extend across and through the fastener component 707. In some configurations, the fastener component 707 comprises hooks 715 protruding from a base 717. As such, when the elastic laminate advances through the nip 500, the pattern surface 502 and the pressing surface 504 may not operate to form an accessibility opening 802 comprising a cut line that penetrates through all layers of the elastic laminate 200. Rather, in some configurations, the pattern surface 502 and the pressing surface 504 may operate to form an accessibility opening 802 comprising a discrete bond 720 comprising a bond region 722 formed of materials of at least one substrate, such as for example one or more layers of substrates 162, 164 of the elastic laminate 200 that have been compressed and fused together. In some configurations, such as shown in FIGS. 12D and 13, the bond region 722 may comprise fused materials 723 of the first substrate 162, the second substrate 164, and the fastener component 707. As discussed above, in some configurations, the fastener component 707 may comprise hooks 715 protruding from a base 717. As such, the fused materials 723 of the bond region 722 may comprise materials of the base 717 and/or hooks 715 fused together with material of the elastic laminate 200. As such, the bond regions 720 may comprise mechanically thinned regions of belt material and/or fastener materials.

It is to be appreciated that the fused material 723 of the bond region 722 may comprise a leading edge region 724 and a trailing edge region 726 oriented in various ways with respect to the machine direction MD and/or the cross direction CD. For example, as shown in FIGS. 12D and 13, the fused material 723 of the bond region 722 may extend in the cross direction CD and may comprise a leading edge region 724 and a trailing edge region 726 separated from each other in the machine direction MD by a central region 728. In some configurations, the central region 728 of fused material 723 of the bond region 722 extends contiguously between the leading edge region 724 and the trailing edge region 726. If such fused materials 723 are left intact on an assembled diaper pant 100P, a user may have increased difficulties in utilizing the accessibility opening 802. For example, a user may have difficulties in inserting fingers through the accessibility opening 802 when attempting to start to tear the frangible pathway 700. In some instances, a user may have increased difficulties in visually detecting the accessibility opening 802.

Figure 14:
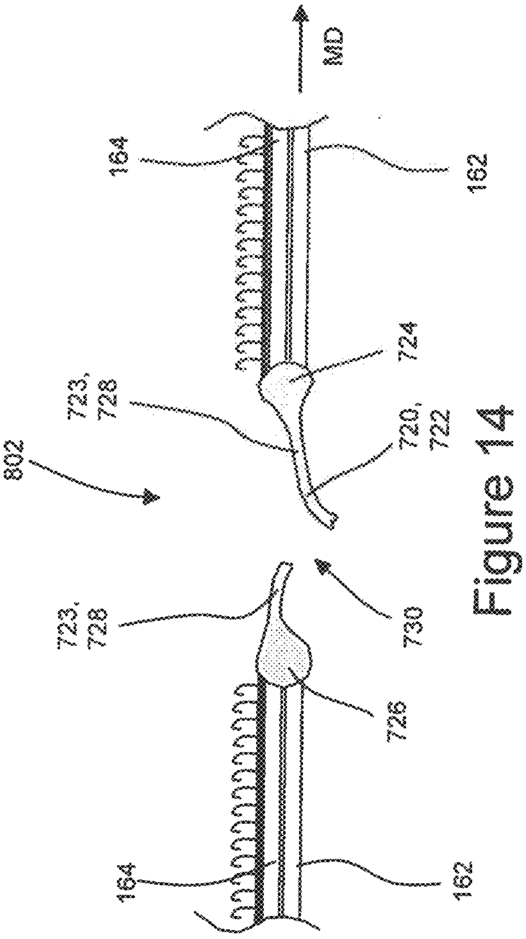
FIG. 14 is a sectional view of the bonded region of FIG. 12D downstream of the displacement apparatus, taken along line 14-14.

As such, in order to help ensure that the fused materials 723 of the bond region 722 are disrupted and/or broken, the first elastic laminate 200*a* may advance along a displacement apparatus 303, generically represented by a dash line rectangle in FIG. 10. As discussed in more detail below, the displacement apparatus 303 may operate to displace a region of the advancing first elastic laminate 200*a* where the bond region 722 is located. Such localized displacement the first elastic laminate 200*a* may operate to break or rupture the fused materials 723 of the bond region 722 to form a slit or aperture 730 through the first elastic laminate 200*a*. For example, the displacement apparatus 303 may operate to break the fused materials 723 in the central region 728 between the leading edge region 724 and the trailing edge 726. As such, the displacement apparatus 303 may operate to help complete the formation of a slit 730 in the accessibility opening 802, such as shown in FIGS. 12D and 14. Although the displacement apparatus 303 is described and depicted to act upon the first elastic laminate 200*a*, it is to be appreciated that the displacement apparatus 303 may be positioned to displace the elastic laminate 200 before being slit into the first and second elastic laminates 200*a*, 200*b*. Although the present discussion is framed mainly in the context of breaking bond regions 722 formed at the accessibility openings 802, it is to be appreciated that the displacement apparatus 303 may also be configured to break bond regions formed in lines of weakness 704 of frangible pathways 700.

Figure 17:
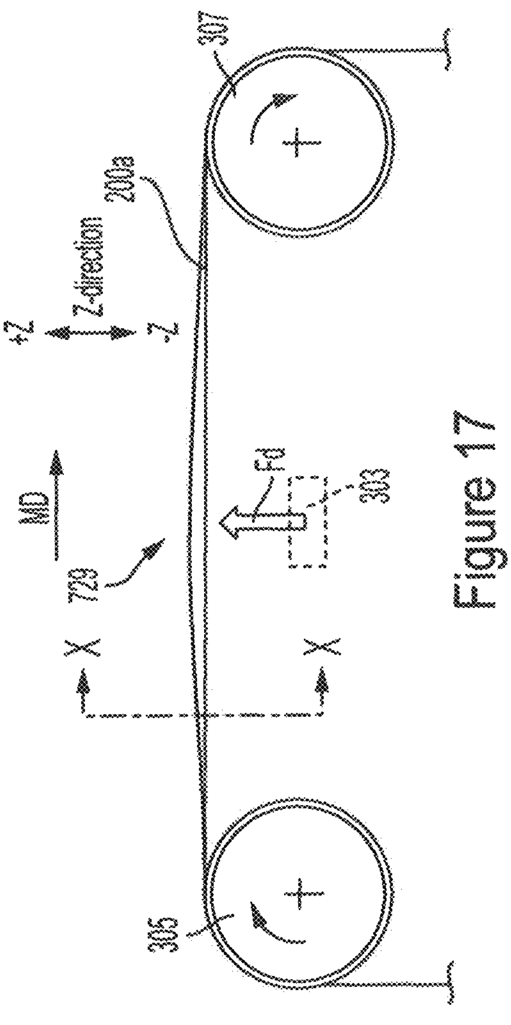
FIG. 17 is a schematic side view of the elastic laminate being subjected to a displacement force from the displacement apparatus.
Figure 18:
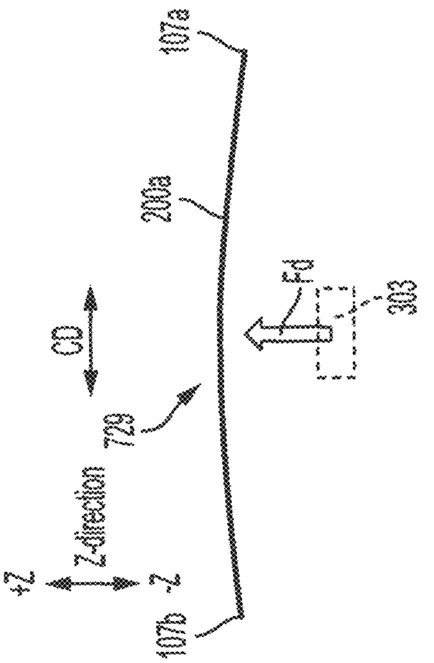
FIG. 18 is a sectional view of the elastic laminate of FIG. 17, taken along line X-X.
Figure 17A:
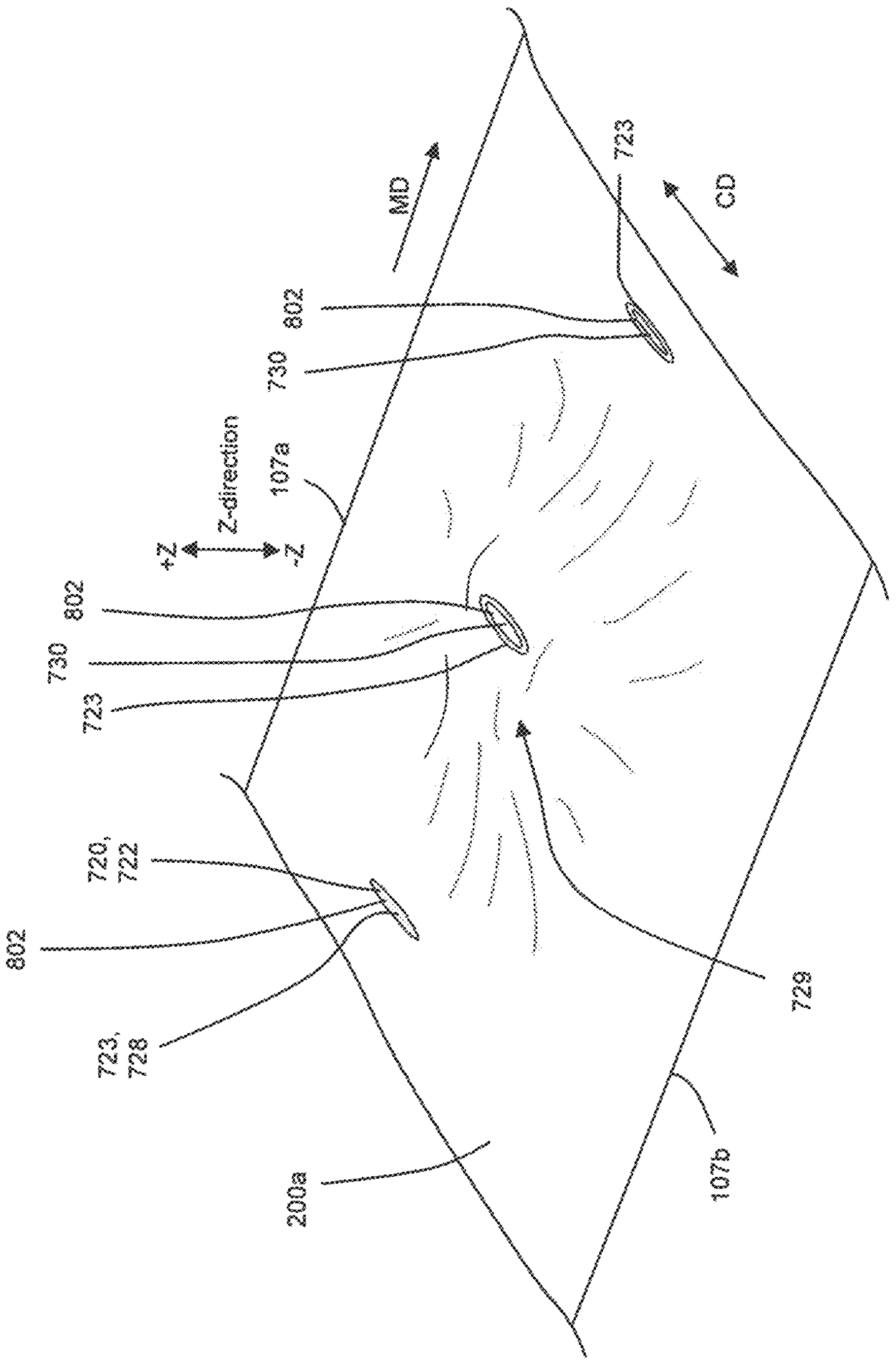
FIG. 17A is an isometric view showing a relative displacement of an elastic laminate in the Z-direction that causes fused material of a bond region to bend and break in a central region between a leading edge region and a trailing edge.

FIG. 17 is a schematic illustration of the first elastic laminate 200*a* advancing in a machine direction MD adjacent a displacement apparatus 303 between a first web metering device and a second web metering device, such as for example, arrangements of omega rolls. The displacement apparatus 303 may operate to apply a displacement force Fd on the first elastic laminate 200*a*. In particular, as shown in FIGS. 17, 17A, and 18, the displacement apparatus 303 may operate to apply a displacement force Fd in a Z-direction that is normal or perpendicular to both the machine direction MD and the cross direction CD. In turn, the displacement force Fd causes a region 729 of the first elastic laminate 200*a* where the bond region 722 is located to be displaced in the Z-direction relative to other regions of the first elastic laminate 200*a*, such as the first side edge 107*a* and the second side edge 107*b*. The relative displacement of the first elastic laminate 200*a* in the Z-direction causes the fused material 723 of the bond region 722 to bend and break in the central region 728 between the leading edge region 724 and the trailing edge 726, such as discussed above with reference to FIG. 14. The breakage or rupture the fused materials 723 of the bond region 722 forms form a slit or aperture 730 in the accessibility opening 802 penetrating through the first elastic laminate 200*a*.

Figure 19:
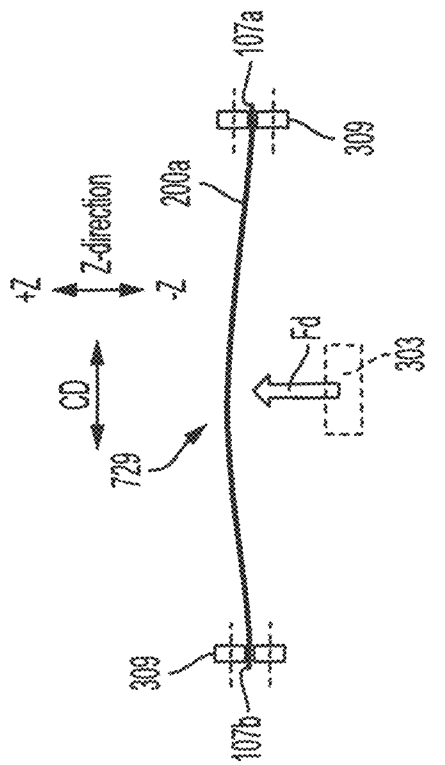
FIG. 19 is a sectional view of the elastic laminate of FIG. 17, taken along line X-X.

Referring now to FIG. 18, the first edge 107*a* and the second edge 107*b* of the first elastic laminate 200*a* are positioned in different elevations in the Z-direction than the region 729 of the first elastic laminate 200*a* where the displacement force Fd is applied. It is to be appreciated that the side edges 107*a*, 107*b* may also move in the Z-direction when applying the displacement force Fd, but may not move as much as the region 729 where the displacement force Fd is applied. In some configurations of the displacement apparatus 303, the side edges 107*a*, 107*b* and/or regions adjacent the side edges 107*a*, 107*b* of the first elastic laminate 200*a* may be held at a constant Z-direction elevation while the displacement force Fd is applied to the first elastic laminate 200*a*. For example, as shown in FIG. 19, regions of the first elastic laminate 200*a* adjacent the side edges 107*a*, 107*b* may advance between pairs of rollers 309 to maintain a constant Z-direction elevation of the side edges 107*a*, 107*b* while the displacement force Fd is applied to the first elastic laminate 200*a*.

It is to be appreciated that the displacement apparatus 303 may be configured in various ways to apply displacement forces Fd to the advancing first elastic laminate 200*a*. For example, as discussed below with reference to FIGS. 20A-25B, the displacement apparatus 303 may comprise a displacement surface 311, wherein the displacement surface 311 is positioned at a different Z-direction elevation than the Z-direction elevation of the first elastic substrate 200*a* at locations in the machine direction MD upstream and downstream of the displacement surface 311. In addition, the displacement surface 311 may be positioned at a different Z-direction elevation than the Z-direction elevation of the side edges 107*a*, 107*b* of first elastic substrate 200*a* at locations in the cross direction CD across from the displacement surface 311. As such, the displacement surface 311 may apply a displacement force Fd to the region 729 of the advancing first elastic laminate 200*a*. In turn, the region 729 of the first elastic laminate 200*a* where the bond region 722 is located is displaced in the Z-direction while the first elastic laminate 200*a* is in contact with the displacement surface 311, which causes the fused material 723 of the bond region 722 to bend and break to form a slit or aperture 730 in the accessibility opening 802 penetrating through the first elastic laminate 200*a*.

Figure 20A:
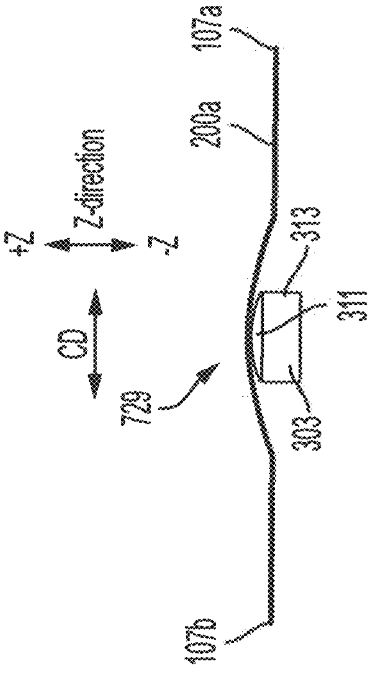
FIG. 20A a sectional view of the elastic laminate of FIG. 17, taken along line X-X advancing over a displacement apparatus comprising a stationary displacement member.
Figure 20B:
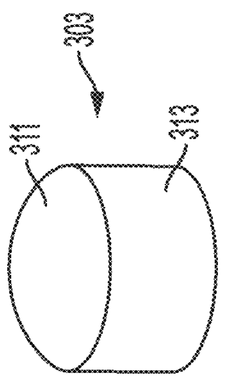
FIG. 20B is a perspective view of the stationary displacement member of FIG. 20A.

In some configurations, such as shown in FIGS. 20A and 20B, the displacement apparatus 303 may comprise a displacement member 313 comprising the displacement surface 311. The displacement member 313 and displacement surface 311 shown in FIGS. 20A and 20B may be stationary and may not advance in the machine direction MD. As such, the first elastic laminate 200*a* may advance in the machine direction MD relative to the displacement surface 311.

Figure 21A:
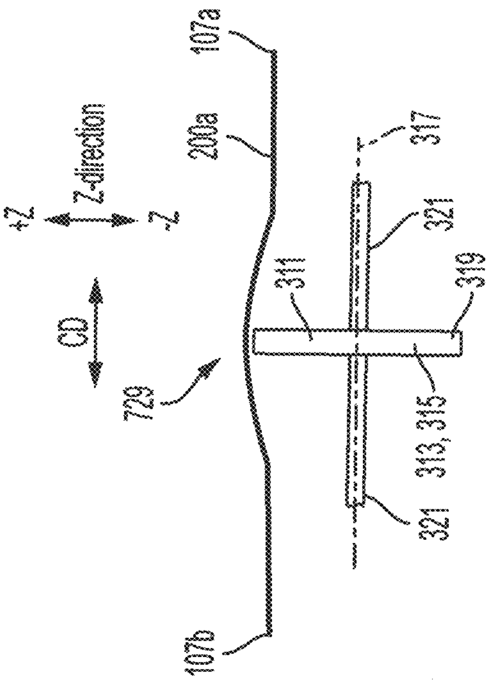
FIG. 21A a sectional view of the elastic laminate of FIG. 17, taken along line X-X advancing over a displacement apparatus comprising a rotatable displacement member.
Figure 21B:
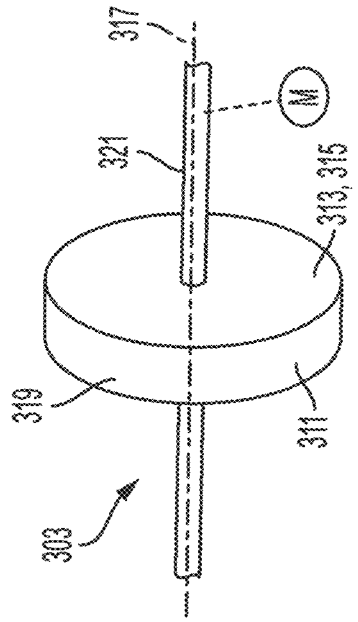
FIG. 21B is a perspective view of the rotatable displacement member of FIG. 21A.

In some configurations, the displacement surface 311 may advance in the machine direction MD at faster, slower, or identical speeds as the first elastic laminate 200*a*. For example, as shown in FIGS. 21A and 21B, the displacement apparatus 303 may comprise a displacement member 313 comprising a disk 315 adapted to rotate about a rotation axis 317 extending in the cross direction CD. An outer circumferential surface 319 of the disk 315 may define the displacement surface 311. As such, the displacement surface 311 may be adapted to orbit about the rotation axis 317. In some configurations, the rotation of the disk 315 may be a result of a frictional engagement between the first elastic laminate 200*a* and the displacement surface 311. In turn, advancement of the first elastic laminate 200*a* in the machine direction MD may cause the disk 315 rotate. In some configurations, the disk 315 may be connected with a shaft 321. In turn, the shaft 321 may be indirectly or directly connected with by a motor M. As such, the motor M may be adapted to rotate the shaft 321 and disk 315 to cause the displacement surface 311 to orbit about the rotation axis 317. It is to be appreciated that the displacement surface 311 may orbit at constant or variable angular velocities. In some configurations, the displacement surface 311 may advance in the machine direction MD at variable or constant speeds.

It is to be appreciated that the displacement apparatus 303 shown in FIGS. 20A-21B may be configured to hold the first edge 107*a* and the second edge 107*b* of the first elastic substrate 200*a* at constant elevations in the Z-direction when the first elastic substrate 200*a* is in contact with the displacement surface 311, such as discussed above for example with reference to FIG. 19.

In other examples, such as shown in FIGS. 22A-24B, the displacement member 313 may comprise a protuberance 323 extending radially outward from a rotating member 325, wherein the protuberance 323 comprises the displacement surface 311. The rotating member 325 may comprise support surfaces 327 adapted to support or hold the regions of the first elastic laminate adjacent the first edge 107*a* and the second edge 107*b* at constant elevations in the Z-direction when the first elastic substrate 200*a* is in contact with the displacement surface 311. As discussed below, the support surfaces 327 may be positioned across from and outside of the protuberance 323 and the support surface 311 in the cross direction CD. It is to be appreciated that the apparatus 303 shown in FIGS. 22A-24B may comprise similar components as described with reference to FIGS. 21A and 21B.

Figure 22A:
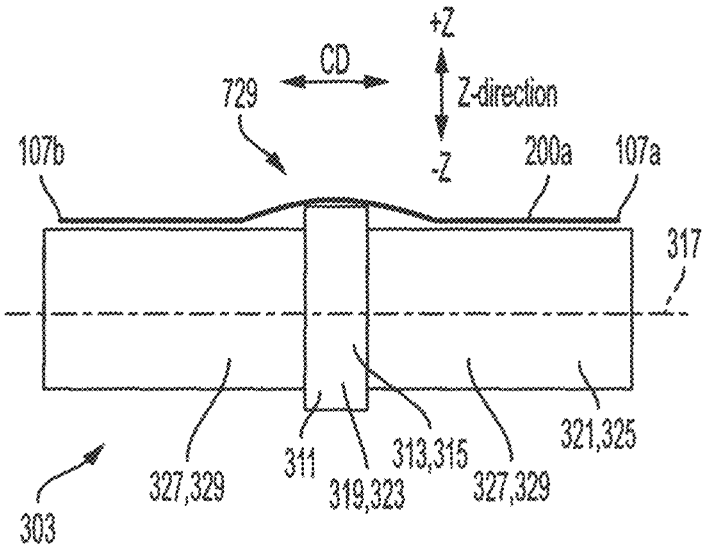
FIG. 22A a sectional view of the elastic laminate of FIG. 17, taken along line X-X advancing over a displacement apparatus comprising a rotatable displacement member comprising a support surface.
Figure 22B:
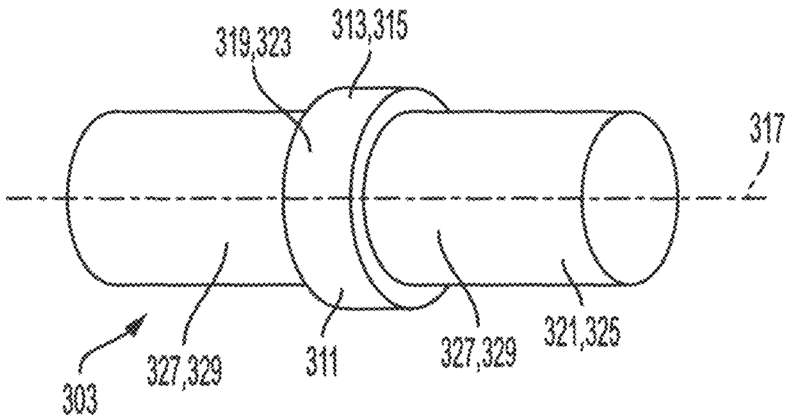
FIG. 22B is a perspective view of the rotatable displacement member of FIG. 22A.
Figure 23A:
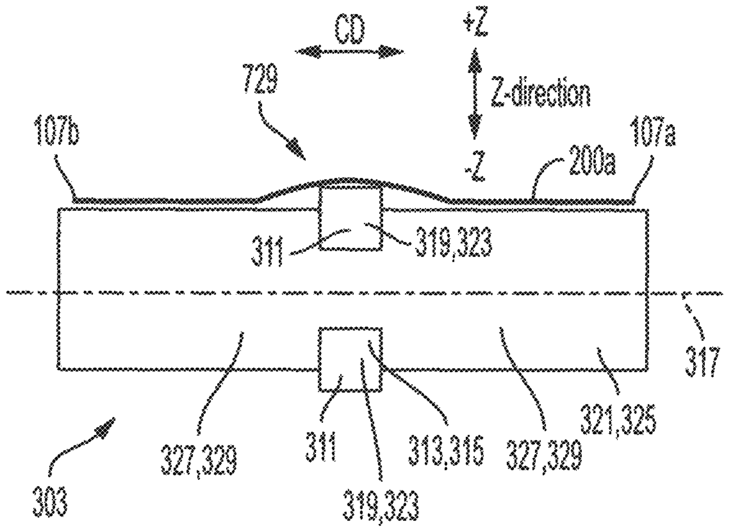
FIG. 23A a sectional view of the elastic laminate of FIG. 17, taken along line X-X advancing over a displacement apparatus comprising a first rotatable displacement member and second rotatable displacement member.
Figure 23B:
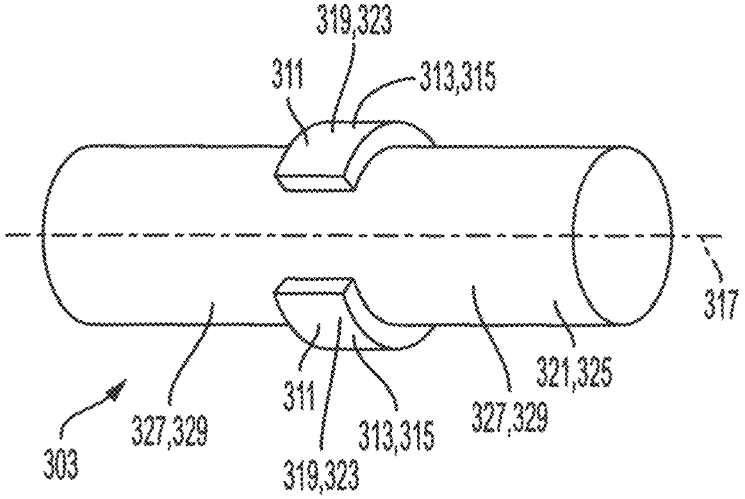
FIG. 23B is a perspective view of the rotatable displacement members of FIG. 23A.

As shown in FIGS. 22A and 22B, the protuberance 323 may extend contiguously circumferentially about the rotation axis 317 to define a ring or a disk 319. In addition, the displacement apparatus 303 may comprise support surfaces 327 defined by an outer circumferential surface 329 of rotating member 325 which may be in the form of the shaft 321. As such, the regions of the first elastic laminate 200*a* adjacent the side edges 107*a*, 107*b* may be supported at a constant Z-direction elevation by the support surfaces 327 while the first elastic laminate 200*a* is in contact with the displacement surface 311. In some configurations, the outer circumferential surface 329 of the shaft 321 may be connected with a vacuum system that may apply vacuum pressure to the first elastic laminate 200*a* to help hold the first elastic laminate 200*a* against the support surfaces 327 and/or the displacement surface 311. As shown in FIGS. 23A and 23B, the displacement apparatus 303 may be configured to comprise a plurality of protuberances 323 separate from each other and arranged circumferentially about the rotation axis 317.

Figure 24A:
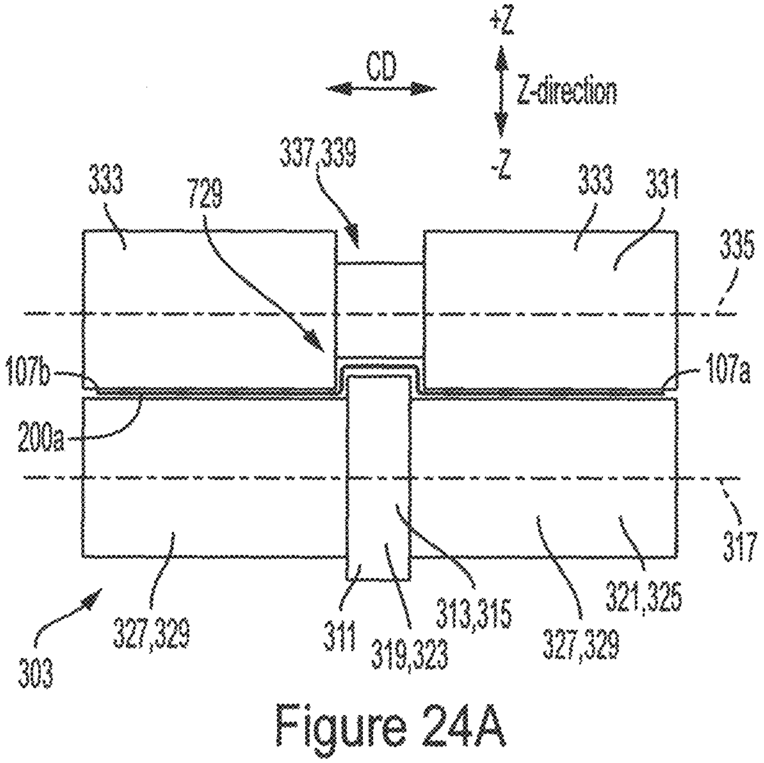
FIG. 24A a sectional view of the elastic laminate of FIG. 17, taken along line X-X advancing over a displacement apparatus comprising a rotatable displacement member comprising a support surface.
Figure 24B:
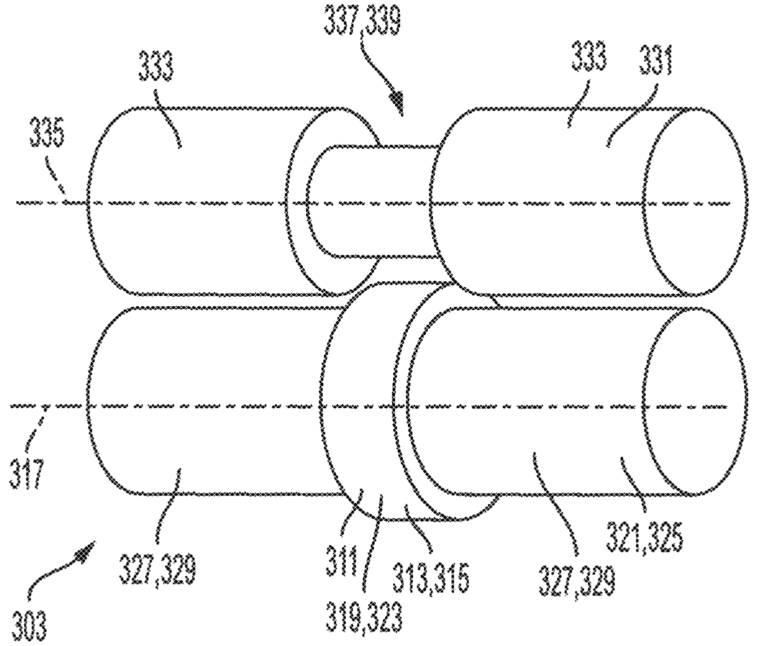
FIG. 24B is a perspective view of the rotatable displacement member of FIG. 24A.

As shown in FIGS. 24A and 24B, the displacement apparatus 303 may comprise a second rotating member 331 comprising an outer circumferential surface 333 adapted to rotate about a rotation axis 335 extending in the cross direction CD. The second rotating member 331 may comprise a recess 337 extending radially inward from the outer circumferential surface 333. In some configurations, the recess 337 may extend contiguously about the rotation axis 335 to define a groove 339. As such, the displacement surface 311 and the protuberance 323 may operate to force the region 729 of the first elastic laminate 200*a* into the recess 337.

Figure 25A:
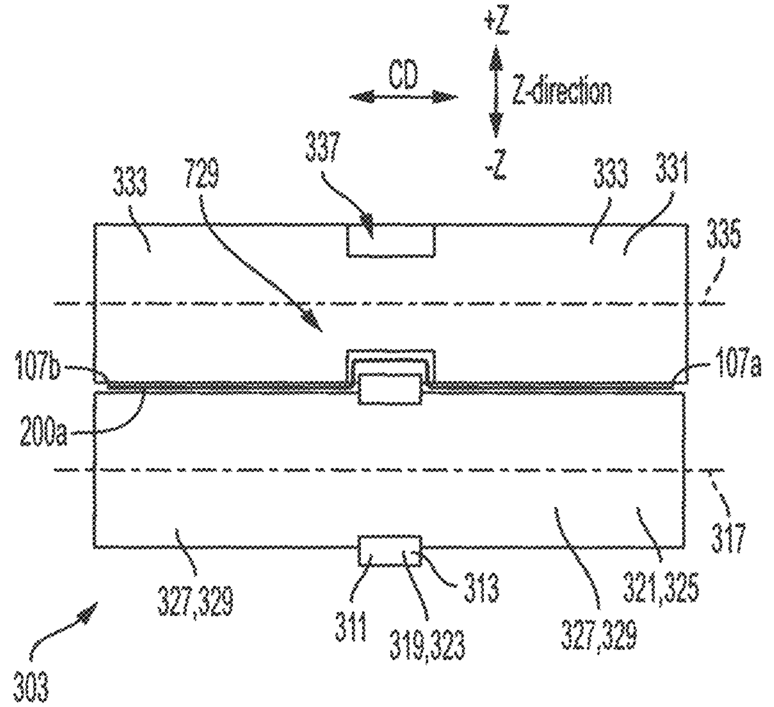
FIG. 25A a sectional view of the elastic laminate of FIG. 17, taken along line X-X advancing over a displacement apparatus comprising a first rotatable displacement member and second rotatable displacement member.
Figure 25B:
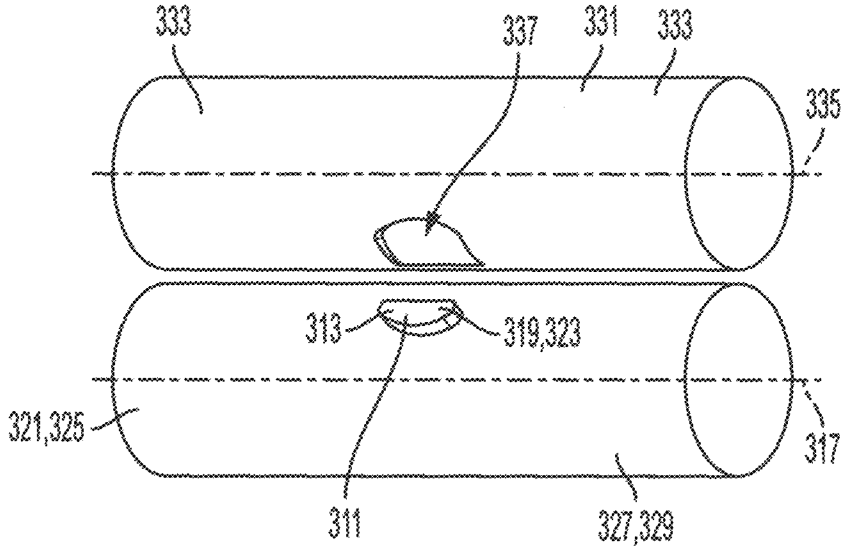
FIG. 25B is a perspective view of the rotatable displacement members of FIG. 25A.

As shown in FIGS. 25A and 25B, the displacement apparatus 303 may be configured to comprise a plurality of protuberances 323 separate from each other and arranged circumferentially about the rotation axis 317. In addition, the second rotating member 331 may be configured to comprise a plurality of separate recesses 337 adapted to receive the protuberances 323. It is also to be appreciated that the protuberances 323 and/or the recesses 337 may comprise shapes and/or contours that substantially correspond with each other and/or with shapes of the bond region 722.

Figure 26:
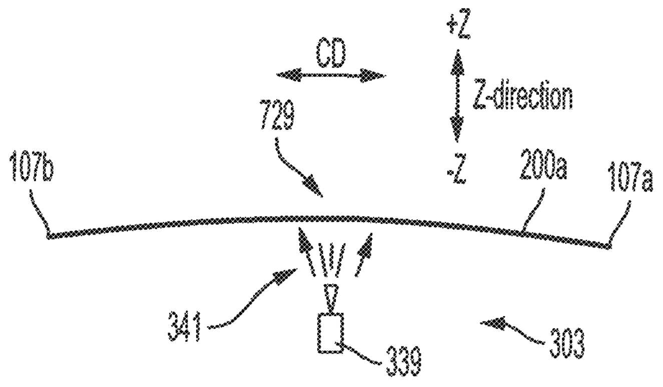
FIG. 26 a sectional view of the elastic laminate of FIG. 17, taken along line X-X advancing adjacent a displacement apparatus comprising a fluid nozzle.
Figure 27:
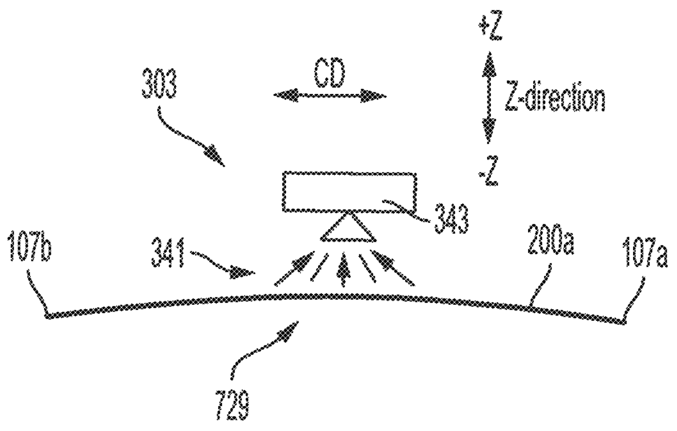
FIG. 27 a sectional view of the elastic laminate of FIG. 17, taken along line X-X advancing adjacent a displacement apparatus comprising a vacuum device.

It is to be appreciated that the displacement apparatus 303 may be configured in other various ways to displace a region 729 of the first elastic laminate 200*a* without the use of a displacement surface. For example, as shown in FIGS. 26, the displacement apparatus 303 may comprise a nozzle or similar device 339 to force a fluid 341, such as air, against the first elastic laminate to displace the first elastic laminate 200*a*. In another example, as shown in FIGS. 27, the displacement apparatus 303 may comprise a vacuum device 343 to draw a fluid 341, such as air, with vacuum pressure adjacent the first elastic laminate 200*a* to displace the region 729 of the first elastic laminate 200*a*. In yet another example, the displacement apparatus 303 may be adapted to operate with static energy to displace the region 729 the first elastic laminate 200*a*.

Average Decitex (Average-Dtex)

The Average Decitex Method is used to calculate the Average-Dtex on a length-weighted basis for elastic fibers present in an entire article, or in a specimen of interest extracted from an article. The decitex value is the mass in grams of a fiber present in 10,000 meters of that material in the relaxed state. The decitex value of elastic fibers or elastic laminates containing elastic fibers is often reported by manufacturers as part of a specification for an elastic fiber or an elastic laminate including elastic fibers. The Average-Dtex is to be calculated from these specifications if available. Alternatively, if these specified values are not known, the decitex value of an individual elastic fiber is measured by determining the cross-sectional area of a fiber in a relaxed state via a suitable microscopy technique such as scanning electron microscopy (SEM), determining the composition of the fiber via Fourier Transform Infrared (FT-IR) spectroscopy, and then using a literature value for density of the composition to calculate the mass in grams of the fiber present in 10,000 meters of the fiber. The manufacturer-provided or experimentally measured decitex values for the individual elastic fibers removed from an entire article, or specimen extracted from an article, are used in the expression below in which the length-weighted average of decitex value among elastic fibers present is determined.

The lengths of elastic fibers present in an article or specimen extracted from an article is calculated from overall dimensions of and the elastic fiber pre-strain ratio associated with components of the article with these or the specimen, respectively, if known. Alternatively, dimensions and/or elastic fiber pre-strain ratios are not known, an absorbent article or specimen extracted from an absorbent article is disassembled and all elastic fibers are removed. This disassembly can be done, for example, with gentle heating to soften adhesives, with a cryogenic spray (e.g., Quick-Freeze, Miller-Stephenson Company, Danbury, CT), or with an appropriate solvent that will remove adhesive but not swell, alter, or destroy elastic fibers. The length of each elastic fiber in its relaxed state is measured and recorded in millimeters (mm) to the nearest mm.

Calculation of Average-Dtex

For each of the individual elastic fibers $f_i$ of relaxed length $L_i$ and fiber decitex value $d_i$ (obtained either from the manufacturer's specifications or measured experimentally) present in an absorbent article, or specimen extracted from an absorbent article, the Average-Dtex for that absorbent article or specimen extracted from an absorbent article is defined as:

$$\text{Average-}Dtex = \frac{\sum_{i=1}^{n}(L_i \times d_i)}{\sum_{i=I}^{n} L_i}$$

where n is the total number of elastic fibers present in an absorbent article or specimen extracted from an absorbent article. The Average-Dtex is reported to the nearest integer value of decitex (grams per 10 000 m).

If the decitex value of any individual fiber is not known from specifications, it is experimentally determined as described below, and the resulting fiber decitex value(s) are used in the above equation to determine Average-Dtex.

Experimental Determination of Decitex Value for a Fiber

For each of the elastic fibers removed from an absorbent article or specimen extracted from an absorbent article according to the procedure described above, the length of each elastic fiber $L_k$ in its relaxed state is measured and recorded in millimeters (mm) to the nearest mm. Each elastic fiber is analyzed via FT-IR spectroscopy to determine its composition, and its density $\rho_k$ is determined from available literature values. Finally, each fiber is analyzed via SEM. The fiber is cut in three approximately equal locations perpendicularly along its length with a sharp blade to create a clean cross-section for SEM analysis. Three fiber segments with these cross sections exposed are mounted on an SEM sample holder in a relaxed state, sputter coated with gold, introduced into an SEM for analysis, and imaged at a resolution sufficient to clearly elucidate fiber cross sections. Fiber cross sections are oriented as perpendicular as possible to the detector to minimize any oblique distortion in the measured cross sections. Fiber cross sections may vary in shape, and some fibers may consist of a plurality of individual filaments. Regardless, the area of each of the three fiber cross sections is determined (for example, using diameters for round fibers, major and minor axes for elliptical fibers, and image analysis for more complicated shapes), and the average of the three areas $\alpha_k$ for the elastic fiber, in units of micrometers squared ($\mu m^2$), is recorded to the nearest 0.1 $\mu m^2$. The decitex $d_k$ of the kth elastic fiber measured is calculated by:

$$d_k = 10000 \text{ m} \times a_k \times \rho_k \times 10^{-6}$$

where $d_k$ is in units of grams (per calculated 10,000 meter length), $\alpha_k$ is in units of $\mu m^2$, and $\rho_k$ is in units of grams per cubic centimeter (g/cm$^3$). For any elastic fiber analyzed, the experimentally determined $L_k$ and $d_k$ values are subsequently used in the expression above for Average-Dtex.

Average-Strand-Spacing

Using a ruler calibrated against a certified NIST ruler and accurate to 0.5 mm, measure the distance between the two distal strands within a section to the nearest 0.5 mm, and then divide by the number of strands in that section−1

$$\text{Average-Strand-Spacing}=d/(n-1) \text{ where } n>1$$

report to the nearest 0.1 mm.

Average-Pre-Strain

The Average-Pre-Strain of a specimen are measured on a constant rate of extension tensile tester (a suitable instrument is the MTS Insight using Testworks 4.0 Software, as available from MTS Systems Corp., Eden Prairie, MN) using a load cell for which the forces measured are within 1% to 90% of the limit of the cell. Articles are conditioned at 23° C.±2° C. and 50% ±2% relative humidity for 2 hours prior to analysis and then tested under the same environmental conditions.

Program the tensile tester to perform an elongation to break after an initial gage length adjustment. First raise the cross head at 10 mm/min up to a force of 0.05N. Set the current gage to the adjusted gage length. Raise the crosshead at a rate of 100 mm/min until the specimen breaks (force drops 20% after maximum peak force). Return the cross head to its original position. Force and extension data is acquired at a rate of 100 Hz throughout the experiment.

Set the nominal gage length to 40 mm using a calibrated caliper block and zero the crosshead. Insert the specimen into the upper grip such that the middle of the test strip is positioned 20 mm below the grip. The specimen may be folded perpendicular to the pull axis, and placed in the grip to achieve this position. After the grip is closed the excess material can be trimmed. Insert the specimen into the lower grips and close. Once again, the strip can be folded, and then trimmed after the grip is closed. Zero the load cell. The specimen should have a minimal slack but less than 0.05 N of force on the load cell. Start the test program.

From the data construct a Force (N) verses Extension (mm). The Average-Pre-Strain is calculated from the bend in the curve corresponding to the extension at which the nonwovens in the elastic are engaged. Plot two lines, corresponding to the region of the curve before the bend (primarily the elastics), and the region after the bend (primarily the nonwovens). Read the extension at which these two lines intersect, and calculate the % Pre-Strain from the extension and the corrected gage length. Record as % Pre-strain 0.1%. Calculate the arithmetic mean of three replicate samples for each elastomeric laminate and Average-Pre-Strain to the nearest 0.1%.

Combinations

A1. A method for assembling absorbent articles, the method comprising steps of: providing a substrate comprising a first edge separated from a second edge in a cross direction; advancing the substrate in a machine direction; forming a bond region in the substrate, the bond region comprising a leading edge and a trailing edge and comprising material of the substrate fused together extending between the leading edge region and the trailing edge region; forming a frangible pathway in the substrate extending between the bond region and the first edge of the substrate; breaking the bond region to form a slit through the substrate between the leading edge region and the trailing edge region by displacing the bond region in a Z-direction that is normal to the machine direction and the cross direction relative to the first side edge and the second side edge of the substrate; and providing a chassis comprising a topsheet, a backsheet, and an absorbent core positioned between the topsheet and the backsheet; and bonding a portion of the chassis with the substrate to define a chassis overlap region.

A2. The method of paragraph A1, wherein the substrate comprises two or more layers.

A3. The method of paragraph A1 of A2, wherein the substrate comprises an elastic laminate.

A4. The method of any of paragraphs A1 to A3, wherein the step of providing the substrate further comprises bonding a fastener component with the elastic laminate; and wherein the bond region extends across a portion of the fastener component.

A5. The method of paragraph A4, wherein the fastener component comprises hooks protruding from a base, and wherein the bond region comprises materials of the base and the elastic laminate fused together.

A6. The method of paragraph A4, wherein the fastener component is positioned between the elastic laminate and the backsheet.

A7. The method of any of paragraphs A1 to A6, wherein the step of forming the bond region further comprises advancing the substrate through a nip between a pattern surface and a pressing surface.

A8. The method of paragraph A7, wherein the pressing surface comprises an outer circumferential surface of an anvil roll.

A9. The method of paragraph A7, wherein the pressing surface comprises an energy transfer surface of an ultrasonic horn.

A10. The method of paragraph A7, wherein the pattern surface comprises a blade extending radially outward from a knife roll adapted to rotate about a rotation axis extending in the cross direction.

A11. The method of any of paragraphs A1 to A10, further comprising a step of providing a displacement surface, and wherein the step of breaking the bond region further comprises advancing the substrate in contact with the displacement surface to displace the bond region in the Z-direction.

A12. The method of paragraph A11, wherein the first edge and the second edge of the substrate are positioned in different elevations in the Z-direction than the displacement surface when the substrate is in contact with the displacement surface.

A13. The method of paragraph A12, further comprising a step of holding the first edge and the second edge of the substrate at constant elevations in the Z-direction when the substrate is in contact with the displacement surface.

A14. The method of paragraph A11, wherein the substrate moves relative to the displacement surface.

A15. The method of paragraph A11, wherein the displacement surface is stationary and does not advance in the machine direction.

A16. The method of paragraph A11, wherein the displacement surface advances in the machine direction.

A17. The method of paragraph A16, wherein the displacement surface and the substrate advance in the machine direction at substantially identical speeds.

A18. The method of paragraph A16, wherein the displacement surface is adapted to orbit about a first axis extending in the cross direction.

A19. The method of paragraph A18, wherein advancement of the substrate in contact with displacement surface causes the displacement surface to orbit about the first axis.

A20. The method of paragraph A18, wherein displacement apparatus further comprises a motor that drives the displacement surface to orbit about the first axis.

A21. The method of paragraph A20, wherein the displacement surface orbits about the first axis at a variable angular velocity.

A22. The method of paragraph A18, further comprising a step of providing a first rotating member adapted to rotate about the first axis, and the displacement surface comprises a protuberance extending radially outward from the rotating member.

A23. The method of paragraph A22, wherein the protuberance extends contiguously circumferentially about the first axis to define a ring.

A24. The method of paragraph A22, further comprising a plurality of protuberances separate from each other and arranged circumferentially about the first axis.

A25. The method of paragraph A22, further comprising a step of providing a second rotating member comprising an outer circumferential surface adapted to rotate about a second axis extending in the cross direction.

A26. The method of paragraph A25, wherein the second rotating member comprises at least one recess extending radially inward from the outer circumferential surface, and wherein the step of displacing the bond region in the Z-direction further comprises forcing a portion of the bond region into the at least one recess with the protuberance.

A27. The method of paragraph A26, wherein the at least one recess extends contiguously about the second axis to define a groove.

A28. The method of any of paragraphs A1 to A10, wherein the step of breaking the bond region further comprises displacing the bond region in the Z-direction with a fluid.

A29. The method of paragraph A28, wherein the fluid comprises air.

A30. The method of paragraph A28, further comprising a step of ejecting the fluid onto the substrate.

A31. The method of paragraph A28, further comprising a step of drawing the fluid onto the substrate with vacuum pressure.

A32. The method of any of paragraphs A1 to A31, wherein the step of breaking the bond region further comprises displacing the bond region in the Z-direction with static energy.

A33. The method of paragraph 1, wherein the slit and at least a portion of the frangible pathway are positioned in the chassis overlap region.

Bio-Based Content for Components

Components of the absorbent articles described herein may at least partially be comprised of bio-based content as described in U.S. Pat. Appl. No. 2007/0219521 A1. For example, the superabsorbent polymer component may be bio-based via their derivation from bio-based acrylic acid. Bio-based acrylic acid and methods of production are further described in U.S. Pat. Appl. Pub. No. 2007/0219521 and U.S. Pat. Nos. 8,703,450; 9,630,901 and 9,822,197. Other components, for example nonwoven and film components, may comprise bio-based polyolefin materials. Bio-based polyolefins are further discussed in U.S. Pat. Appl. Pub. Nos. 2011/0139657, 2011/0139658, 2011/0152812, and 2016/0206774, and U.S. Pat. No. 9,169,366. Example bio-based polyolefins for use in the present disclosure comprise polymers available under the designations SHA7260™, SHE150™, or SGM9450F™ (all available from Braskem S. A.).

An absorbent article component may comprise a bio-based content value from about 10% to about 100%, from about 25% to about 100%, from about 40% to about 100%, from about 50% to about 100%, from about 75% to about 100%, or from about 90% to about 100%, for example, using ASTM D6866-10, method B.

Recycle Friendly and Bio-Based Absorbent Articles

Components of the absorbent articles described herein may be recycled for other uses, whether they are formed, at least in part, from recyclable materials. Examples of absorbent article materials that may be recycled are nonwovens, films, fluff pulp, and superabsorbent polymers. The recycling process may use an autoclave for sterilizing the absorbent articles, after which the absorbent articles may be shredded and separated into different byproduct streams. Example byproduct streams may comprise plastic, superabsorbent polymer, and cellulose fiber, such as pulp. These byproduct streams may be used in the production of fertilizers, plastic articles of manufacture, paper products, viscose, construction materials, absorbent pads for pets or on hospital beds, and/or for other uses. Further details regarding absorbent articles that aid in recycling, designs of recycle friendly diapers, and designs of recycle friendly and bio-based component diapers, are disclosed in U.S. Pat. Appl. Publ. No. 2019/0192723, published on Jun. 27, 2019.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling absorbent articles, the method comprising steps of:
- providing a substrate comprising a first edge separated from a second edge in a cross direction;
- advancing the substrate in a machine direction;
- forming a bond region in the substrate, the bond region comprising a leading edge region and a trailing edge region and comprising material of the substrate fused together extending between the leading edge region and the trailing edge region;
- forming a frangible pathway in the substrate extending between the bond region and the first edge of the substrate;
- breaking the bond region to form a slit through the substrate between the leading edge region and the trailing edge region by displacing the bond region in a Z-direction that is normal to the machine direction and the cross direction relative to the first side edge and the second side edge of the substrate; and
- providing a chassis comprising a topsheet, a backsheet, and an absorbent core positioned between the topsheet and the backsheet; and
- bonding a portion of the chassis with the substrate to define a chassis overlap region.

2. The method of claim 1, wherein the substrate comprises two or more layers.

3. The method of claim 2, wherein the substrate comprises an elastic laminate.

4. The method of claim 3, wherein the step of providing the substrate further comprises bonding a fastener component with the elastic laminate; and wherein the bond region extends across a portion of the fastener component.

5. The method of claim 4, wherein the fastener component comprises hooks protruding from a base, and wherein the bond region comprises materials of the base and the elastic laminate fused together.

6. The method of claim 4, wherein the fastener component is positioned between the elastic laminate and the backsheet.

7. The method of claim 1, wherein the step of forming the bond region further comprises advancing the substrate through a nip between a pattern surface and a pressing surface.

8. The method of claim 7, wherein the pressing surface comprises an outer circumferential surface of an anvil roll.

9. The method of claim 7, wherein the pressing surface comprises an energy transfer surface of an ultrasonic horn.

10. The method of claim 7, wherein the pattern surface comprises a blade extending radially outward from a knife roll adapted to rotate about a rotation axis extending in the cross direction.

11. The method of claim 1, further comprising a step of providing a displacement surface, and wherein the step of breaking the bond region further comprises advancing the substrate in contact with the displacement surface to displace the bond region in the Z-direction.

12. The method of claim 11, wherein the first edge and the second edge of the substrate are positioned in different elevations in the Z-direction than the displacement surface when the substrate is in contact with the displacement surface.

13. The method of claim 12, further comprising a step of holding the first edge and the second edge of the substrate at constant elevations in the Z-direction when the substrate is in contact with the displacement surface.

14. The method of claim 11, wherein the substrate moves relative to the displacement surface.

15. The method of claim 11, wherein the displacement surface is stationary and does not advance in the machine direction.

16. The method of claim 11, wherein the displacement surface advances in the machine direction.

17. The method of claim 16, wherein the displacement surface and the substrate advance in the machine direction at substantially identical speeds.

18. The method of claim 16, wherein the displacement surface is adapted to orbit about a first axis extending in the cross direction.

19. The method of claim 18, wherein advancement of the substrate in contact with displacement surface causes the displacement surface to orbit about the first axis.

20. The method of claim 18, further comprising a step of providing a motor adapted to drive the displacement surface to orbit about the first axis.

21. The method of claim 20, wherein the displacement surface orbits about the first axis at a variable angular velocity.

22. The method of claim 18, further comprising a step of providing a first rotating member adapted to rotate about the first axis, and the displacement surface comprises a protuberance extending radially outward from the rotating member.

23. The method of claim 22, wherein the protuberance extends contiguously circumferentially about the first axis to define a ring.

24. The method of claim 22, further comprising a plurality of protuberances separate from each other and arranged circumferentially about the first axis.

25. The method of claim 22, further comprising a step of providing a second rotating member comprising an outer circumferential surface adapted to rotate about a second axis extending in the cross direction.

26. The method of claim 25, wherein the second rotating member comprises at least one recess extending radially inward from the outer circumferential surface, and wherein the step of displacing the bond region in the Z-direction further comprises forcing a portion of the bond region into the at least one recess with the protuberance.

27. The method of claim 26, wherein the at least one recess extends contiguously about the second axis to define a groove.

28. The method of claim 1, wherein the step of breaking the bond region further comprises displacing the bond region in the Z-direction with a fluid.

29. The method of claim 28, wherein the fluid comprises air.

30. The method of claim 28, further comprising a step of ejecting the fluid onto the substrate.

31. The method of claim 28, further comprising a step of drawing the fluid onto the substrate with vacuum pressure.

32. The method of claim 1, wherein the step of breaking the bond region further comprises displacing the bond region in the Z-direction with static energy.

33. The method of claim 1, wherein the slit and at least a portion of the frangible pathway are positioned in the chassis overlap region.

* * * * *